United States Patent
Ganesan et al.

(10) Patent No.: US 12,115,064 B2
(45) Date of Patent: *Oct. 15, 2024

(54) SYSTEMS AND METHODS FOR HEART VALVE THERAPY

(71) Applicant: Caisson Interventional LLC, Maple Grove, MN (US)

(72) Inventors: Kavitha Ganesan, Maple Grove, MN (US); Ramji Iyer, Maple Grove, MN (US); Todd J. Mortier, Mound, MN (US); Cyril J. Schweich, Jr., Maple Grove, MN (US); Benjamin L. Montag, Delano, MN (US); Steven N. Willard, Bloomington, MN (US)

(73) Assignee: Caisson Interventional LLC, Maple Grove, MN (US)

( * ) Notice: Subject to any disclaimer, the term of this patent is extended or adjusted under 35 U.S.C. 154(b) by 51 days.

This patent is subject to a terminal disclaimer.

(21) Appl. No.: 18/176,433

(22) Filed: Feb. 28, 2023

(65) Prior Publication Data

US 2023/0200988 A1 Jun. 29, 2023

Related U.S. Application Data

(60) Continuation of application No. 17/082,718, filed on Oct. 28, 2020, now Pat. No. 11,612,481, which is a
(Continued)

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01);
(Continued)

(58) Field of Classification Search
CPC .... A61F 2/2418; A61F 2/2433; A61F 2/2436; A61F 2/2439; A61F 2/2454; A61F 2/2466
See application file for complete search history.

(56) References Cited

U.S. PATENT DOCUMENTS

| 5,957,949 A | 9/1999 | Leonhardt et al. |
| 11,612,481 B2 | 3/2023 | Ganesan et al. |

(Continued)

FOREIGN PATENT DOCUMENTS

| WO | 2008/029296 A2 | 3/2008 |
| WO | 2013/150512 A1 | 10/2013 |

OTHER PUBLICATIONS

International Search Report and Written Opinion in International Application No. PCT/US2018/016969, dated Apr. 24, 2018, 12 pages.

*Primary Examiner* — Suba Ganesan

(57) ABSTRACT

Prosthetic heart valves described herein can be deployed using a transcatheter delivery system and technique to interface and anchor in cooperation with the anatomical structures of a native heart valve. Some embodiments of prosthetic valves described herein include an anchor portion that couples to the anatomy near a native valve, and a valve portion that is mateable with the anchor portion. In some such embodiments, the anchor portion and/or the deployment system includes one or more prosthetic elements that temporarily augment or replace the sealing function of the native valve leaflets.

15 Claims, 40 Drawing Sheets

Related U.S. Application Data division of application No. 15/889,576, filed on Feb. 6, 2018, now Pat. No. 10,869,758.

(60) Provisional application No. 62/455,371, filed on Feb. 6, 2017.

(52) U.S. Cl.
CPC .......... *A61F 2/2439* (2013.01); *A61F 2/2454* (2013.01); *A61F 2/246* (2013.01); *A61F 2/2466* (2013.01); *A61F 2210/0014* (2013.01); *A61F 2220/0008* (2013.01); *A61F 2230/0034* (2013.01); *A61F 2230/0093* (2013.01); *A61F 2250/006* (2013.01); *A61F 2250/0098* (2013.01)

(56) References Cited

U.S. PATENT DOCUMENTS

| | | |
|---|---|---|
| 2009/0222082 A1 | 9/2009 | Lock et al. |
| 2012/0053680 A1 | 3/2012 | Bolling et al. |
| 2013/0304200 A1 | 11/2013 | McLean et al. |
| 2015/0230919 A1 | 8/2015 | Chau et al. |
| 2016/0113768 A1 | 4/2016 | Ganesan et al. |
| 2016/0270911 A1* | 9/2016 | Ganesan ............... A61F 2/2439 |
| 2016/0331523 A1* | 11/2016 | Chau ..................... A61F 2/2454 |
| 2017/0143478 A1 | 5/2017 | Schwartz et al. |
| 2018/0221147 A1 | 8/2018 | Ganesan et al. |
| 2021/0038383 A1 | 2/2021 | Ganesan et al. |

* cited by examiner

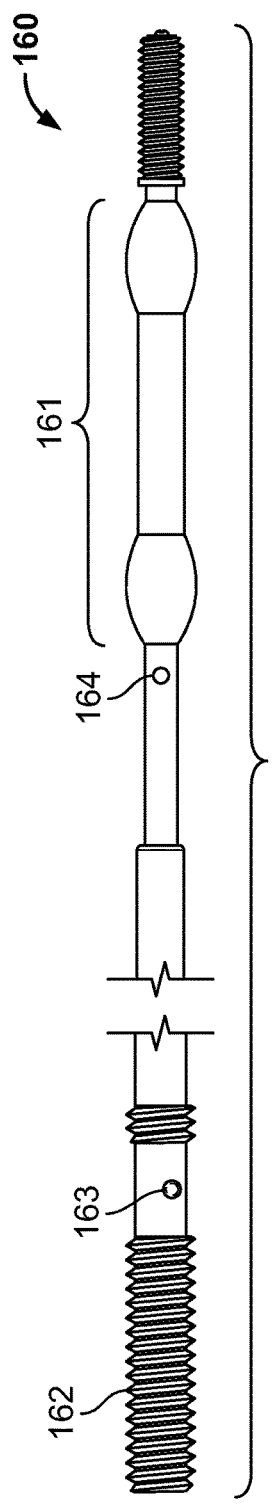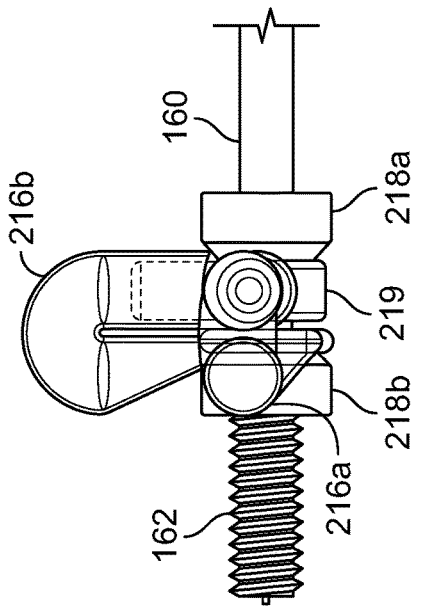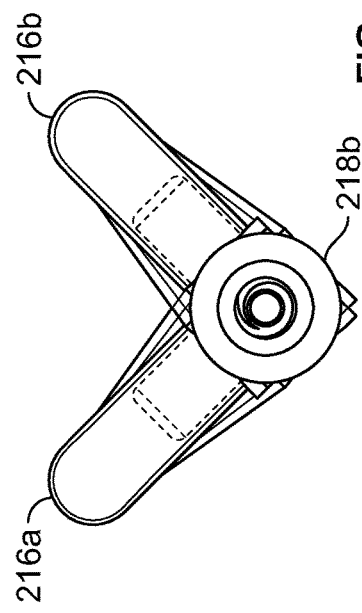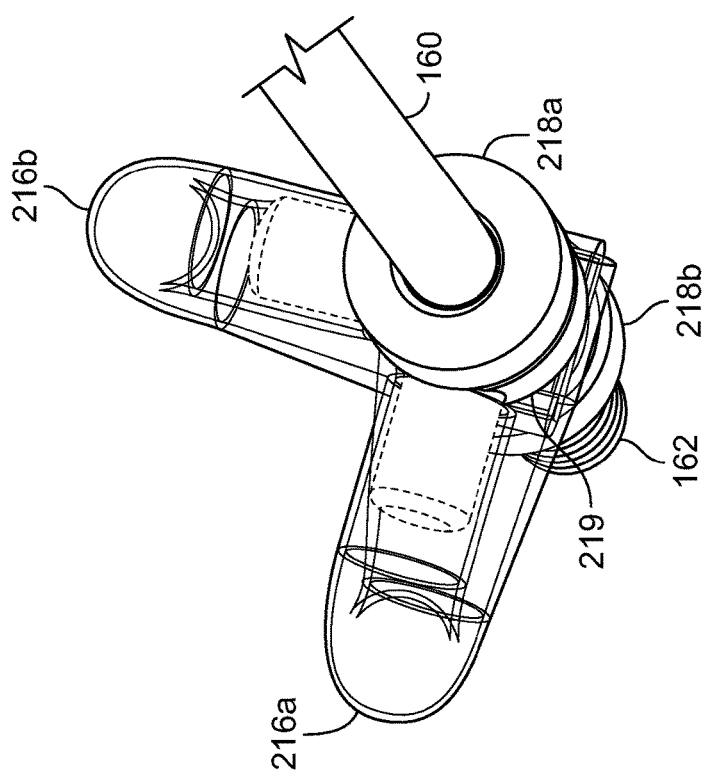

SYSTEMS AND METHODS FOR HEART VALVE THERAPY

CROSS-REFERENCE TO RELATED APPLICATIONS

This application is a continuation of U.S. application Ser. No. 17/082,718 filed Oct. 28, 2020, titled SYSTEMS AND METHODS FOR HEART VALVE THERAPY, which is a divisional of U.S. application Ser. No. 15/889,576, filed Feb. 6, 2018, titled SYSTEMS AND METHODS FOR HEART VALVE THERAPY, which claims the benefit of U.S. Provisional Application Ser. No. 62/455,371, filed Feb. 6, 2017, titled SYSTEMS AND METHODS FOR HEART VALVE THERAPY, the entire disclosures of which are expressly incorporated herein by reference.

TECHNICAL FIELD

This document relates to implantable devices for treating heart valves. For example, this document relates to implantable devices such as prosthetic mitral valves that can be implanted using transcatheter techniques. Some embodiments of prosthetic valves described herein include an anchor portion that couples the prosthetic valve to the anatomy near a native valve, and a valve portion that is mateable with the anchor portion. In some such embodiments, the anchor portion and/or the deployment system includes one or more prosthetic elements that augment or replace the sealing function of the native valve leaflets.

BACKGROUND

The long-term clinical effect of valve regurgitation is recognized as a significant contributor to cardiovascular related morbidity and mortality. Thus, for many therapies intended to treat the mitral valve, one primary goal is to significantly reduce or eliminate regurgitation. By eliminating the regurgitation at the mitral valve, the destructive volume overload effects on the left ventricle can be attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumetric contraction. Additionally, therapies for MR reduction can have the effect of reducing the elevated pressures in the left atrium and pulmonary vasculature reducing pulmonary edema (congestion) and shortness of breath symptomatology. Such therapies for MR reduction may also have a positive effect on the filling profile of the left ventricle (LV) and the restrictive LV physiology that can result with MR. These pathophysiologic issues indicate the potential benefits of MR therapy, but also indicate the complexity of the system and the need for a therapy to focus beyond the MR level or grade.

In some percutaneous access procedures in which a medical device is introduced through a patient's skin and into a patient's blood vessel, such an access can be used to introduce devices into the patient without the use of large cut downs, which can be painful and in some cases can hemorrhage or become infected. A percutaneous access generally employs only a small hole through the skin, which subsequently seals relatively easily, and heals quickly in comparison to a surgical cut down.

SUMMARY

This document describes implantable prosthetic devices, such as prosthetic mitral valves and other prosthetic devices that can interface and anchor in cooperation with the anatomical structures of a native heart valve. Some embodiments of prosthetic devices described herein include an anchor portion that couples a prosthetic mitral valve to the anatomy near the native mitral valve. In some such embodiments, the anchor portion and/or the deployment system includes prosthetic elements that augment or perform the sealing function of the native valve leaflets, either temporarily or permanently. In some embodiments, the prosthetic heart valves may also include a valve portion that is mateable with the anchor portion. For example, the anchor portion may define an interior space, and a prosthetic valve assembly comprising a valve frame and multiple valve leaflets attached to the valve frame may releasably couple with the prosthetic anchor assembly within the interior space. In some implementations, an implantable prosthetic device and deployment system includes a prosthetic mitral valve device, a system of multiple catheters configured to deliver the prosthetic mitral valve system, and a deployment frame system.

In one aspect, this disclosure is directed to a prosthetic mitral valve system. The prosthetic mitral valve system includes an anchor assembly comprising an expandable anchor frame with a prosthetic element attached to the expandable anchor frame and a valve assembly comprising an expandable valve frame with an occluder attached to the expandable valve frame. The valve assembly is selectively coupleable with the anchor assembly. The anchor assembly is coupleable with a native mitral valve having an anterior leaflet and a posterior leaflet that cycle between an open valve orientation and a closed valve orientation in which free edges of the anterior and posterior leaflets oppose each other to define a coaptation line. While the anchor assembly is coupled with the native mitral valve: (i) the anterior and posterior leaflets continue to cycle and (ii) at least a portion of the prosthetic element is positioned along the coaptation line between the free edges of the anterior and posterior leaflets while the anterior and posterior leaflets are in the closed valve orientation.

Such a prosthetic mitral valve system may optionally include one or more of the following features. The prosthetic element may be configured to function as a prosthetic posterior leaflet while the anchor assembly is coupled with the native mitral valve. The prosthetic element may be made of a single, continuous member. The prosthetic element may comprise multiple members that are not directly connected to each other. The prosthetic element may comprise three members that are not directly connected to each other. The prosthetic element may comprise flexible, sheet-like material. In some embodiments, the prosthetic element is attached to a portion of the expandable anchor frame that is positioned superior to an annulus of the native mitral valve while the anchor assembly is coupled with the native mitral valve. The prosthetic mitral valve system may also include one or more tethers attached to the prosthetic element and to a portion of the expandable anchor frame that is positioned inferior to the annulus of the native mitral valve while the anchor assembly is coupled with the native mitral valve. The prosthetic element may comprise two or more separate members that are attached to the anchor assembly in a fully-circumferential arrangement. The prosthetic element may include a first prosthetic element configured to function as a prosthetic posterior leaflet while the anchor assembly is coupled with the native mitral valve, and a second prosthetic element configured to function as a prosthetic anterior leaflet while the anchor assembly is coupled with the native mitral valve. In some embodiments, the prosthetic element comprises three separate prosthetic elements.

In another aspect, this disclosure is directed to a prosthetic mitral valve and a deployment system. The prosthetic mitral valve includes: (i) an anchor assembly including an expandable anchor frame coupleable with a native mitral valve having an anterior leaflet and a posterior leaflet that cycle between an open valve orientation and a closed valve orientation in which free edges of the anterior and posterior leaflets oppose each other to define a coaptation line and (ii) a valve assembly including an expandable valve frame and an occluder attached to the expandable valve frame. The valve assembly is selectively coupleable with the anchor assembly. While the anchor assembly is coupled with the native mitral valve, the anterior and posterior leaflets continue to cycle. The deployment system includes multiple catheters configured to deliver the prosthetic mitral valve. At least some of the catheters are slidably engageable with each other and are releasably coupleable to the prosthetic mitral valve. A first catheter of the multiple catheters is releasably coupleable to the anchor assembly and includes an expandable element that is positioned along the coaptation line between the free edges of the anterior and posterior leaflets while: (i) the first catheter is coupled to the anchor assembly, (ii) the anchor assembly is coupled to the native mitral valve, and (iii) the anterior and posterior leaflets are in the closed valve orientation.

Such a prosthetic mitral valve and deployment system may optionally include one or more of the following features. The expandable element may include a selectively expandable balloon. The expandable element may include a self-expanding wireframe and a covering material attached thereto. The expandable element may include a passively-expandable, flexible sock member. The anchor assembly may include a hub that is positioned inferior to the annulus of the native mitral valve while the anchor assembly is coupled with the native mitral valve, and the first catheter may be releasably coupleable to the hub. A second catheter of the multiple catheters may be slidably engaged over the first catheter and slidably engageable over the expandable element. The second catheter may be releasably coupleable to the valve assembly. The expandable element may comprise a selectively expandable balloon that is non-spherical when expanded. The expandable element may comprise a first balloon and a second balloon. The first balloon and the second balloon may each be selectively expandable. The first balloon and the second balloon may each be selectively expandable longitudinally and transversely in relation to the first catheter. The system may also include a manifold comprising a first nozzle and a second nozzle. The first balloon may be coupled to the first nozzle and the second balloon may be coupled to the second nozzle. An axis of the first nozzle and an axis of the second nozzle may be non-linear to one another. An angle between the axis of the first nozzle and the axis of the second nozzle may be between 70 degrees and 110 degrees. The axis of the first nozzle and the axis of the second nozzle may each extend radially from the first catheter.

In another aspect, this disclosure is directed to a method for deploying a prosthetic mitral valve system within a native mitral valve having an anterior leaflet and a posterior leaflet that cycle between an open valve orientation and a closed valve orientation in which free edges of the anterior and posterior leaflets oppose each other to define a coaptation line. The method includes: (a) navigating a delivery sheath of a prosthetic mitral valve delivery system through a vasculature of the patient such that a distal end of the delivery sheath is positioned adjacent the native mitral valve; (b) expressing an anchor assembly of the prosthetic mitral valve system from the distal end of the delivery sheath such that the anchor assembly at least partially expands, the anchor assembly configured to selectively mate with a valve assembly of the prosthetic mitral valve system, the anchor assembly comprising an expandable anchor frame and a prosthetic element attached to the expandable anchor frame; (c) coupling the anchor assembly with the native mitral valve, wherein while the anchor assembly is coupled with the native mitral valve: (i) the anterior and posterior leaflets continue to cycle and (ii) at least a portion of the prosthetic element is positioned along the coaptation line between the free edges of the anterior and posterior leaflets while the anterior and posterior leaflets are in the closed valve orientation; and (d) mating the valve assembly with the anchor assembly, wherein the valve assembly comprises an expandable valve frame and an occluder attached to the expandable valve frame.

In another aspect, this disclosure is directed to a method for using a catheter deployment system to deploy a prosthetic mitral valve system within a native mitral valve having an anterior leaflet and a posterior leaflet that cycle between an open valve orientation and a closed valve orientation in which free edges of the anterior and posterior leaflets oppose each other to define a coaptation line. The method includes: (i) navigating a delivery sheath of the catheter deployment system through a vasculature of the patient such that a distal end of the delivery sheath is positioned adjacent the native mitral valve; (ii) expressing an anchor assembly of the prosthetic mitral valve system from the distal end of the delivery sheath by extending a catheter distally in relation to the delivery sheath, the catheter releasably coupled to the anchor assembly, the anchor assembly configured to selectively mate with a valve assembly of the prosthetic mitral valve system, the anchor assembly comprising an expandable anchor frame, the catheter including an expandable element; (iii) coupling the anchor assembly with the native mitral valve; (iv) while the catheter is coupled to the anchor assembly and the anchor assembly is coupled with the native mitral valve, expanding the expandable element such that the expandable element is positioned along the coaptation line between the free edges of the anterior and posterior leaflets; and (v) mating the valve assembly with the anchor assembly.

In another aspect, this disclosure is directed to a mitral valve system for deployment within a native mitral valve. The mitral valve system for deployment within a native mitral valve includes: valve means and means for anchoring the valve means within the native mitral valve annulus, the means for anchoring the valve means including an element for temporarily occluding regurgitation of blood flow from a left ventricle to a left atrium prior to receiving the valve means.

In another aspect, this disclosure is directed to a transcatheter mitral valve replacement system that includes: a valve assembly comprising an expandable valve frame and a set of occluder leaflets attached to the expandable valve frame; and an anchor assembly comprising an expandable anchor frame and a prosthetic valve sealing element attached to the expandable anchor frame, the anchor assembly configured to anchor to a native mitral valve and to receivingly mate with the valve assembly.

Some or all of the embodiments described herein may provide one or more of the following advantages. First, some embodiments of the prosthetic mitral valve systems provided herein can be used in a percutaneous transcatheter mitral replacement procedure (e.g., complete delivery and anchoring of the prosthetic valve components via one or more catheters advanced percutaneously into the venous system or arterial system and to the heart) that is safe, reliable, and repeatable by surgeons and/or interventional cardiologists of a variety of different skill levels. For example, in some implementations the prosthetic mitral valve system can establish a reliable and consistent anchor/substrate to which the valve/occluder structure subsequently engages. Thus, the prosthetic mitral valve system can be specifically designed to make use of the geometry/mechanics of the native mitral valve to create sufficient holding capability. In one particular aspect, the anatomical gutter found below a native mitral valve annulus can be utilized as a site for anchoring the prosthetic mitral valve system, yet the anchoring structure can be deployed in a manner that maintains native leaflet function of the mitral valve, thereby providing the ability to completely separate and stage the implantation of the components of the prosthetic mitral valve system. Accordingly, some embodiments of the prosthetic mitral valve systems described herein are configured to be implanted in a reliable, repeatable, and simplified procedure that is broadly applicable to a variety of patients and physicians, while also employing a significantly less invasive method.

Second, some embodiments of the prosthetic mitral valve systems provided herein are configured with one or more prosthetic elements that can reduce or substantially eliminate valvular regurgitation during the implantation process and, in some cases, on an ongoing basis thereafter. For example, some anchor assemblies can include one or more portions of flexible material that augment the function of the native posterior leaflet. Moreover, in some embodiments such portions of flexible material can be arranged to comprise a fully circumferential, multi-leaflet prosthetic valve. In some implementations, such anchor assemblies can provide temporary mitigation of valvular regurgitation, such as during the prosthetic valve deployment process. In some implementations, such anchor assemblies can provide ongoing mitigation of valvular regurgitation.

Third, some embodiments of the catheter-based systems for deploying the prosthetic mitral valve systems provided herein are configured with one or more prosthetic elements that can reduce or substantially eliminate valvular regurgitation during the prosthetic valve implantation process. For example, some deployment catheters include an expandable member that acts as a temporary spacer in the area of native valve leaflet coaptation. The expandable members can thereby enhance the sealing function of the native leaflets such that valvular regurgitation during the prosthetic valve deployment process is advantageously mitigated.

Fourth, using the devices, systems, and methods described herein, various medical conditions, such as heart valve conditions, can be treated in a minimally invasive fashion. Such minimally invasive techniques can tend to reduce recovery times, patient discomfort, and treatment costs.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 55 shows a side view of an inner catheter assembly with ports for inflation of the inflatable device of FIG. 50.

FIG. 56 shows a perspective top view of the inflatable device of FIG. 50, with deflated balloons, coupled to the inner catheter assembly of FIG. 55.

FIG. 57 shows a side view of the inflatable device of FIG. 50, with deflated balloons, coupled to the inner catheter assembly of FIG. 55.

FIG. 58 shows a top view of the inflatable device of FIG. 50, with deflated balloons, coupled to the inner catheter assembly of FIG. 55.

Like reference symbols in the various drawings indicate like elements.

DETAILED DESCRIPTION OF ILLUSTRATIVE EMBODIMENTS

This disclosure describes embodiments of a prosthetic heart valve system, such as prosthetic mitral valve systems, and transcatheter systems and methods for implanting prosthetic heart valve systems. In some embodiments, the prosthetic mitral valve system can be deployed to interface and anchor in cooperation with the native anatomical structures of a mitral valve (and, optionally, in a manner that permits the continued natural function and movement of the chordae tendineae and the native mitral valve leaflets even after the anchor component is deployed). In some embodiments, the anchor component portion and/or the deployment system includes one or more prosthetic elements that augment or substantially perform the sealing function of the native valve leaflets to mitigate the potential for valvular regurgitation during the prosthetic valve deployment process.

Figure 1:
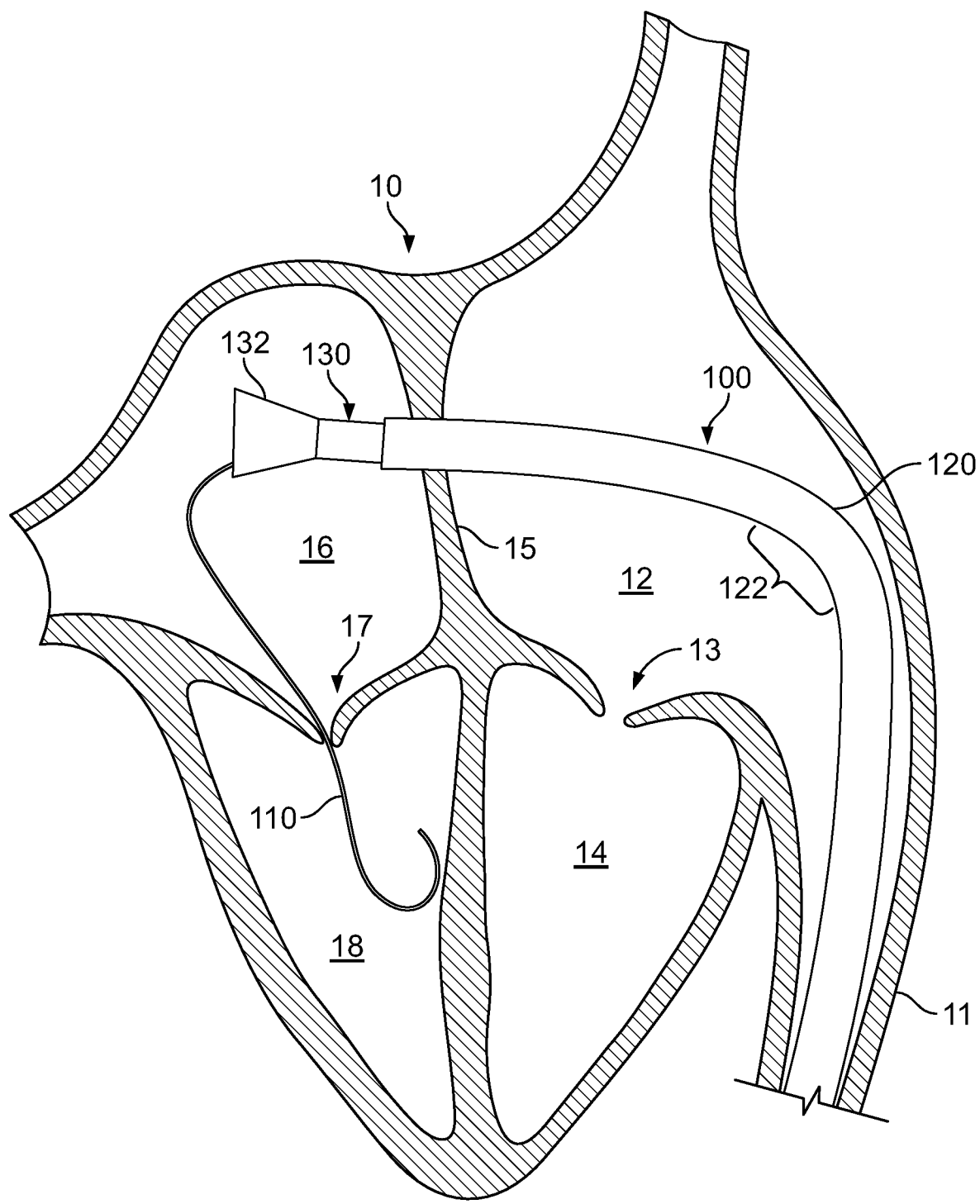
FIG. 1 shows a perspective view of a portion of a prosthetic mitral valve deployment system in a cross-sectional view of a native human heart (from a rear side of the heart), in accordance with some embodiments.

Referring to FIG. 1, an example transcatheter mitral valve delivery system 100 can be navigated through a patient's vasculature to obtain access to the patient's heart 10. The transcatheter delivery system 100 facilitates implantation of a prosthetic mitral valve in a beating heart 10 using a percutaneous, or minimally invasive technique (without open-chest surgery or open-heart surgery). For example, in some implementations the transcatheter delivery system 100 is percutaneously inserted into a femoral or iliac vein via a groin opening/incision 2 in a patient 1 (FIG. 43) using a deployment frame system 6 configured to activate and/or control the movements of various components of the transcatheter delivery system 100. In some implementations, the transcatheter delivery system 100 is used in conjunction with one or more imaging modalities such as x-ray fluoroscopy, echocardiography, magnetic resonance imaging, computed tomography (CT), and the like.

Figure 2:
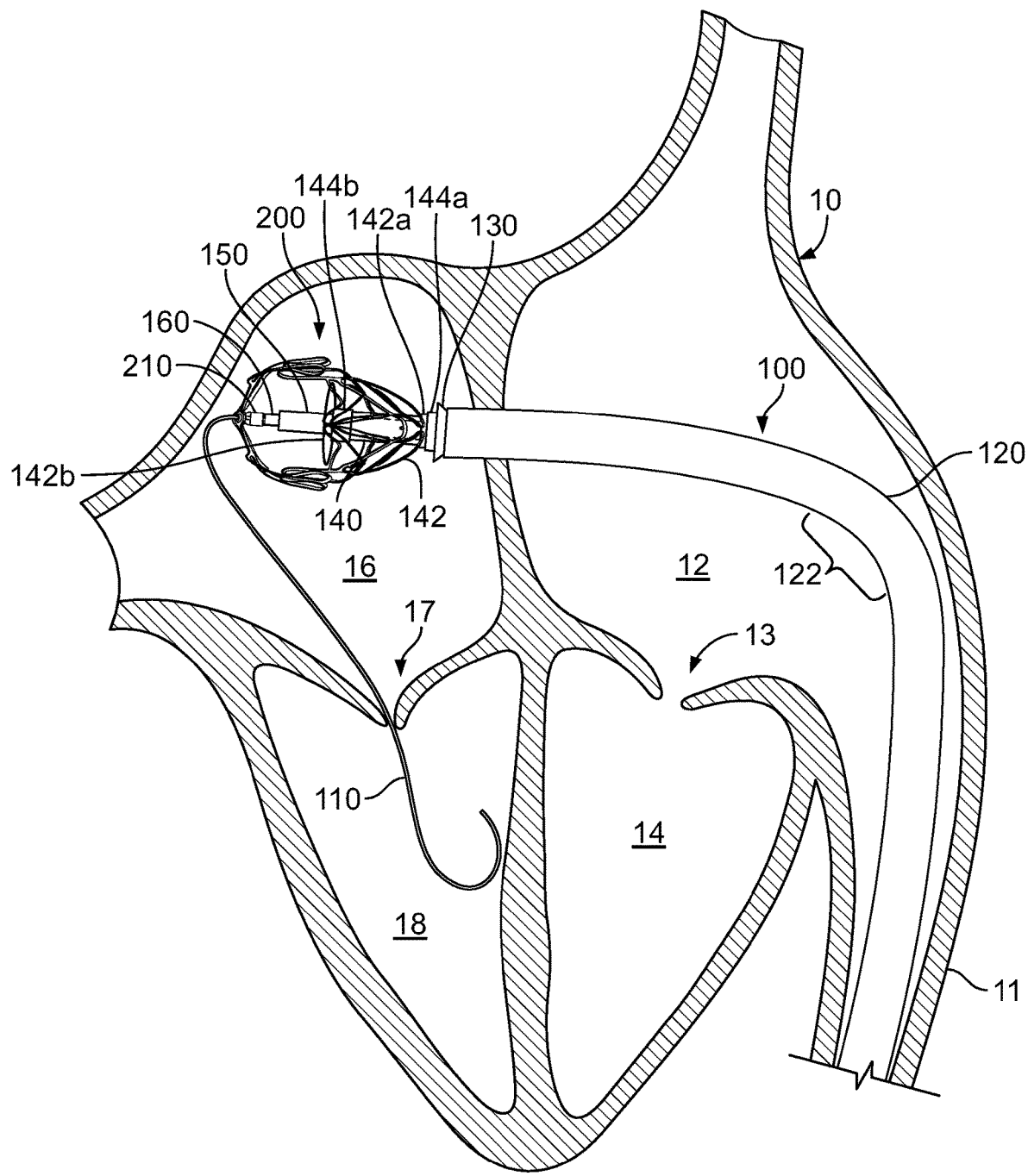
FIG. 2 shows a perspective view of a prosthetic mitral valve anchor assembly in the left atrium of the heart after the anchor assembly has emerged from an anchor delivery sheath of the deployment system of FIG. 1.
Figure 5:
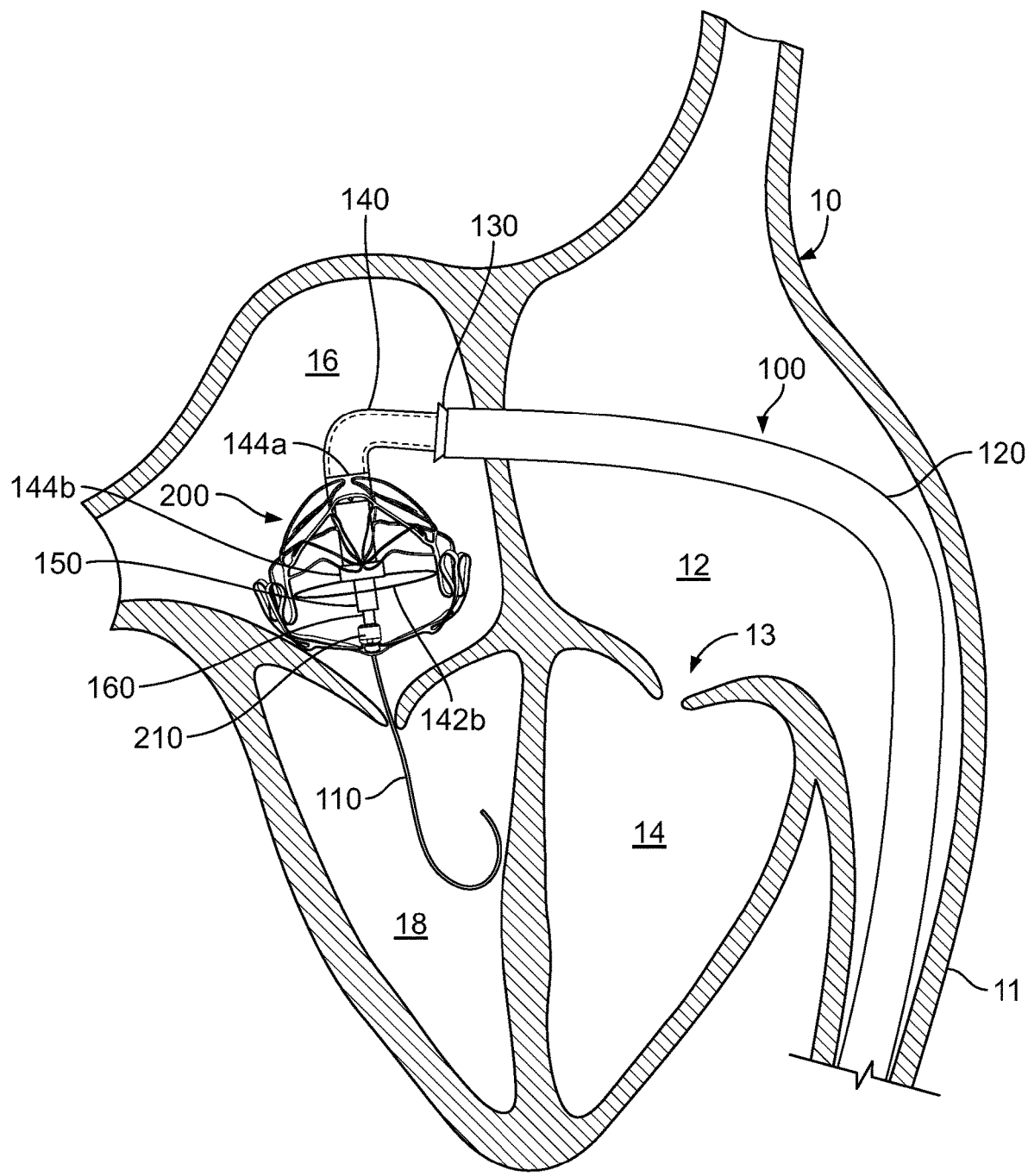
FIG. 5 shows a perspective view of the anchor assembly of FIG. 2 after being rotated/panned in the left atrium so as to orient the anchor assembly axis generally perpendicular to the native mitral valve.

The heart 10 (depicted in cross-section from a posterior perspective in FIG. 1) includes a right atrium 12, a right ventricle 14, a left atrium 16, and a left ventricle 18. A tricuspid valve 13 separates the right atrium 12 from the right ventricle 14. A mitral valve 17 separates the left atrium 16 from the left ventricle 18. An atrial septum 15 separates the right atrium 12 from the left atrium 16. An inferior vena cava 11 is confluent with the right atrium 12. It should be understood that this depiction of the heart 10 is somewhat stylized. The same is true for FIGS. 2 and 5. FIGS. 1, 2 and 5 provide general depictions of the approach to the mitral valve 17 that is used in some implementations. But, the commissural cross-sectional views of FIG. 7 and thereafter more accurately depict the orientation of the prosthetic mitral valves in relation to the heart 10.

Still referring to FIG. 1, in the depicted embodiment, the delivery system 100 includes a guidewire 110, a guide catheter 120, and an anchor delivery sheath 130. Additional components of the delivery system 100 will be described further below. The anchor delivery sheath 130 is slidably (and rotationally) disposed within a lumen of the guide catheter 120. The guidewire 110 is slidably disposed with respect to a lumen of the anchor delivery sheath 130. In this depiction, the anchor delivery sheath 130 has been partially extended relative to the guide catheter 120, allowing an optional flared portion 132 to expand outward, as described further below.

In the depicted implementation, the guidewire 110 is installed into the heart 10 prior to the other components of the delivery system 100. In some embodiments, the guidewire 110 has a diameter of about 0.035 inches (about 0.89 mm). In some embodiments, the guidewire 110 has a diameter in a range of about 0.032 inches to about 0.038 inches (about 0.8 mm to about 0.97 mm). In some embodiments, the guidewire 110 has a diameter smaller than 0.032 inches (about 0.80 mm) or larger than 0.038 inches (about 0.97 mm). In some embodiments, the guidewire 110 is made of materials such as, but not limited to, nitinol, stainless steel, high-tensile-strength stainless steel, and the like, and combinations thereof. The guidewire 110 may include various tip designs (e.g., J-tip, straight tip, etc.), tapers, coatings, covers, radiopaque (RO) markers, and other features. In some embodiments, the guidewire 110 has one or more portions with differing lateral stiffnesses, column strengths, lubricity, and/or other physical properties in comparison to other portions of the guidewire 110.

In some implementations, the guidewire 110 is percutaneously inserted into a femoral vein of the patient. The guidewire 110 is routed to the inferior vena cava 11 and into the right atrium 12. After creating an opening in the atrial septum 15 (e.g., a trans-septal puncture of the fossa ovalis or other portion of the atrial septum), the guidewire 110 is routed into the left atrium 16, and then into the left ventricle 18.

In the depicted implementation, the guide catheter 120 is installed (e.g., via the groin incision 2, refer to FIG. 43) by pushing it (and other components of delivery system 100) over the guidewire 110. In some implementations, a dilator tip is used in conjunction with the guide catheter 120 as the guide catheter 120 is advanced over the guidewire 110. Alternatively, a balloon catheter could be used as the initial dilation means. After the distal end of the guide catheter 120 reaches the left atrium 16, the dilator tip can be withdrawn.

In some embodiments, in order to navigate the guidewire 110 from the left atrium 16 to the left ventricle 18, a catheter with a curved distal tip portion (not shown) is installed over the guidewire 110 within the guide catheter 120. Also, a balloon-tipped catheter (not shown) can be installed over the guidewire 110 within the catheter with the curved distal tip portion. The curved distal tip portion of the catheter can be used to direct the balloon-tipped catheter into the left ventricle 18 (through the mitral valve 17). Such a balloon-tipped catheter can be used advantageously to avoid chordal entanglement as it is advanced through the mitral valve 17. Thereafter, the guidewire 110 can be advanced through the balloon-tipped catheter and into the left ventricle 18. In some implementations, the guidewire 110 can be installed into the heart 10 along other anatomical pathways. The guidewire 110 thereafter serves as a rail over which other components of the delivery system 100 are passed.

By making various adjustments at the proximal end of the guide catheter 120 (as described further below), a clinician can attain a desirable orientation of the guide catheter 120 in relation to the heart 10. For example, the guide catheter 120 can be rotated about its longitudinal axis so that the longitudinal axis of the distal-most tip portion of the guide catheter 120 is pointing toward the perpendicular axis of the mitral valve 17. Such rotational movement of the guide catheter 120 can be performed by the clinician using the deployment system. In addition, in some embodiments a distal end portion of the guide catheter 120 is steerable (also referred to herein as "deflectable"). Using such steering, the distal end portion of the guide catheter 120 can be deflected to navigate the patient's anatomy and/or to be positioned in relation to the patient's anatomy as desired. For example, the guide catheter 120 can be angled within the right atrium 12 to navigate the guide catheter 120 from the inferior vena cava 11 to the atrial septum 15. Accordingly, in some embodiments the guide catheter 120 may include at least one deflection zone 122. As described further below, a clinician can controllably deflect the deflection zone of the guide catheter 120 as desired.

After the guide catheter 120 is oriented within the heart 10 as desired by the clinician, in some embodiments the clinician can releasably lock the guide catheter 120 in the desired orientation. For example, in some embodiments the clinician can releasably lock the guide catheter 120 to a deployment system that is stationary in relation to the patient.

Still referring to FIG. 1, in some embodiments the guide catheter 120 has an outer diameter of about 28 Fr (about 9.3 mm), or about 30 Fr (about 10.0 mm). In some embodiments, the guide catheter 120 has an outer diameter in the range of about 26 Fr to about 34 Fr (about 8.7 mm to about 11.3 mm). In some embodiments, the guide catheter 120 has an outer diameter in the range of about 20 Fr to about 28 Fr (about 6.7 mm to about 9.3 mm).

The guide catheter 120 can comprise a tubular polymeric or metallic material. For example, in some embodiments the guide catheter 120 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the guide catheter 120 can be made from metallic materials such as, but not limited to, nitinol, stainless steel, stainless steel alloys, titanium, titanium alloys, and the like, and combinations thereof. In some embodiments, the guide catheter 120 can be made from combinations of such polymeric and metallic materials (e.g., polymer layers with metal braid, coil reinforcement, stiffening members, and the like, and combinations thereof). In some embodiments, the guide catheter 120 can comprise a slotted tube.

The example delivery system 100 also includes the anchor delivery sheath 130. In some implementations, after the guide catheter 120 is positioned with its distal end in the left atrium 16, the anchor delivery sheath 130 is installed into a lumen of the guide catheter 120 (over the guidewire 110) and advanced through the guide catheter 120. As described further below, in some embodiments the anchor delivery sheath 130 is preloaded with a prosthetic valve anchor assembly and other components of the delivery system 100.

In some embodiments, the anchor delivery sheath 130 can be made from the materials described above in reference to the guide catheter 120. In some embodiments, the anchor delivery sheath 130 has an outer diameter in the range of about 20 Fr to about 28 Fr (about 6.7 mm to about 9.3 mm). In some embodiments, the anchor delivery sheath 130 has an outer diameter in the range of about 14 Fr to about 24 Fr (about 4.7 mm to about 8.0 mm).

In the depicted embodiment, the anchor delivery sheath 130 includes a flared distal end portion 132. In some embodiments, an inverted-flare distal end portion is included. In some embodiments, no such flared distal end portion 132 is included. The flared distal end portion 132 can collapse to a lower profile when constrained within the guide catheter 120. When the flared distal end portion 132 is expressed from the guide catheter 120, the flared distal end portion 132 can self-expand to the flared shape. In some embodiments, the material of the flared distal end portion 132 includes pleats or folds, may be a continuous flared end or may be separated into sections resembling flower petals, and may include one or more resilient elements that bias the flared distal end portion 132 to assume the flared configuration in the absence of restraining forces (such as from containment within the guide catheter 120). The flared distal end portion 132 can be advantageous, for example, for recapturing (if desired) the anchor assembly within the lumen of the anchor delivery sheath 130 after the anchor assembly has been expressed from the flared distal end portion 132. In some embodiments, a distal-most portion of the flared distal end portion 132 is everted (which can serve to help facilitate recapture of the anchor delivery sheath 130). In some cases, the recapture of the anchor assembly will cause a portion of the flared distal end portion 132 to become everted.

In some embodiments, the maximum outer diameter of the flared distal end portion 132 is in a range of about 30 Fr to about 34 Fr (about 10.0 mm to about 11.3 mm). In some embodiments, the maximum outer diameter of the flared distal end portion 132 is in a range of about 32 Fr to about 44 Fr (about 10.7 mm to about 14.7 mm). In some embodiments, the maximum outer diameter of the flared distal end portion 132 is in a range of about 24 Fr to about 30 Fr (about 8.0 mm to about 10.0 mm). In some embodiments, the maximum outer diameter of the flared distal end portion 132 is less than about 24 Fr (about 8.0 mm) or greater than about 44 Fr (about 14.7 mm).

Referring to FIG. 2, additional components of the example delivery system 100 can include an anchor delivery catheter 140, a secondary steerable catheter 150, and an inner catheter 160. The anchor delivery catheter 140 is slidably disposed within a lumen of the anchor delivery sheath 130. The secondary steerable catheter 150 is slidably disposed within a lumen of the anchor delivery catheter 140. The inner catheter 160 is slidably disposed within a lumen of the secondary steerable catheter 150. The guidewire 110 is slidably disposed within a lumen of the inner catheter 160.

An anchor assembly 200 (shown without covering materials for enhanced visibility) is releasably attached to the inner catheter 160 and is, in effect, slidably disposed on the guidewire 110. As described further below, the components of the delivery system 100 can be individually or jointly manipulated by a clinician operator to control the position and orientation of the anchor assembly 200 during the deployment of the anchor assembly 200. In some embodiments, the inner catheter 160 has a filar construct to advantageously configure the inner catheter 160 to transmit torsion forces. In some implementations, a deployment frame system (such as the example deployment frame system in FIG. 43 described below) is used to initiate and/or control the movements of various components of the transcatheter delivery system 100.

In a preferred implementation of delivery system 100, the anchor delivery catheter 140, the secondary steerable catheter 150, the inner catheter 160, and the anchor assembly 200 are loaded into the anchor delivery sheath 130 prior to the advancement of the anchor delivery sheath 130 into the guide catheter 120 as shown in FIG. 1. That is, in a preferred implementation the anchor delivery catheter 140, the secondary steerable catheter 150, the inner catheter 160, and/or the anchor assembly 200 are already installed in the anchor delivery sheath 130 as the anchor delivery sheath 130 is distally advanced into the guide catheter 120 to attain the arrangement shown in FIG. 1. Then the anchor delivery sheath 130 is individually pulled back (proximally) to reveal the anchor delivery catheter 140, the secondary steerable catheter 150, the inner catheter 160, and/or the anchor assembly 200 as shown in FIG. 2. The anchor assembly 200 may also be at least partially expanded. In some such implementations, the anchor delivery catheter 140, the secondary steerable catheter 150, the inner catheter 160, and/or the anchor assembly 200 are loaded into the anchor delivery sheath 130 in desired relative rotational orientations (i.e., rotational orientations about the longitudinal axis of the delivery system 100). In other implementations, one or more of the anchor delivery catheter 140, the secondary steerable catheter 150, the inner catheter 160, and the anchor assembly 200 are distally advanced into the anchor delivery sheath 130 after the anchor delivery sheath 130 has been advanced into the guide catheter 120 to attain the arrangement shown in FIG. 1.

The inner catheter 160 is releasably coupled with a hub 210 of the anchor assembly 200. In some such embodiments, the inner catheter 160 has a threaded distal tip portion 162 (FIG. 3) that threadably engages with a complementary threaded portion of the hub 210. In some embodiments, as described further below, the inner catheter 160 is also releasably coupled with a SAM containment member 212 (refer, for example, to FIGS. 8 and 19) of the anchor assembly 200. For example, in some embodiments the threaded distal tip portion 162 of the inner catheter 160 is threadably engaged with a complementary threaded eyelet 214 (e.g., FIGS. 16 and 17) of the SAM containment member 212. When a clinician operator desires to uncouple the inner catheter 160 from the SAM containment member 212 and/or the hub 210, the clinician can apply a torque to the inner catheter 160 to unscrew the threaded distal tip portion 162 from the eyelet 214 and/or the hub 210. In some embodiments, the inner catheter 160 is a filar construct so as to configure the inner catheter 160 to transmit a torque to facilitate uncoupling the inner catheter 160 from the SAM containment member 212 and/or the hub 210. In some embodiments, other types of mechanisms are used to releasably couple the delivery system 100 to one or more portions of the anchor assembly 200.

One or more portions of the anchor assembly 200 can also be releasably coupled to one or more catheters of the delivery system 100 by one or more control wires. The one or more control wires can be used to control the anchor assembly 200 (e.g., to control the configuration of the anchor assembly 200). For example, the one or more control wires can be used for controlling the diametrical expansion of a self-expanding anchor assembly 200 and/or for controlling the deployment of particular features of the anchor assembly 200. In the depicted embodiment, a proximal portion of the anchor assembly 200 is releasably coupled to the anchor delivery catheter 140 by a proximal control wire 142a, and a mid-body portion of the anchor assembly 200 is releasably coupled to the anchor delivery catheter 140 by a mid-body control wire 142b.

Figure 3:
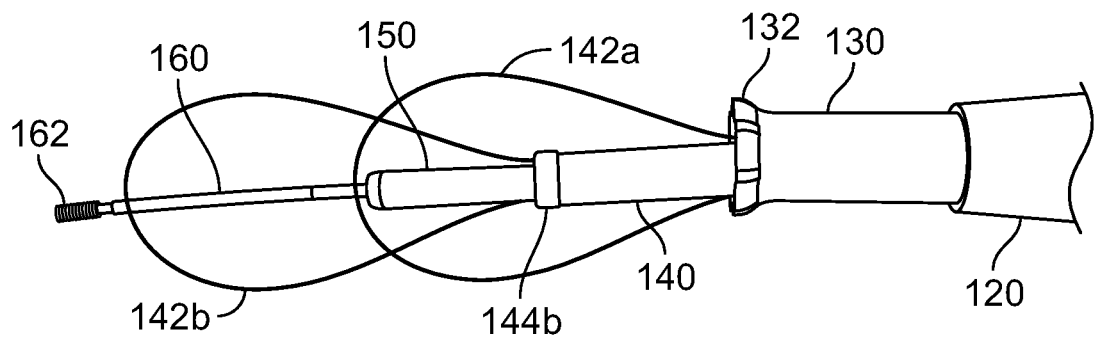
FIG. 3 shows a distal end portion of some components of the deployment system of FIG. 1, including two wires for controlling the diametric expansion of the anchor assembly of FIG. 2.
Figure 4:
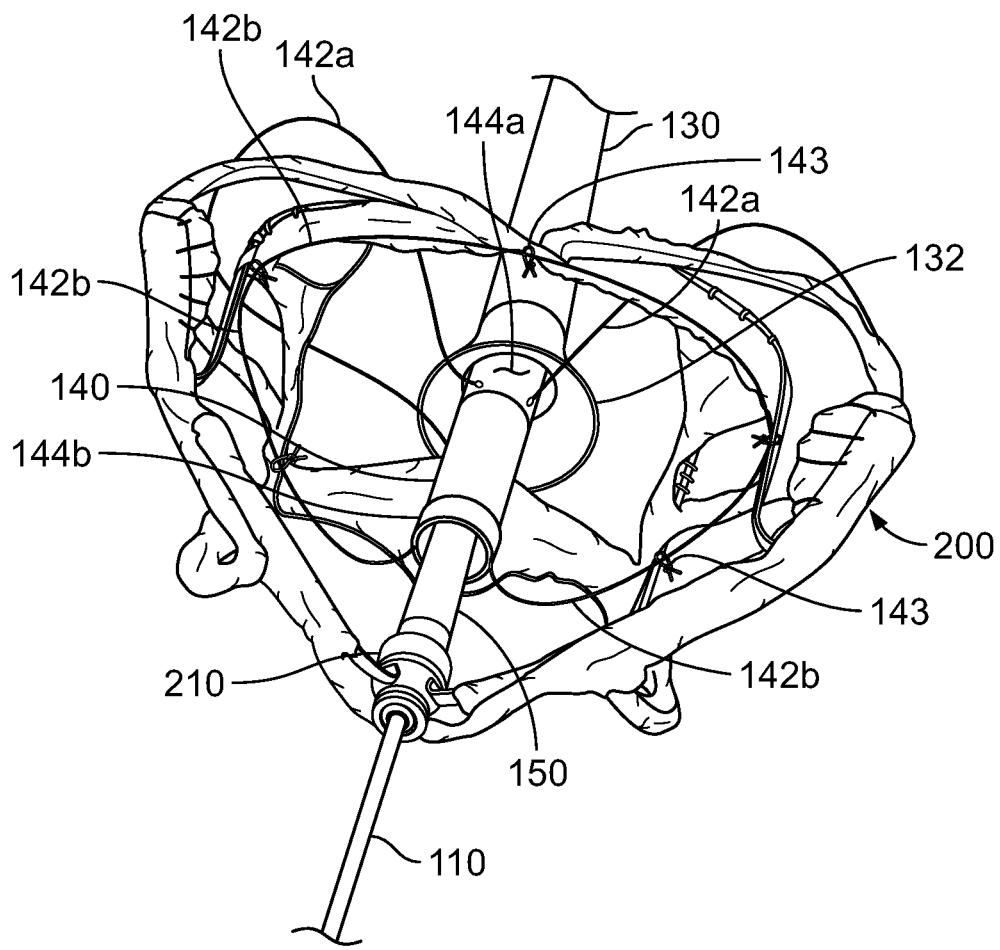
FIG. 4 shows a perspective view of the distal end portion of the deployment system as shown in FIG. 3 in engagement with the anchor assembly of FIG. 2.

Referring also to FIGS. 3 and 4, in the depicted embodiment the proximal control wire 142a emerges from and reenters into the anchor delivery catheter 140 at a proximal collar 144a that is integral with the anchor delivery catheter 140, and the distal control wire 142b emerges from and reenters into the anchor delivery catheter 140 at a distal collar 144b that is integral with the anchor delivery catheter 140. In some embodiments, the control wires 142a and 142b pass through lumens in the wall of the anchor delivery catheter 140, and travel proximally to the deployment control system (e.g., the example deployment frame system shown in FIG. 43). The two ends of each of the control wires 142a and 142b can be terminated at the deployment control system. At such a deployment control system, the tension on the control wires 142a and 142b can be manipulated by a clinician to control the configuration of the anchor assembly 200. In this example, by tightening the control wires 142a and/or 142b, the anchor assembly 200 will be diametrically contracted, and by loosening the control wires 142a and/or 142b, the anchor assembly 200 will be permitted to diametrically self-expand (for example, so that each control wire 142a and 142b can be operated somewhat similar to an adjustable lasso to control expansion of different portions of the anchor assembly at different stages). When the clinician is satisfied with the deployment orientation of the anchor assembly 200, the control wires 142a and 142b can be decoupled from the anchor assembly 200 by the clinician. To do so, the clinician can release one end of the control wire 142a and/or 142b and pull on the other end so that the control wire 142a and/or 142b becomes disengaged with the anchor assembly 200.

FIG. 4 shows how the control wires 142a and 142b can be releasably coupled with the anchor assembly 200 in some embodiments. It should be understood that this is merely one exemplary control wire coupling arrangement and various other arrangements for coupling one or more control wires to the anchor assembly 200 are also envisioned within the scope of this disclosure. Various types of attachment elements can be used to releasably couple the control wires 142a and 142b to the anchor assembly 200. In the depicted embodiment, suture loops 143 are used as the attachment elements. The suture loops 143 can be constructed of materials such as, but not limited to, ultra-high molecular weight polyethylene, nylon, polypropylene, polybutester, and the like. In some embodiments, two suture loops 143 are used in each location to provide redundancy. The suture loops 143 may be coupled with eyelets on the anchor assembly 200 in some cases. In some embodiments, other types of attachment elements such as, but not limited to, eyelets, grommets, rings, clips, pins, fabric portions, and/or the like, are used as attachment elements.

In the depicted embodiment, the proximal control wire 142a is releasably coupled with attachment elements associated with structural features located at the proximal end of the anchor assembly 200. For example, the proximal control wire 142a is releasably coupled with attachment elements of three arched atrial holding features 240a, 240b, and 240c (e.g., refer to FIGS. 18-21) and three frame lobes 250a, 250b, and 250c (e.g., refer to FIGS. 18-21) of the anchor assembly 200. That is, the proximal control wire 142a emerges from the anchor delivery catheter 140 at the proximal collar 144a, passes through the attachment elements of the three arched atrial holding features 240a, 240b, and 240c, and the three frame lobes 250a, 250b, and 250c, and reenters the anchor delivery catheter 140 at the proximal collar 144a. By applying tension to the proximal control wire 142a, the three arched atrial holding features 240a, 240b, and 240c, and the three frame lobes 250a, 250b, and 250c can be diametrically drawn inward towards the anchor delivery catheter 140. In the arrangement depicted in FIG. 2, for example, the three arched atrial holding features 240a, 240b, and 240c, and the three frame lobes 250a, 250b, and 250c are drawn in very closely to the anchor delivery catheter 140.

In the depicted embodiment, the mid-body control wire 142b is releasably coupled with attachment elements associated with structural features of the anchor assembly 200 located at the longitudinal middle region of the anchor assembly 200. For example, the mid-body control wire 142b is releasably coupled with attachment elements of four inter-annular connections 270a, 270b, 270c, and 270d (e.g., refer to FIGS. 18-21) and a mid-body portion of the supra-annular ring 250 of the anchor assembly 200. That is, the mid-body control wire 142b emerges from the anchor delivery catheter 140 at the distal collar 144b, passes through the attachment elements of the four inter-annular connections 270a, 270b, 270c, and 270d, and the mid-body portion of the supra-annular ring 250, and reenters the anchor delivery catheter 140 at the distal collar 144b. By applying tension to the mid-body control wire 142b, the four inter-annular connections 270a, 270b, 270c, and 270d, and the mid-body portion of the supra-annular ring 250 can be diametrically drawn inward towards the anchor delivery catheter 140. In the arrangement depicted in FIG. 2, the four inter-annular connections 270a, 270b, 270c, and 270d, and the mid-body portion of the supra-annular ring 250 are drawn in toward the anchor delivery catheter 140 such that the diameter of the anchor assembly 200 is less than the fully expanded diameter.

Diametric control of the anchor assembly 200 by manipulation of the tension of the mid-body control wire 142b can be advantageously utilized by a clinician during the deployment of the anchor assembly 200. For example, as described further below, the steps of advancing the anchor assembly 200 through the annulus of the native mitral valve and seating anchor feet 220a, 220b, 220c, and 220d (e.g., refer to FIGS. 18-21) in the sub-annular gutter 19 (FIG. 12) can be facilitated using the diametric control afforded by the mid-body control wire 142b.

While the depicted embodiment includes two control wires 142a and 142b, in some embodiments one, three, four, five, or more than five control wires are included. A clinician can separately control the two control wires 142a and 142b. For example, in some embodiments the mid-body control wire 142b may be partially or fully loosened while the proximal control wire 142a is maintained in a state of full tension. In some implementations, a deployment frame system (such as the example deployment frame system of FIG. 43 described below) is used to control the tension and movements of the two control wires 142a and 142b.

Still referring to FIG. 2, while the components of the delivery system 100 and the anchor assembly 200 are depicted in particular relative orientations and arrangements, it should be understood that the depictions are non-limiting. For example, in some implementations of the deployment process the distal tip of the secondary deflectable catheter 150 may always be, or may sometimes be, abutted to the hub 210 of the anchor assembly 200. Further, in some implementations of the deployment process the distal tip of the anchor delivery catheter 140 may always be, or may sometimes be, positioned within the interior of the anchor assembly 200. In some implementations, a deployment frame system (such as the example deployment frame system of FIG. 43 described below) is used to control such relative arrangements and movements of the anchor delivery catheter 140 and secondary deflectable catheter 150 in relation to the anchor assembly 200, for example.

In some embodiments, the position of the anchor assembly 200 can be controlled by manipulating the relative positions of the inner catheter 160 and/or the anchor delivery catheter 140. For example, in the depicted embodiment the anchor assembly 200 can be expressed out from the anchor delivery sheath 130 (as shown in FIG. 2) by moving the inner catheter 160 and/or the anchor delivery catheter 140 distally in relation to the anchor delivery sheath 130. In some implementations, the expression of the anchor assembly 200 is caused by proximally pulling back the anchor delivery sheath 130 while generally maintaining the positions of the inner catheter 160 and/or the anchor delivery catheter 140. In some implementations, the expression of the anchor assembly 200 is caused by a combination of proximally pulling back the anchor delivery sheath 130 while distally extending the positions of the inner catheter 160 and/or the anchor delivery catheter 140.

As the anchor assembly 200 emerges from the confines of the anchor delivery sheath 130, the anchor assembly 200 may expand from a low-profile delivery configuration to an at least partially expanded configuration (for example, a partially expanded condition, as shown in FIG. 2, that is less that its fully expanded condition as described in more detail below). In addition to control by manipulation of the mid-body control wire 142b, the extent of expansion of the anchor assembly 200 can also be at least partially controlled by the relative positioning of the anchor delivery catheter 140 in relation to the inner catheter 160. For instance, as the anchor delivery catheter 140 is moved proximally in relation to the inner catheter 160, the anchor assembly 200 is axially elongated and radially contracted. Conversely, as the anchor delivery catheter 140 is moved distally in relation to the inner catheter 160, the anchor assembly 200 is axially shortened and radially expanded. In some implementations, this control of the radial size of the anchor assembly 200 is used by a clinician during the process of deploying the anchor assembly 200 within the native mitral valve 17, as described further below. As described above, the one or more control wires 142a and 142b can also be used to control diametrical expansion of the anchor assembly 200 (without changing the relative distance of the anchor delivery catheter 140 in relation to the inner catheter 160).

Figure 37:
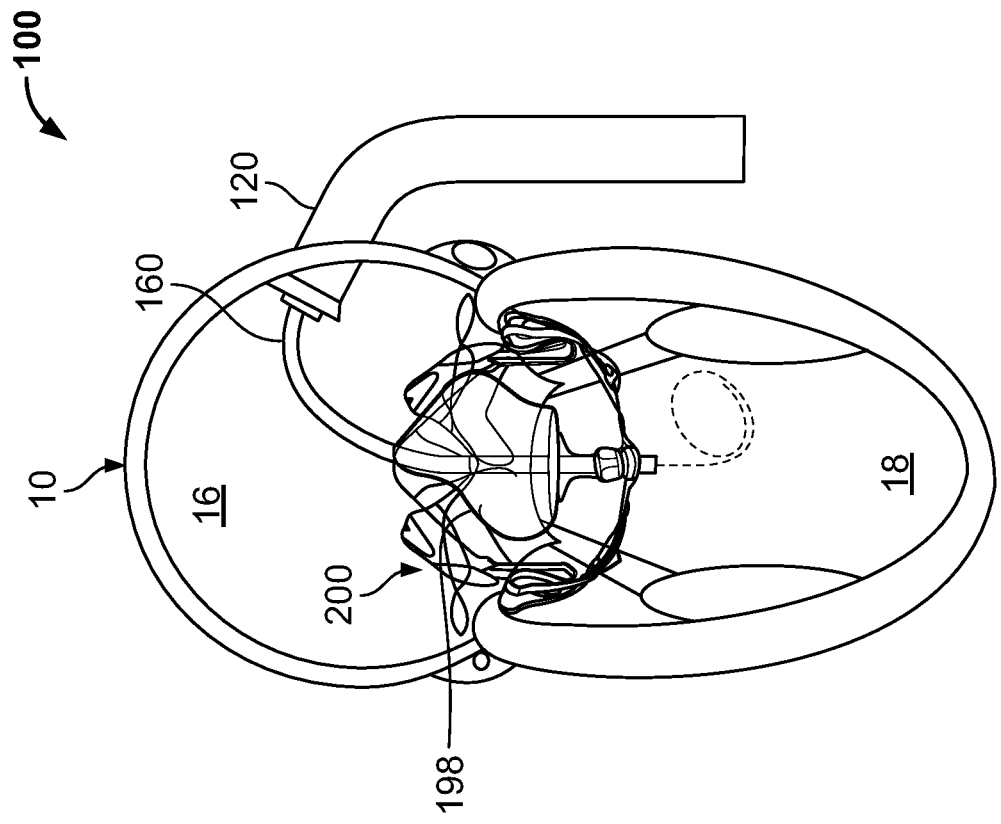
FIG. 37 shows a commissural cross-sectional view of a heart with the anchor assembly of FIG. 7 being deployed within the native mitral valve.

It should be understood that the prosthetic mitral valves provided herein are comprised of an anchor assembly 200 and a separate valve assembly (e.g., refer to FIG. 37). The anchor assembly 200 is deployed to an arrangement interfacing within the native mitral valve 17 prior to deployment of the valve assembly. Said differently, after implanting the anchor assembly 200 within the native mitral valve 17, the valve assembly can then be deployed within the anchor assembly 200 and within the native mitral valve 17 (as described further below). Therefore, it can be said that the prosthetic mitral valves provided herein are deployed using a staged implantation method. That is, the anchor assembly 200 is deployed in one stage, and the valve assembly is deployed in a subsequent stage. In some embodiments, as described further below, the SAM containment member 212 is also deployed as part of the deployment method. In some implementations, the deployment of the valve assembly takes place right after the deployment of the anchor assembly 200 (e.g., during the same medical procedure). In some implementations, the deployment of the valve assembly takes place hours, days, weeks, or even months after the deployment of the anchor assembly 200 (e.g., during a subsequent medical procedure).

The staged implantation method of the prosthetic mitral valves provided herein is facilitated by the fact that when the anchor assembly 200 itself is implanted within the native mitral valve 17, the native mitral valve 17 continues to function essentially as before the implantation of the anchor assembly 200 without a significant impact on cardiovascular physiology. That is the case because, as described further below, the anchor assembly 200 interfaces and anchors within structural aspects of the native mitral valve 17 without substantially interfering with the leaflets or chordae tendineae of the native mitral valve 17.

Still referring to FIG. 2, in the depicted arrangement the distal end portion of the secondary steerable catheter 150 is located at least partially internally within the anchor assembly 200. The secondary steerable catheter 150 can be manipulated by a clinician operator to reversibly bend (deflect) the distal end portion of the secondary steerable catheter 150. As the secondary steerable catheter 150 is bent by the clinician, other components of the delivery system 100 may deflect along with the secondary steerable catheter 150. For example, portions of one or more of the inner catheter 160 and the anchor delivery catheter 140 may bend in response to the bending of the deflectable catheter 150. Because the anchor assembly 200 is coupled to the inner catheter 160 and the anchor delivery catheter 140, the anchor assembly 200 can, in turn, be pivoted or "panned" by bending the secondary steerable catheter 150.

Referring to FIG. 5, as described above, in some embodiments the secondary steerable catheter 150 can be articulated (also referred to as "steered," "deflected," "bent," "curved," and the like) to orient the anchor assembly 200 in relation to the mitral valve 17 as desired. That is, in some embodiments the secondary steerable catheter 150 has one or more deflection zones at a distal end portion of the secondary steerable catheter 150. For example, in the depicted embodiment the secondary steerable catheter 150 has two deflection zones 152 and 154 (refer to FIG. 7) at the distal end portion of the secondary steerable catheter 150. In some embodiments, the two deflection zones 152 and 154 allow for deflection of the distal end portion of the secondary steerable catheter 150 within two separate and distinct planes. For example, in the depicted embodiment deflection zone 152 allows for deflection of the distal end portion of the secondary steerable catheter 150 generally within the plane of FIGS. 1, 2, and 5, while deflection zone 154 allows for deflection of the distal end portion of the secondary steerable catheter 150 generally orthogonal to the plane of FIGS. 1, 2, and 5. In some implementations, a deployment frame system (such as the example deployment frame system of FIG. 43 described below) is used to initiate and control such deflection of the secondary steerable catheter 150, including deflection of the distal end portion of the secondary steerable catheter 150 within two separate and distinct planes, individually.

In some implementations, it is desirable to orient (e.g., laterally pivot, pan, etc.) the anchor assembly 200 within the atrium 16 so that the longitudinal axis of the anchor assembly 200 is generally perpendicular to the native mitral valve 17, and coaxial with the native mitral valve 17 (e.g., to center the anchor assembly 200 with the line or coaptation of the mitral valve 17). The orienting of the partially or fully expanded anchor assembly 200 within the atrium 16 may be advantageous versus having to orient the anchor assembly 200 while it is still constrained within a delivery sheath, as the latter assembly is a relatively large and stiff catheter assembly.

In some implementations, the anchor assembly 200 within the atrium 16 can be additionally, or alternatively, oriented in relation to the native mitral valve 17 by rotating the guide catheter 120 about its longitudinal axis. Such a rotation of the guide catheter 120 about its longitudinal axis can result in a directional adjustment of the longitudinal axis of the distal tip portion of the guide catheter 120. That is, rotation of the guide catheter 120 about its longitudinal axis can result in pointing the distal tip portion of the guide catheter 120 (and the components of the delivery system 100) in a desired direction within the atrium 16. In some implementations, a deployment frame system is used to initiate and control such rotation of the guide catheter 120 about its longitudinal axis.

In some implementations, the relative rotational alignment of the anchor assembly 200 in relation to the mitral valve 17 can be adjusted as desired in preparation for engaging the anchor assembly 200 with the native mitral valve 17. For example, in some implementations the anchor assembly 200 can be rotated about its longitudinal axis by rotating the inner catheter 160 and the anchor delivery catheter 140 generally in unison, while keeping the secondary steerable catheter 150 essentially stationary. In some implementations, a deployment frame system (such as the example deployment frame systems described below) is used to initiate and control such rotation of the anchor assembly 200 about its longitudinal axis.

In preparation for engaging the anchor assembly 200 with the native mitral valve 17, the clinician operator may manipulate the radial size of the anchor frame 200 so that the anchor frame 200 can be passed through the native mitral valve 17 without damaging the native mitral valve 17. For example, the clinician can diametrically expand or retract one or more portions of the anchor assembly 200 by manipulation of the mid-body control wire 142b. Alternatively, or additionally, the clinician can move the anchor delivery catheter 140 proximally in relation to the inner catheter 160 to radially contract the anchor assembly 200. With the anchor assembly 200 configured in a desired diametrical size, and appropriately aligned with the mitral valve 17, the anchor frame 200 can be safely passed through the native mitral valve 17 without damaging the native mitral valve 17 and/or entangling chordae tendineae of the mitral valve 17. Moreover, by controlling the diametrical size of the anchor assembly 200 to just slightly less than the size of the annulus of the mitral valve 17, an advantageous natural centering of the anchor assembly 200 can occur as the sub-annular portions of the anchor assembly 200 are advanced through the mitral valve 17.

Figure 7:
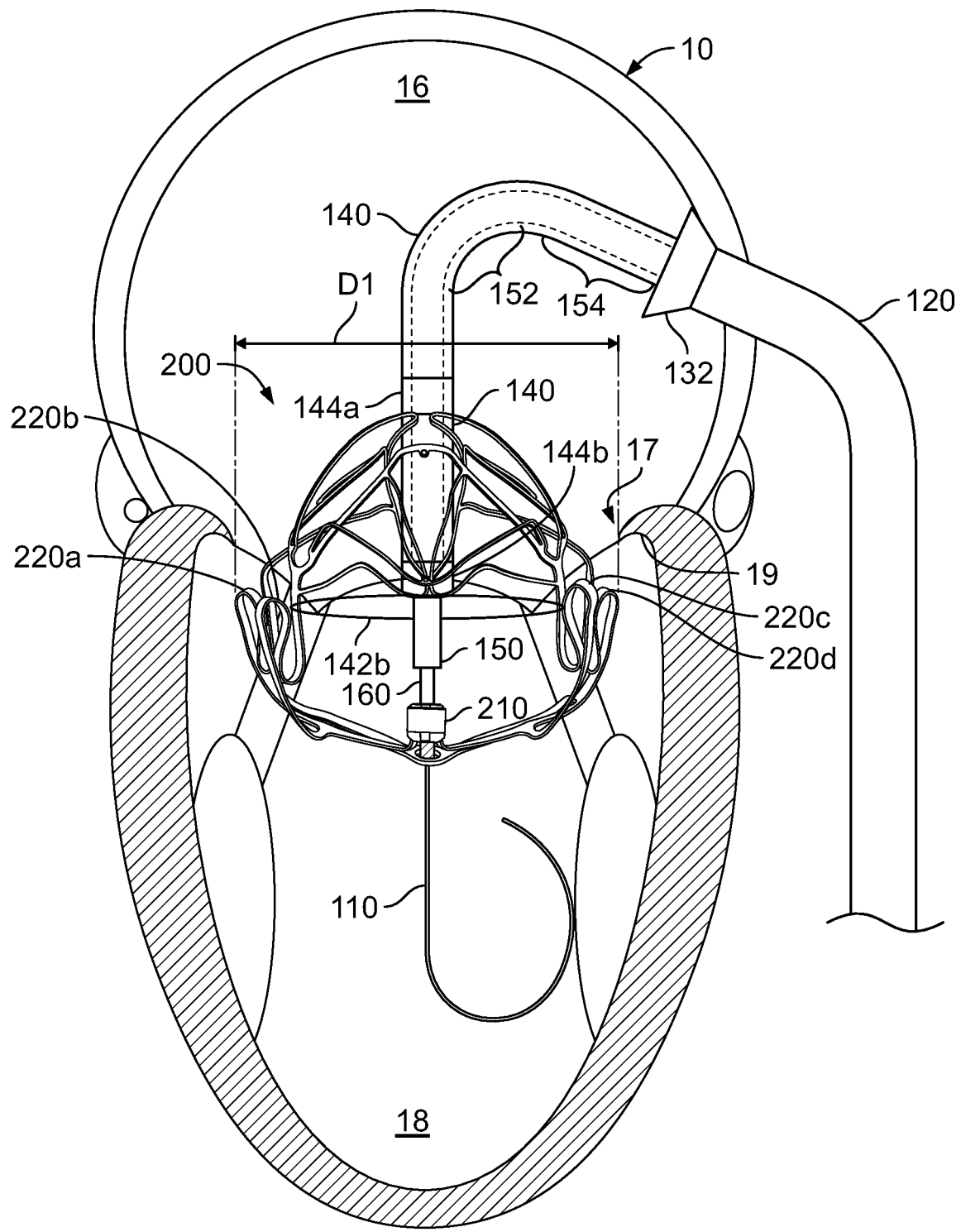
FIG. 7 shows a perspective view in a commissural cross-sectional view of the heart (from the left side of the heart) of the anchor assembly of FIG. 2 after being partially advanced through the native mitral valve so as to position projections of the anchor assembly below an annulus of the native mitral valve.

Referring to FIG. 7, a commissural cross-sectional view of the heart 10 provides another perspective of the anchor assembly 200 in relation to the native mitral valve 17. This commissural cross-sectional view of the heart 10 is a cross-sectional view taken through the mitral valve 17 along a plane through the left atrium 16 and left ventricle 18 that is parallel to the line that intersects the two commissures of the mitral valve. In the following FIGS. 8-11 and 25-30, the commissural cross-sectional view of the heart 10 will be used to describe the delivery system 100 and methods for deploying the prosthetic mitral valves provided herein. The view in FIGS. 7-11 and 25-30 is slightly tilted so that better visualization of the anchor assembly 200 is provided.

While the secondary steerable catheter 150 is retained in its bent (deflected) configuration as described in reference to FIG. 5, the inner catheter 160 and the anchor delivery catheter 140 can be simultaneously advanced. Because the inner catheter 160 is releasably coupled to the hub 210 of the anchor assembly 200, and because the anchor delivery catheter 140 is releasably coupled to the proximal end and the mid-body region of the anchor assembly 200 via the control wires 142a and 142b, generally simultaneous advancement of the inner catheter 160 and the anchor delivery catheter 140 results in advancement of the anchor assembly 200.

In preparation for the advancement of the distal portions of the anchor assembly 200 through the annulus of the mitral valve 17, the mid-body control wire 142b can be manipulated to adjust a mid-body diameter D1 of the anchor assembly 200 to a desired size. For example, in some implementations it is desirable to adjust the mid-body diameter D1 to size that is slightly smaller than the size of the annulus of the mitral valve 17. In such a case, while advancing the distal portions of the anchor assembly 200 through the annulus of the mitral valve 17, a self-centering of the anchor assembly 200 in relation to the mitral valve 17 may naturally occur.

As depicted, the anchor assembly 200 is advanced such that the distal end portions of anchor assembly 200 are positioned within the left ventricle 18 while the proximal end portions of the anchor assembly 200 remain positioned within the left atrium 16. Hence, some portions of the anchor assembly 200 are on each side of the native mitral valve 17. Said differently, the deployed anchor assembly 200 includes supra-annular portions and sub-annular portions.

In the depicted embodiment, the anchor assembly 200 includes four anchor feet: a lateral anterior foot 220a, a lateral posterior foot 220b, a medial posterior foot 220c, and a medial anterior foot 220d (refer also to FIGS. 18-21). In some embodiments, fewer or more anchor feet may be included (e.g., two, three, five, six, or more than six). In some embodiments, the anchor feet 220a, 220b, 220c, and 220d are portions of the anchor assembly 200 that are configured for contact with a sub-annular gutter 19 (also refer to FIG. 12) of the native mitral valve 17, without penetrating tissue of the native mitral valve 17. Accordingly, the anchor feet 220a, 220b, 220c, and 220d have atraumatic surfaces that are generally comparable to feet. However, in some embodiments one or more of the anchor feet 220a, 220b, 220c, and 220d are configured to penetrate tissue and may have anchor features such as barbs, coils, hooks, and the like.

In the arrangement of FIG. 7, the anchor feet 220a, 220b, 220c, and 220d are positioned below the sub-annular gutter 19. In this arrangement then, the mid-body diameter D1 of the anchor assembly 200 can thereafter be increased to align the anchor feet 220a, 220b, 220c, and 220d with the sub-annular gutter 19. For example, in some embodiments the mid-body control wire 142b positioned on or around the mid-body portion of the anchor assembly 200 can be manipulated (e.g., slackened) to allow radial self-expansion of the anchor assembly 200, to align the anchor feet 220a, 220b, 220c, and 220d with the sub-annular gutter 19. Alternatively, or additionally, in some embodiments the clinician can move the anchor delivery catheter 140 distally in relation to the inner catheter 160 to radially expand the anchor assembly 200 to align the anchor feet 220a, 220b, 220c, and 220d with the sub-annular gutter 19. Such alignment can be performed in preparation for seating the anchor feet 220a, 220b, 220c, and 220d within the sub-annular gutter 19.

Figure 8:
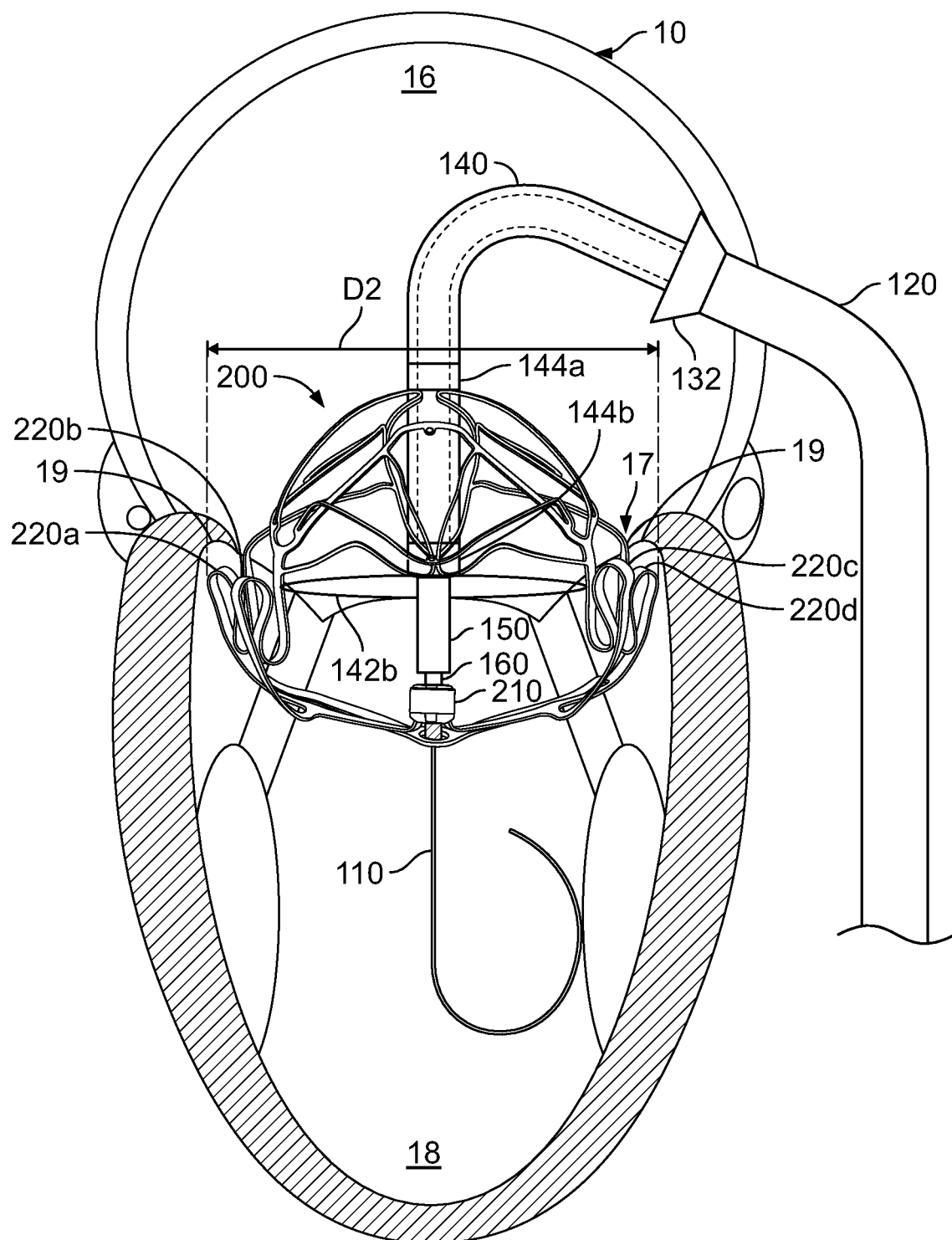
FIG. 8 shows a perspective view of the anchor assembly of FIG. 7 after being diametrically expanded to align the projections of the anchor assembly with a sub-annular gutter of the native mitral valve.

Referring to FIG. 8, the anchor feet 220a, 220b, 220c, and 220d are positioned below the sub-annular gutter 19. In this position, the anchor feet 220a, 220b, 220c, and 220d are positioned under the systolic and diastolic excursions of the leaflets of the native mitral valve 17.

With the anchor feet 220a, 220b, 220c, and 220d positioned below the sub-annular gutter 19, the anchor feet 220a, 220b, 220c, and 220d can be aligned with the sub-annular gutter 19 in preparation for seating the anchor feet 220a, 220b, 220c, and 220d within the sub-annular gutter 19. For example, to align the anchor feet 220a, 220b, 220c, and 220d with the sub-annular gutter 19, in some implementations tension from the mid-body control wire 142b can be relieved by the clinician to allow the mid-body diameter to expand from D1 (FIG. 7) to D2. When the anchor assembly 200 has a mid-body diameter D2, the anchor feet 220a, 220b, 220c, and 220d are posed in diametrical positions for seating within the sub-annular gutter 19.

Figure 9:
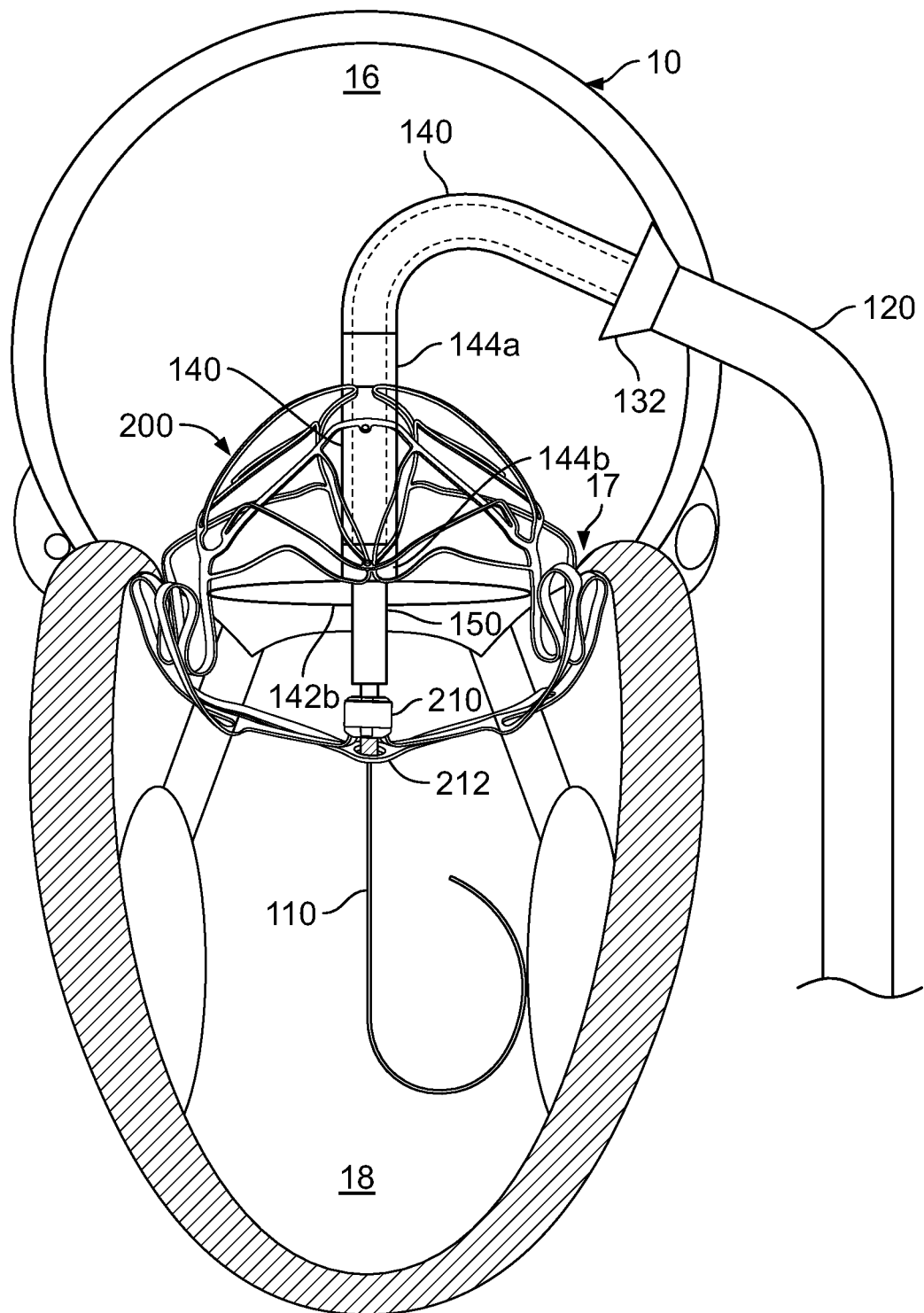
FIG. 9 shows a perspective view of the anchor assembly of FIG. 8 after being retracted so as to position the projections of the anchor assembly in the sub-annular gutter of the native mitral valve.

Referring to FIG. 9, the inner catheter 160 and the anchor delivery catheter 140 can be simultaneously retracted while maintaining the secondary steerable catheter 150 and the guide catheter 120 in fixed positions. As a result, the anchor feet 220a, 220b, 220c, and 220d become seated in the sub-annular gutter 19. As described further below, simultaneous movement of two or more components of the delivery system 100 (e.g., the inner catheter 160 in conjunction with the anchor delivery catheter 140, while maintaining the secondary steerable catheter 150 and the guide catheter 120 in fixed positions) can be initiated and controlled using a deployment frame system (such as the example deployment frame system of FIG. 43 described below).

With the anchor feet 220a, 220b, 220c, and 220d seated in the sub-annular gutter 19, the anchor feet 220a, 220b, 220c, and 220d are positioned under the systolic and diastolic excursions of the leaflets of the native mitral valve 17, and the other structures of the anchor assembly 200 do not inhibit the movements of the leaflets. Therefore, with the anchor assembly 200 coupled to the structures of the mitral valve 17 as described, the mitral valve 17 can continue to function as it did before the placement of the anchor assembly 200. In addition, the manner in which the anchor assembly 200 interfaces with the native mitral valve 17 does not result in deformation of the native mitral valve 17. With the SAM containment member 212 in its pre-deployed configuration, the SAM containment member 212 does not affect the natural function of the native mitral valve 17. Therefore, the native mitral valve 17 can continue to function as it did before the placement of the anchor assembly 200.

Figure 10:
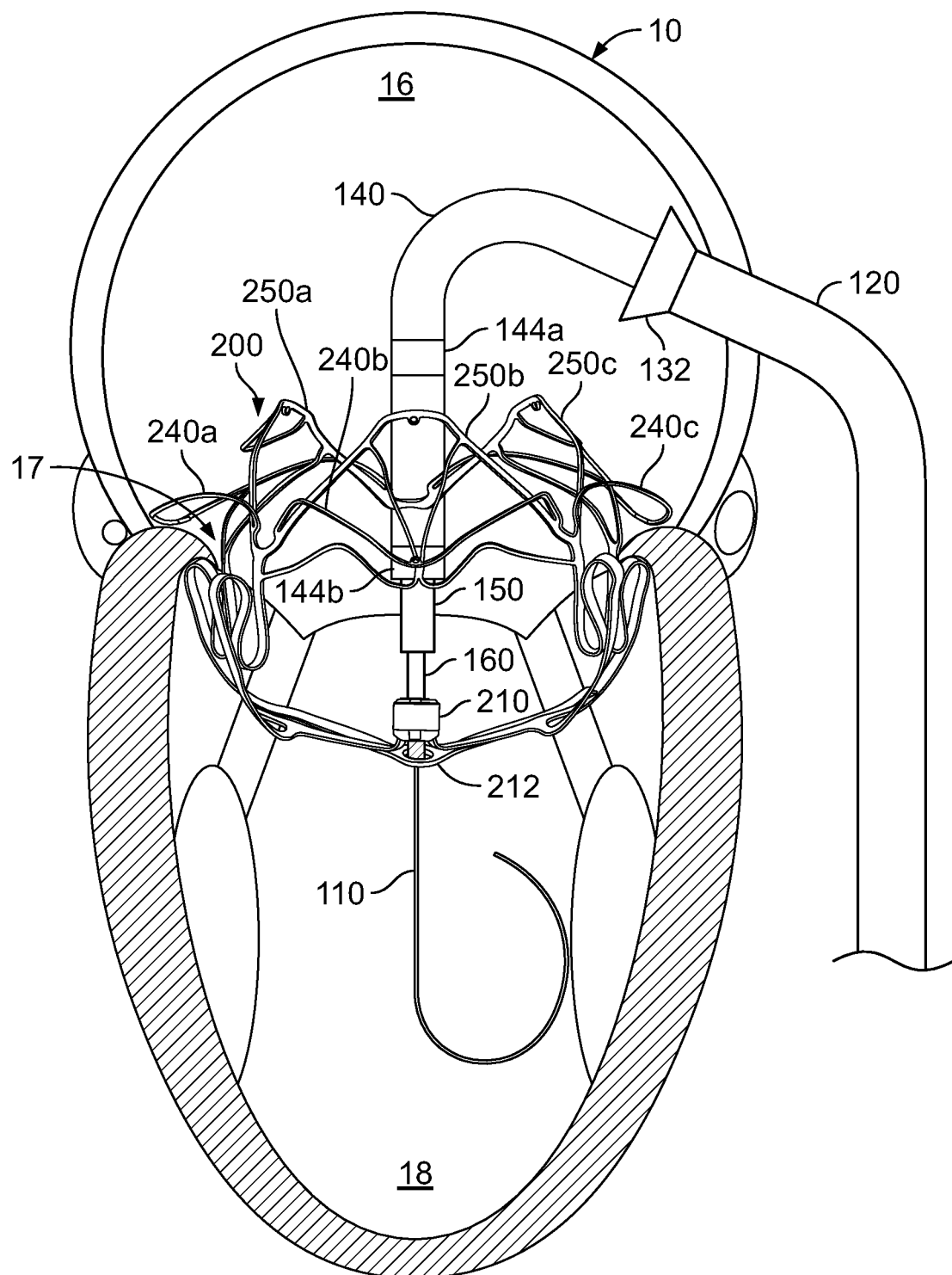
FIG. 10 shows a perspective view of the anchor assembly of FIG. 7 after the release and retraction of the control wires of the deployment system.

Referring to FIG. 10, with the anchor assembly 200 engaged within the native mitral valve 17, components of the delivery system 100 can be uncoupled from the anchor assembly 200. For example, the one or more control wires 142a and 142b (FIGS. 2-5 and 7-9) can be uncoupled from the anchor assembly 200 (e.g., from the mid-body and proximal end portions of the anchor assembly 200 in some embodiments). As described further below, in some embodiments the frame members of the anchor assembly 200 can be made of an elastic or a super-elastic material with shape memory such that portions of the anchor assembly 200 self-expand/deploy to intended orientations in the absence of constraining forces, such as constraining forces from the control wires 142a and/or 142b.

In the depicted embodiment, when the mid-body control wire 142b is uncoupled from the anchor assembly 200, the mid-body regions of the anchor assembly 200 are no longer diametrically constrained by the mid-body control wire 142b. Hence, mid-body regions of the anchor assembly 200 are allowed to diametrically expand when the mid-body control wire 142b is uncoupled from the anchor assembly 200.

When the proximal control wire 142a is loosened and/or detached from one or more proximal end portions of the anchor assembly 200, the one or more portions that were coupled to the proximal control wire 142a become free to expand and deploy to intended orientations in relation to the mitral valve 17. For example, in the depicted embodiment, the proximal control wire 142a was coupled to three arched atrial holding features 240a, 240b, and 240c. When the proximal control wire 142a is uncoupled (e.g., slid out from or "un-lassoed") from the three arched atrial holding features 240a, 240b, and 240c, the three arched atrial holding features 240a, 240b, and 240c are free to deploy to their intended orientations in relation to the mitral valve 17. The three arched atrial holding features 240a, 240b, and 240c deploy generally radially outward (transversely) in relation to the longitudinal axis (the axis extending between the proximal and distal ends of the anchor assembly 200) of the anchor assembly 200. Hence, in the depicted embodiment the three arched atrial holding features 240a, 240b, and 240c self-deploy to respective positions directly adjacent to, or spaced apart just above, the annulus of the mitral valve 17. In those positions, the three arched atrial holding features 240a, 240b, and 240c resist migration of the anchor assembly 200 towards the left ventricle 18.

In addition, in the depicted embodiment when the proximal control wire 142a is loosened and subsequently detached from the three frame lobes 250a, 250b, and 250c, the three frame lobes 250a, 250b, and 250c become free to expand and deploy to intended orientations. In the depicted embodiment the three frame lobes 250a, 250b, and 250c diametrically expand into positions that are designed to interface with a valve assembly that will be deployed into a mating arrangement with the anchor assembly 200 as described further below.

In the depicted arrangement, the anchor assembly 200 is deployed in engagement with the native mitral valve 17. Nevertheless, the native mitral valve 17 is free to function normally. Moreover, in the depicted arrangement, while the inner catheter 160 is still coupled with the anchor assembly 200 at the hub 210, the anchor delivery catheter 140 (and other components of the transcatheter delivery system 100) are no longer attached to the anchor assembly 200. Hence, some components of the transcatheter delivery system 100 that were used to deploy the anchor assembly 200 can now be retracted and removed from the patient.

Figure 11:
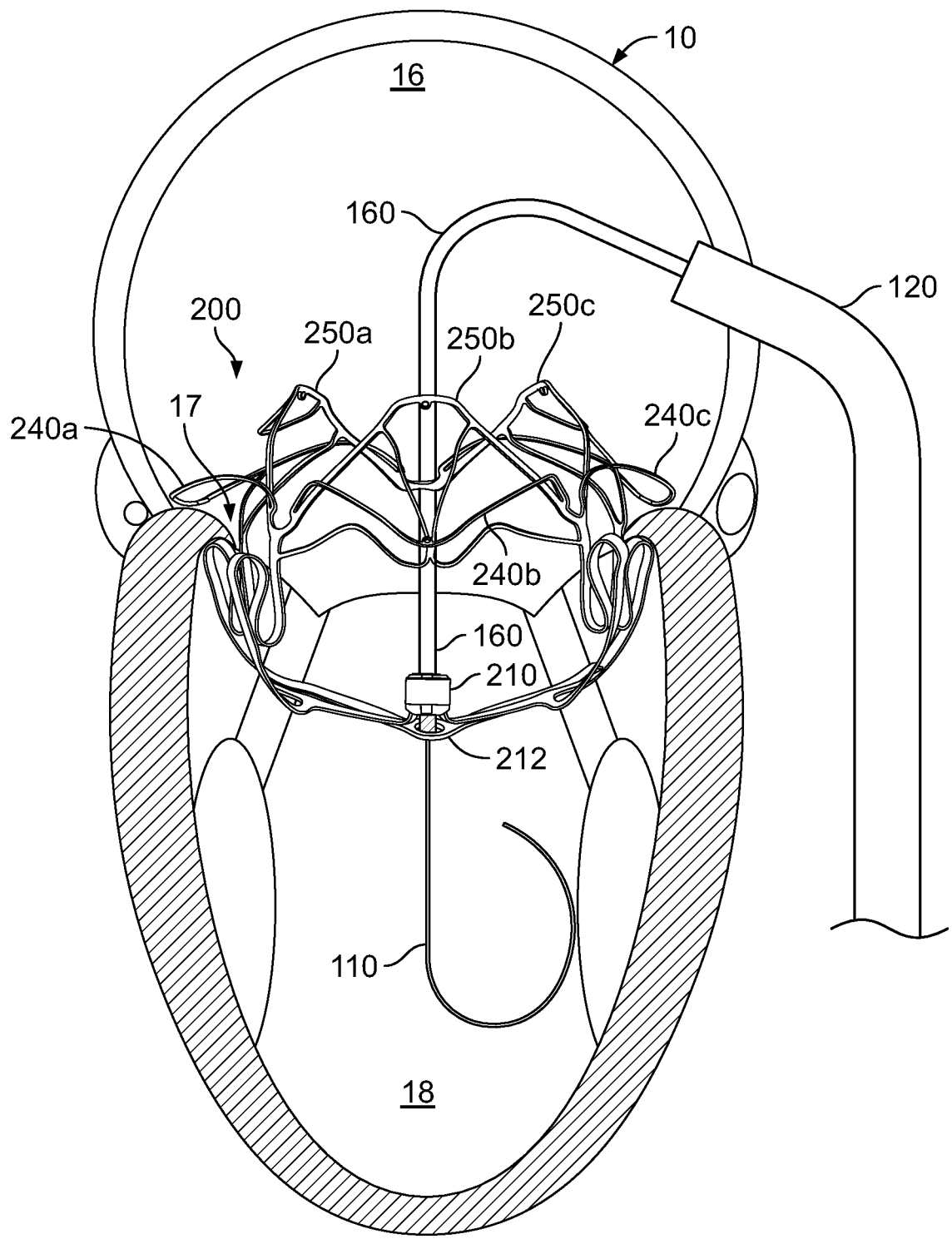
FIG. 11 shows a perspective view of the anchor assembly of FIG. 7 after the retraction of some of the catheters of the deployment system.

Referring also to FIG. 11, with the anchor assembly 200 deployed within the mitral valve 17 (as described above), the anchor delivery catheter 140 can be withdrawn, the secondary steerable catheter 150 can be withdrawn, and the anchor delivery sheath 130 can also be withdrawn. In fact, if so desired, the anchor delivery catheter 140, the secondary steerable catheter 150, and the anchor delivery sheath 130 can be completely withdrawn from the guide catheter 120. In contrast, in some implementations the inner catheter 160 is advantageously left attached to the hub 210 of the anchor assembly 200 (and left attached to the SAM containment member 212 in some implementations). As will be described further below, in some implementations the inner catheter 160 can be used as a "rail" on which a valve assembly is later deployed into the interior of the anchor assembly 200. However, in some implementations the anchor assembly 200 is completely detached from the delivery system 100, and the delivery system 100 is removed from the patient. After a period of minutes, hours, days, weeks, or months, subsequent to the deployment of the anchor assembly 200, a valve assembly can be installed into the anchor assembly 200 to complete the installation of the prosthetic mitral valve.

In some implementations, withdrawal of the anchor delivery catheter 140, the secondary steerable catheter 150, and the anchor delivery sheath 130 can be performed as follows. First, the anchor delivery catheter 140 can be withdrawn into the anchor delivery sheath 130. Then, the secondary steerable catheter 150 can be withdrawn into the anchor delivery sheath 130 while generally simultaneously undeflecting (relaxing) the bend(s) in the secondary steerable catheter 150. Thereafter, in some embodiments the anchor delivery catheter 140, the secondary steerable catheter 150, and the anchor delivery sheath 130 can be simultaneously withdrawn further, including up to completely from the guide catheter 120. As described further below, such individual and/or simultaneous movements of components of the delivery system 100 can be initiated and controlled using a deployment frame system (such as the example deployment frame system of FIG. 43 described below) in some implementations.

In the depicted implementation, the SAM containment member 212 is still restrained in its pre-deployed configuration. As described further below, in some embodiments the depicted embodiment of the SAM containment member 212 is deployed after the installation of a valve assembly into the anchor assembly 200. Alternatively, as described further below, in some embodiments of the SAM containment member 212, the SAM containment member 212 is deployed prior to the installation of a valve assembly into the anchor assembly 200.

Figure 12:
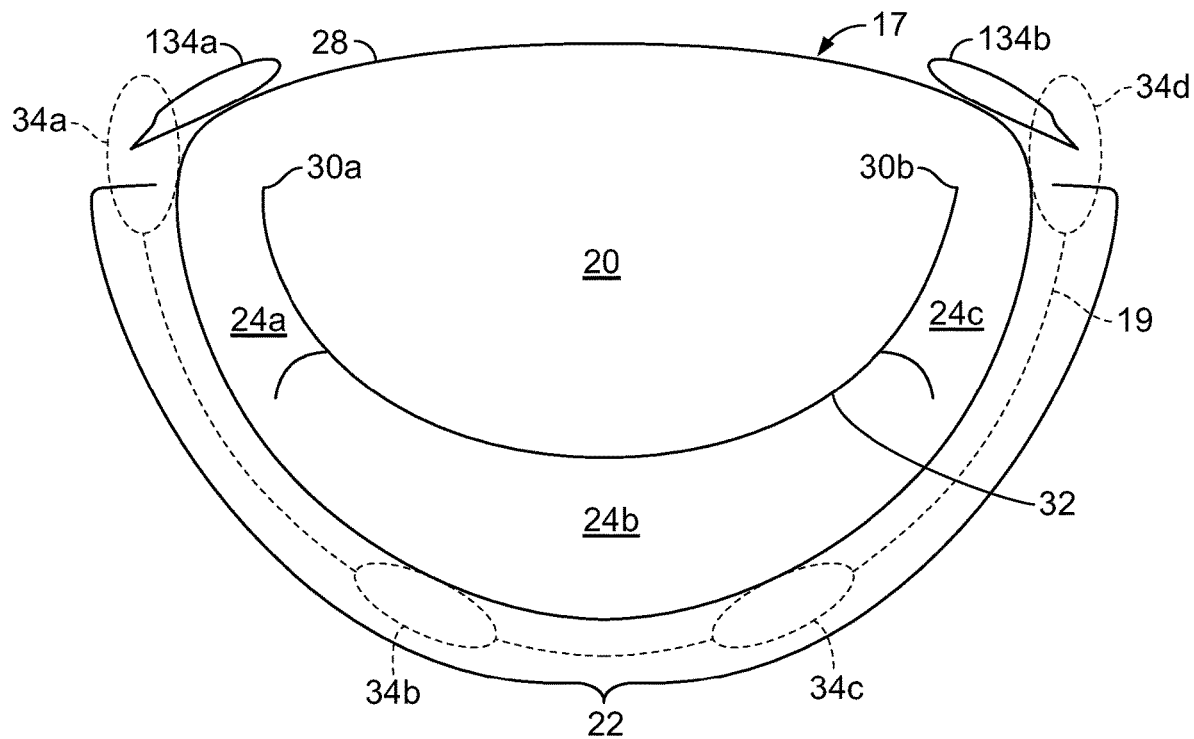
FIG. 12 is a top view of a native mitral valve and depicts a gutter perimeter of the sub-annular gutter of FIG. 7 (without the anchor assembly).

Referring to FIG. 12, the anatomy of the native mitral valve 17 includes some consistent and predictable structural features across patients that can be utilized for engaging the anchor assembly 200 therewith. For example, the native mitral valve 17 includes the aforementioned sub-annular gutter 19. In addition, the native mitral valve 17 includes a D-shaped annulus 28, an anterolateral commissure 30a, a posteromedial commissure 30b, a left fibrous trigone 134a, and a right fibrous trigone 134b. Further, the native mitral valve 17 includes an anterior leaflet 20 and a three-part posterior leaflet 22. The posterior leaflet 22 includes a lateral scallop 24a, a middle scallop 24b, and a medial scallop 24c. The free edges of the posterior leaflet 22 and the anterior leaflet 20 opposed each other and/or meet along a coaptation line 32.

The D-shaped annulus 28 defines the structure from which the anterior leaflet 20 and posterior leaflet 22 extend and articulate. The left and right fibrous trigones 134a and 134b are located near the left and right ends of the anterior leaflet 20 and generally adjacent the lateral and medial scallops 24a and 24c of the posterior leaflet 22. The sub-annular gutter 19 runs along the annulus 28 between the left and right fibrous trigones 134a and 134b along the posterior leaflet 22.

The regions at or near the high collagen annular trigones 134a and 134b can generally be relied upon to provide strong, stable anchoring locations. The muscle tissue in the regions at or near the trigones 134a and 134b also provides a good tissue ingrowth substrate for added stability and migration resistance of the anchor assembly 200. Therefore, the regions at or near the trigones 134a and 134b define a left anterior anchor zone 34a and a right anterior anchor zone 34d respectively. The left anterior anchor zone 34a and the right anterior anchor zone 34d provide advantageous target locations for placement of the lateral anterior foot 220a and the medial anterior foot 220d respectively.

Figure 13:
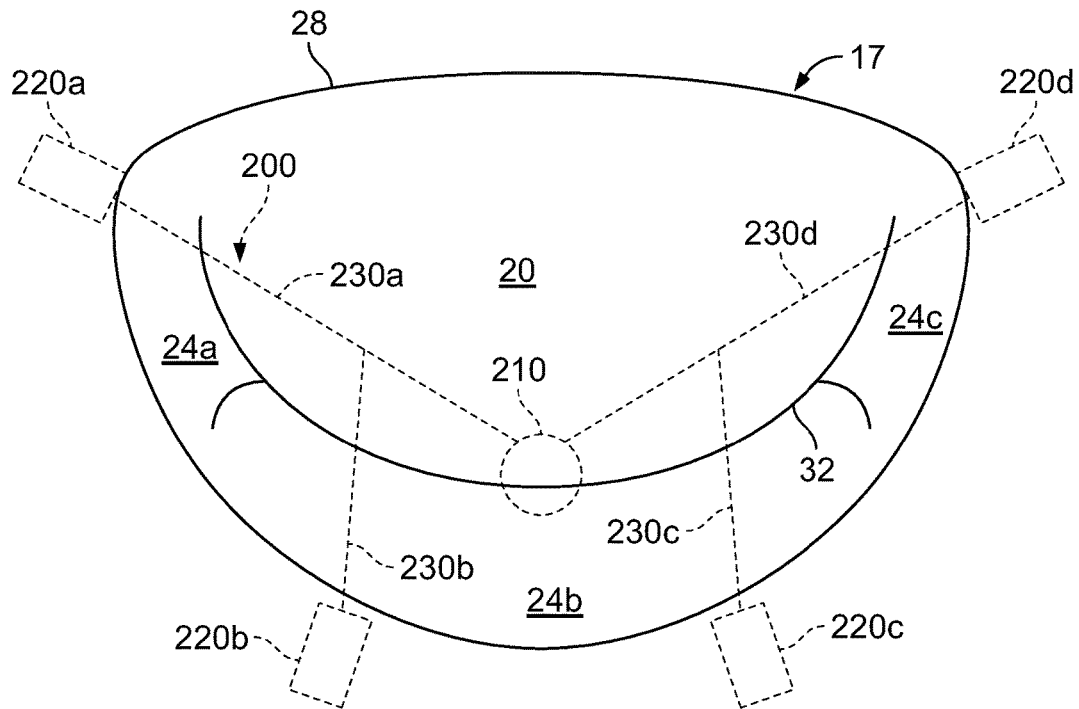
FIG. 13 shows the native mitral valve of FIG. 12 and a schematic representation of the sub-annular frame members of the anchor assembly of FIG. 7.

Referring also to FIG. 13, a schematic representation of the anchor assembly 200 is shown in combination with the native mitral valve 17 of FIG. 12. The depicted portions of the anchor assembly 200 include the hub 210, the lateral anterior anchor foot 220a, the lateral posterior anchor foot 220b, the medial posterior anchor foot 220c, the medial anterior anchor foot 220d, the lateral anterior sub-annular support arm 230a, the lateral posterior sub-annular support arm 230b, the medial posterior sub-annular support arm 230c, and the medial anterior sub-annular support arm 230d. Each of those portions of the anchor assembly 200 reside below the mitral valve 17 when deployed, hence those portions of the anchor assembly 200 are drawn with dashed lines.

In the depicted embodiment, the lateral anterior sub-annular support arm 230a extends from the hub 210. The lateral anterior anchor foot 220a is disposed on an outer end of the lateral anterior sub-annular support arm 230a. Similarly, the medial anterior sub-annular support arm 230d extends from the hub 210, and the medial anterior anchor foot 220d is disposed on an outer end of the medial anterior sub-annular support arm 230d. The lateral posterior sub-annular support arm 230b extends from a middle portion of the lateral anterior sub-annular support arm 230a. The lateral posterior anchor foot 220b is disposed on an outer end of the lateral posterior sub-annular support arm 230b. The medial posterior sub-annular support arm 230c extends from a middle portion of the medial anterior sub-annular support arm 230d. The medial posterior anchor foot 220c is disposed on an outer end of the medial posterior sub-annular support arm 230c.

The depicted arrangement of the sub-annular support arms 230a, 230b, 230c, and 230d is advantageous because the arrangement is designed to reduce or minimize the potential for interference (by the anchor assembly 200) with the natural functioning of the chordae tendineae of the mitral valve 17. For example, the lateral posterior sub-annular support arm 230b and the medial posterior sub-annular support arm 230c are aligned generally parallel with the chordae tendineae in the areas where the posterior sub-annular support arms 230b and 230c are disposed.

Moreover, other sub-annular portions of the anchor assembly are also positioned in advantageous locations for interfacing with the native mitral valve 17. For example, the hub 210 is advantageously positioned generally directly below the coaptation line 32. In addition, the lateral anterior anchor foot 220a can be positioned in the left anterior anchor zone 34a and the medial anterior anchor foot 220d can be positioned in the right anterior anchor zone 34d. Further, the lateral posterior anchor foot 220b and the medial posterior anchor foot 220c can be positioned in posterior areas of the sub-annular gutter 19, namely a lateral posterior anchor zone 34b and a medial posterior anchor zone 34c, respectively, in order to provide balanced and atraumatic coupling of the anchor assembly 200 to the native mitral valve 17. In some implementations, the locations of the lateral posterior anchor zone 34b and the medial posterior anchor zone 34c may vary from the depicted locations while still remaining within the sub-annular gutter 19. It should be understood that the depicted anchor assembly 200 is merely one non-limiting example of the anchor assemblies provided within the scope of this disclosure.

Figure 14:
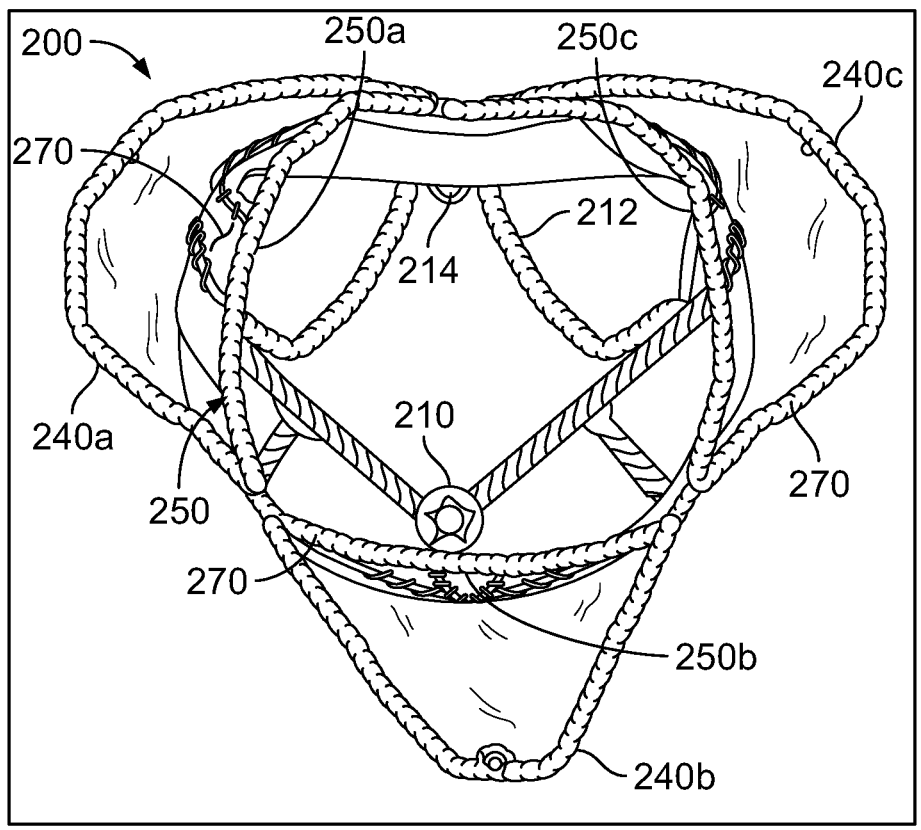
FIG. 14 shows a top view of the anchor assembly of FIG. 7 deployed in a sheet material that represents the annular plane of a mitral valve.
Figure 15:
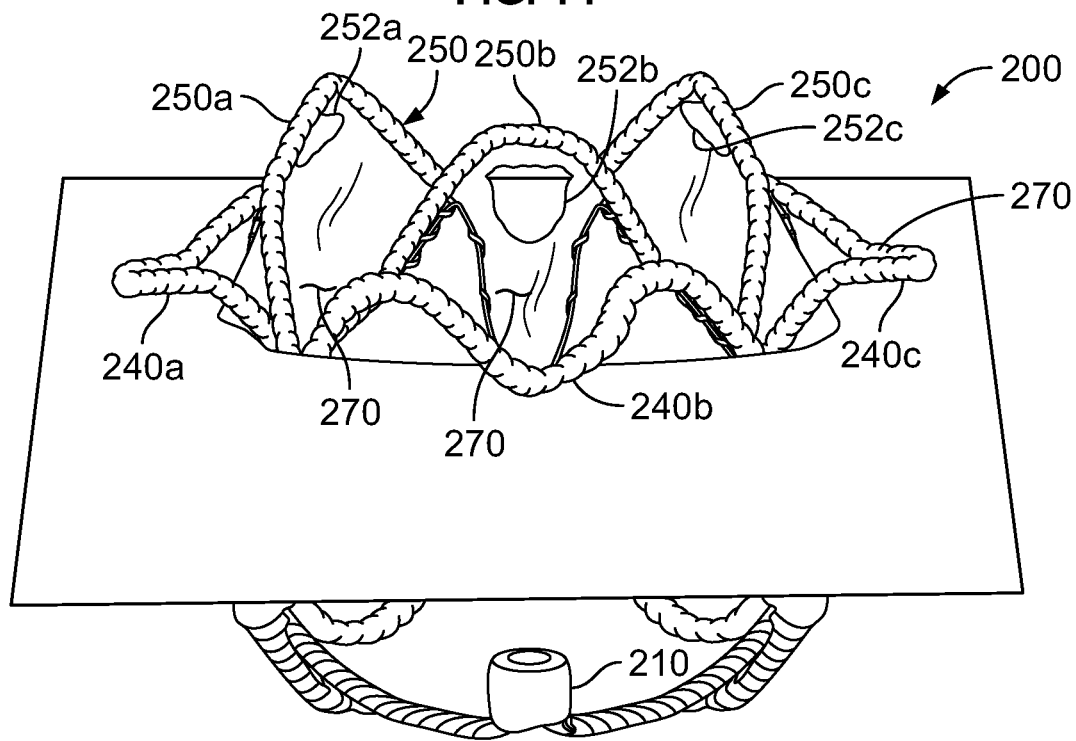
FIG. 15 shows a perspective view (slightly from the top) of the anchor assembly of FIG. 7 deployed in the material that represents the annular plane of a mitral valve (as in FIG. 14).

With reference to FIGS. 14 and 15, the example anchor assembly 200 is shown in a sheet material that represents the annular plane of a native mitral valve, to more clearly show which structures are supra-annular vs. sub-annular. A covering-material 270 is included on the framework of the anchor assembly 200. The supra-annular structures of the example anchor assembly 200 are shown.

In the depicted embodiment, the supra-annular structures of the anchor assembly 200 include: the lateral anterior atrial holding feature 240a, the posterior atrial holding feature 240b, and the medial anterior atrial holding feature 240c; the lateral anterior anchor arch 250a, the posterior anchor arch 250b, and the medial anterior anchor arch 250c. The lateral anterior anchor arch 250a, the posterior anchor arch 250b, and the medial anterior anchor arch 250c are joined with each other to form an undulating supra-annular ring 250 that acts as a supra-annular structural element for the anchor assembly 200. As will be described further below, the supra-annular ring 250 also defines an opening to a space within the interior of the anchor assembly 200 that is configured to receive and engage with a valve assembly. The atrial holding features 240a, 240b, and 240c are configured to contact the shelf-like supra-annular tissue surface above the mitral valve annulus, and to thereby stabilize the anchor assembly 200 in supra-annular areas and to provide migration resistance in the direction towards the left ventricle.

In some embodiments, the anchor assembly 200 includes a covering material 270 disposed on one or more portions of the anchor assembly 200. The covering material 270 can provide various benefits. For example, in some implementations the covering material 270 can facilitate tissue ingrowth and/or endothelialization, thereby enhancing the migration resistance of the anchor assembly 200 and preventing thrombus formation on blood contact elements. In another example, as described further below, the covering material 270 can be used to facilitate coupling between the anchor assembly 200 and a valve assembly that is received therein. The cover material 270 also prevents or minimizes abrasion and/or fretting between the anchor assembly 200 and valve assembly 300. The cover material 270 also prevents valve outer tissue abrasion related wear, and supports to the cuff material to enhance durability. The covering material 270 may also provide redundant sealing in addition to the cuff material of the valve assembly.

In the depicted embodiment, the covering material 270 is disposed essentially on the entire anchor assembly 200, including the SAM containment member 212 (except for the eyelet 214, although in some embodiments the eyelet 214 may be essentially covered by the covering material 270). In some embodiments, the covering material 270 is disposed on one or more portions of the anchor assembly 200, while one or more other portions of the anchor assembly 200 do not have the covering material 270 disposed thereon. While the depicted embodiment includes the covering material 270, the covering material 270 is not required in all embodiments. In some embodiments, two or more portions of covering material 270, which can be separated and/or distinct from each other, can be disposed on the anchor assembly 200. That is, in some embodiments a particular type of covering material 270 is disposed on some areas of the anchor assembly 200 and a different type of covering material 270 is disposed on other areas of the anchor assembly 200.

In some embodiments, the covering material 270, or portions thereof, comprises a fluoropolymer, such as an expanded polytetrafluoroethylene (ePTFE) polymer. In some embodiments, the covering material 270, or portions thereof, comprises a polyester, a silicone, a urethane, ELAST-EON™ (a silicone and urethane polymer), another biocompatible polymer, DACRON®, polyethylene terephthalate (PET), copolymers, or combinations and subcombinations thereof. In some embodiments, the covering material 270 is manufactured using techniques such as, but not limited to, extrusion, expansion, heat-treating, sintering, knitting, braiding, weaving, chemically treating, and the like. In some embodiments, the covering material 270, or portions thereof, comprises a biological tissue. For example, in some embodiments the covering material 270 can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In the depicted embodiment, the covering material 270 is disposed on the interior and the exterior of the anchor assembly 200. In some embodiments, the covering material 270 is disposed on the just the exterior of the anchor assembly 200. In some embodiments, the covering material 270 is disposed on the just the interior of the anchor assembly 200. In some embodiments, some portions of the anchor assembly 200 are covered by the covering material 270 in a different manner than other portions of the anchor assembly 200.

In some embodiments, the covering material 270 is attached to at least some portions of the anchor assembly 200 using an adhesive. In some embodiments, epoxy is used as an adhesive to attach the covering material 270 to the anchor assembly 200, or portions thereof. In some embodiments, wrapping, stitching, lashing, banding, and/or clips, and the like can be used to attach the covering material 270 to the anchor assembly 200. In some embodiments, a combination of techniques are used to attach the covering material 270 to the anchor assembly 200.

In some embodiments, the covering material 270, or portions thereof, has a microporous structure that provides a tissue ingrowth scaffold for durable sealing and/or supplemental anchoring strength of the anchor assembly 200. In some embodiments, the covering material 270 is made of a membranous material that inhibits or reduces the passage of blood through the covering material 270. In some embodiments, the covering material 270, or portions thereof, has a material composition and/or configuration that inhibits or prevents tissue ingrowth and/or endothelialization to the covering material 270.

In some embodiments, the covering material 270 can be modified by one or more chemical or physical processes that enhance certain physical properties of the covering material 270. For example, a hydrophilic coating may be applied to the covering material 270 to improve the wettability and echo translucency of the covering material 270. In some embodiments, the covering material 270 may be modified with chemical moieties that promote or inhibit one or more of endothelial cell attachment, endothelial cell migration, endothelial cell proliferation, and resistance to thrombosis. In some embodiments, the covering material 270 may be modified with covalently attached heparin or impregnated with one or more drug substances that are released in situ.

In some embodiments, covering material 270 is pre-perforated to modulate fluid flow through the covering material 270 and/or to affect the propensity for tissue ingrowth to the covering material 270. In some embodiments, the covering material 270 is treated to make the covering material 270 stiffer or to add surface texture. In some embodiments, selected portions of the covering material 270 are so treated, while other portions of the covering material 270 are not so treated. Other covering material 270 material treatment techniques can also be employed to provide beneficial mechanical properties and tissue response interactions. In some embodiments, portions of the covering material 270 have one or more radiopaque markers attached thereto to enhance in vivo radiographic visualization.

In some embodiments, the anchor assembly 200 can include features that are designed for coupling with a valve assembly that is received by the anchor assembly 200. For example, the lateral anterior anchor arch 250a, the posterior anchor arch 250b, and the medial anterior anchor arch 250c can be shaped and arranged for coupling with a valve assembly (as described further below). In addition, in some embodiments the anchor arches 250a, 250b, and 250c can include one or more covering-material cut-outs 252a, 252b, and 252c respectively. In some embodiments, the valve assembly (as described further below in reference to FIG. 38) can include features that become physically received within the covering-material cut-outs 252a, 252b, and 252c when the valve assembly is coupled with the anchor assembly 200. Such an arrangement can serve to provide a robust coupling arrangement between the valve assembly and the anchor assembly 200.

Figure 16:
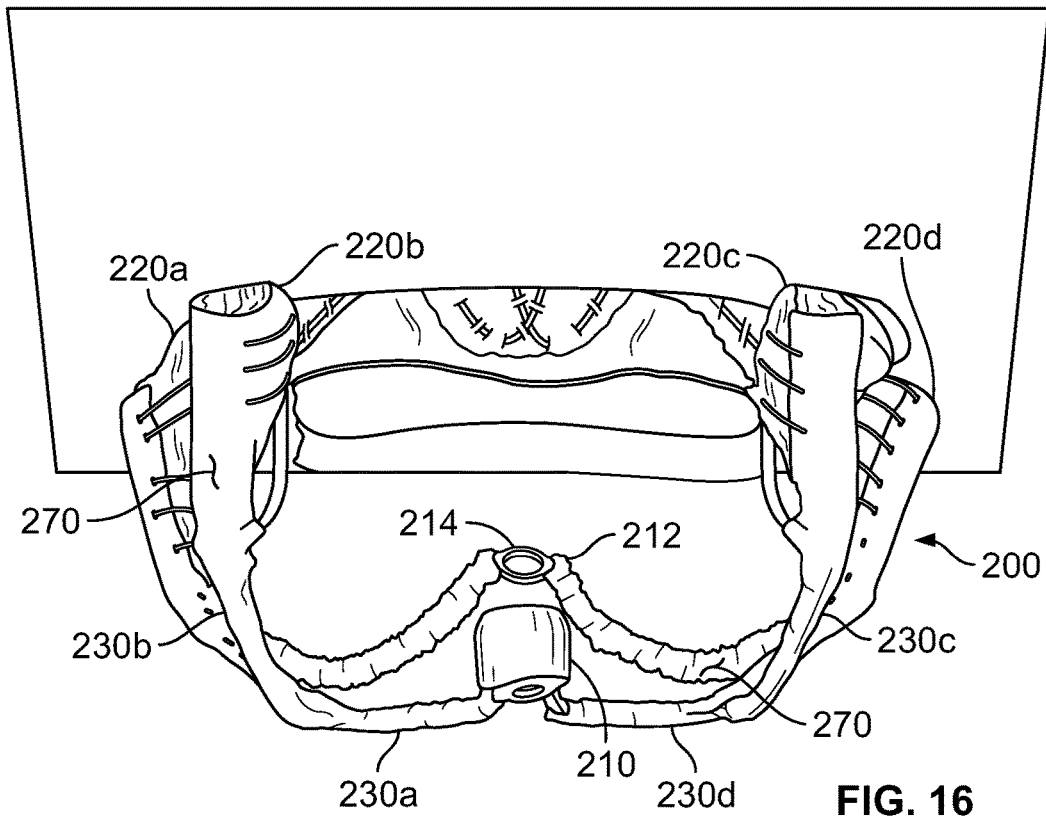
FIG. 16 shows a perspective view (slightly from the bottom) of the anchor assembly of FIG. 7 deployed in the material that represents the annular plane of a mitral valve (as in FIG. 14).
Figure 17:
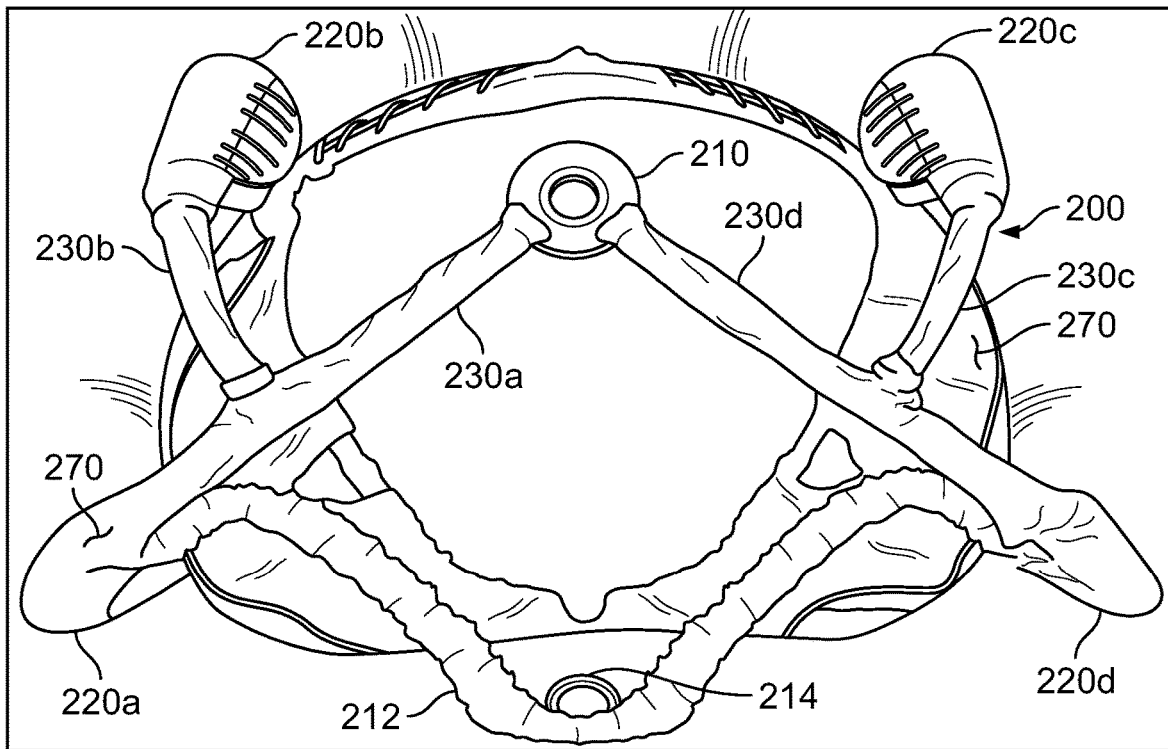
FIG. 17 shows a bottom view of the anchor assembly of FIG. 7 deployed in the material that represents the annular plane of a mitral valve (as in FIG. 14).

With reference to FIGS. 16 and 17, the example anchor assembly 200 is shown in a sheet material that represents the annular plane of a native mitral valve. The sub-annular portions of the example anchor assembly 200 are shown.

In the depicted embodiment, the sub-annular portions of the anchor assembly 200 include the hub 210, the SAM containment member 212, the lateral anterior anchor foot 220a, the lateral posterior anchor foot 220b, the medial posterior anchor foot 220c, the medial anterior anchor foot 220d, the lateral anterior sub-annular support arm 230a, the lateral posterior sub-annular support arm 230b, the medial posterior sub-annular support arm 230c, and the medial anterior sub-annular support arm 230d. Each of those portions of the anchor assembly 200 reside below the native mitral valve annulus when deployed the anchor assembly 200 is deployed in a native mitral valve.

In the depicted embodiment, the lateral anterior sub-annular support arm 230a extends from the hub 210. The lateral anterior anchor foot 220*a* is disposed on an outer end of the lateral anterior sub-annular support arm 230*a*. Similarly, the medial anterior sub-annular support arm 230*d* extends from the hub 210, and the medial anterior anchor foot 220*d* is disposed on an outer end of the medial anterior sub-annular support arm 230*d*. The lateral posterior sub-annular support arm 230*b* extends from a middle portion of the lateral anterior sub-annular support arm 230*a*. The lateral posterior anchor foot 220*b* is disposed on an outer end of the lateral posterior sub-annular support arm 230*b*. The medial posterior sub-annular support arm 230*c* extends from a middle portion of the medial anterior sub-annular support arm 230*d*. The medial posterior anchor foot 220*c* is disposed on an outer end of the medial posterior sub-annular support arm 230*c*. A first end of the SAM containment member 212 extends from the lateral anterior sub-annular support arm 230*a*, and a second end of the SAM containment member 212 extends from the medial anterior sub-annular support arm 230*d*.

Referring to FIGS. 18-21, the frame of an example anchor assembly 200 is shown in its fully expanded configuration. The anchor assembly 200 is shown without a covering-material so that the elongate member framework of the example anchor assembly 200 is clearly visible in FIGS. 18-20, and with covering-material in FIG. 21.

In some embodiments, the elongate members of the anchor assembly 200 are formed from a single piece of precursor material (e.g., sheet or tube) that is cut, expanded, and connected to the hub 210. For example, some embodiments are fabricated from a tube that is laser-cut (or machined, chemically etched, water-jet cut, etc.) and then expanded and shape-set into its final expanded size and shape. In some embodiments, the anchor assembly 200 is created compositely from multiple elongate members (e.g., wires or cut members) that are joined together with the hub 210 and each other to form the anchor assembly 200.

Figure 18:
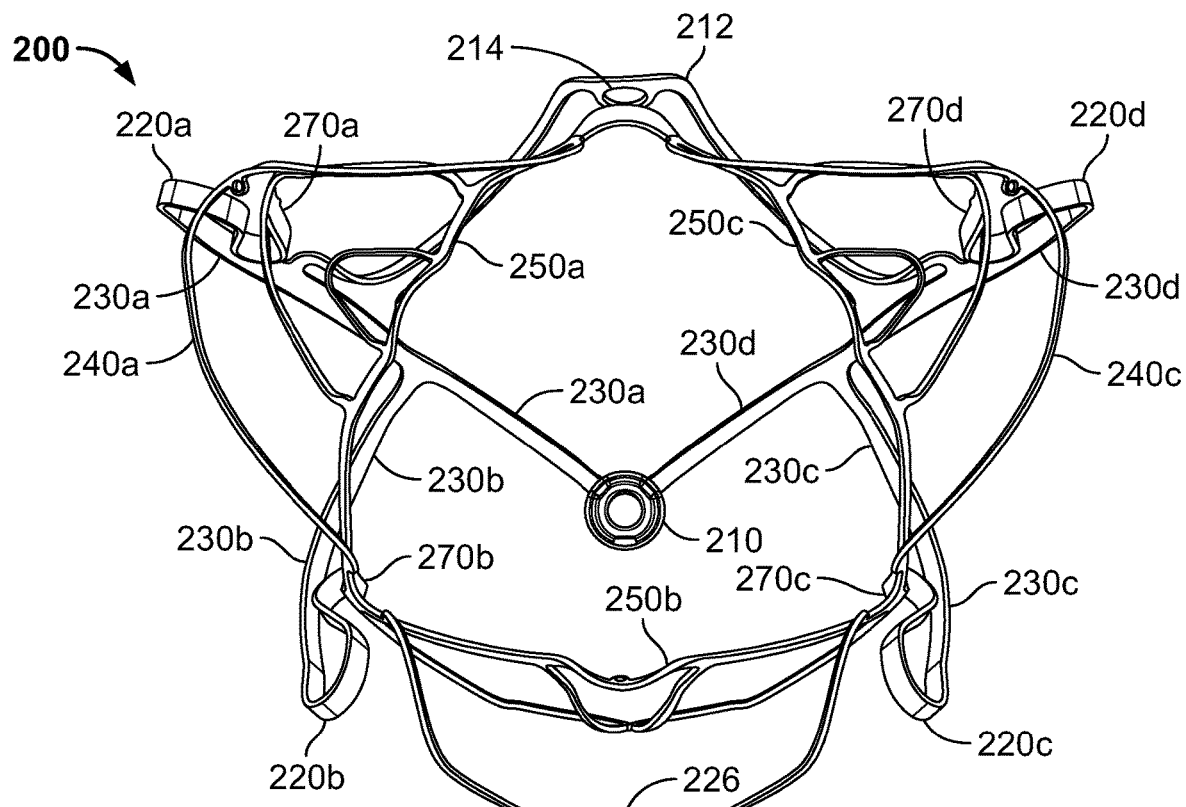
FIG. 18 shows a perspective top view of an example frame of the anchor assembly of FIG. 7, in accordance with some embodiments.
Figure 19:
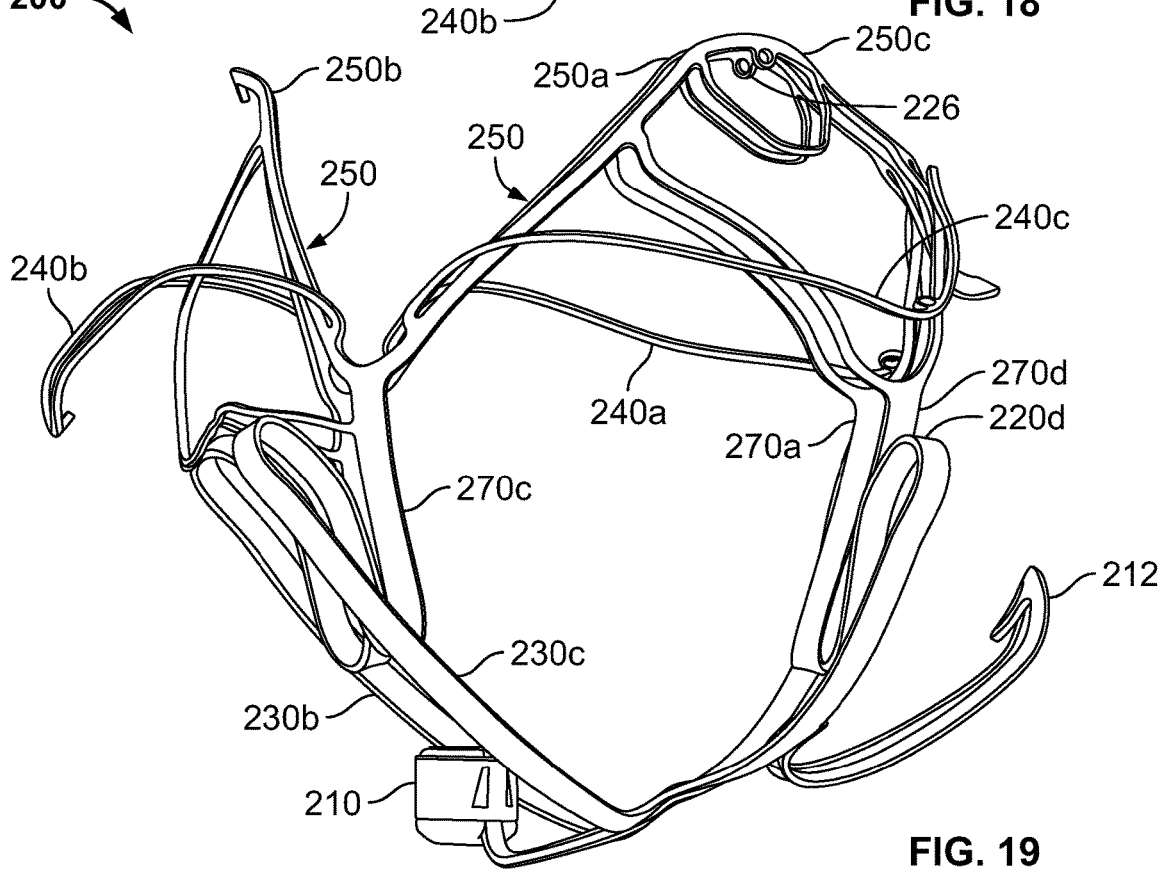
FIG. 19 shows a perspective side view of the example frame of the anchor assembly of FIG. 7, in accordance with some embodiments.
Figure 20:
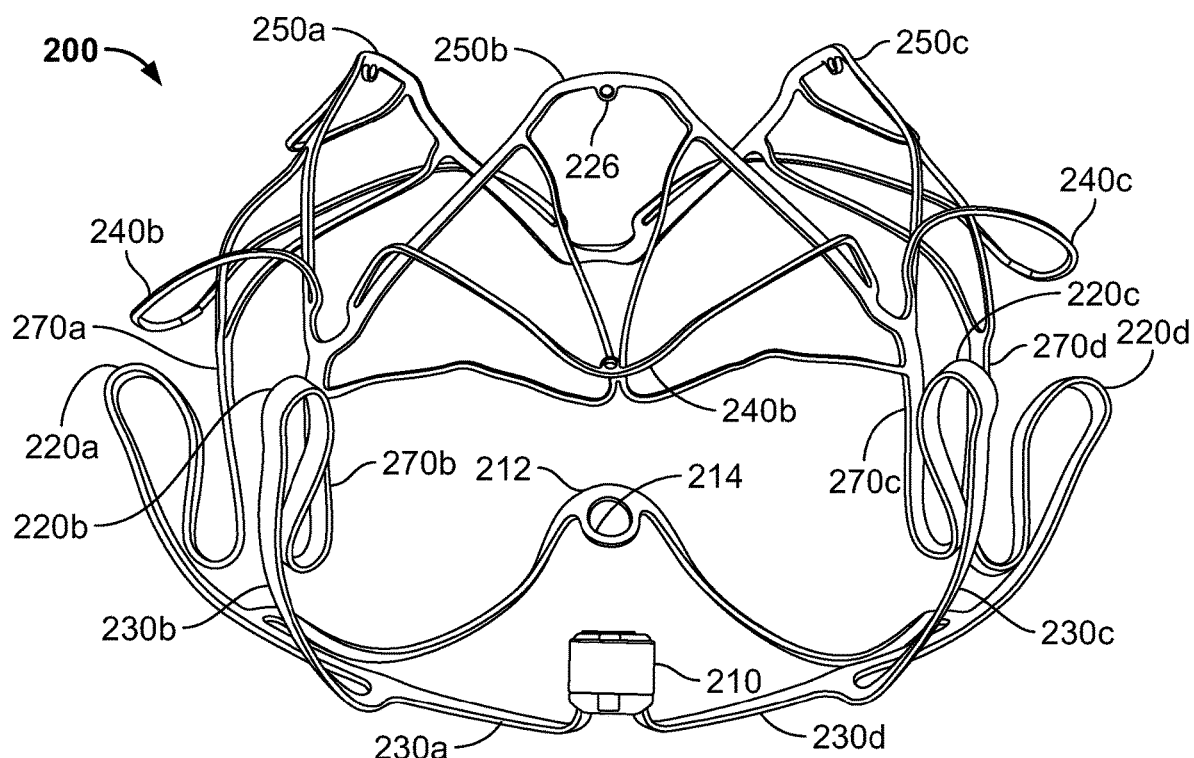
FIG. 20 shows a posterior side view of the example frame of the anchor assembly of FIG. 7, in accordance with some embodiments.
Figure 21:
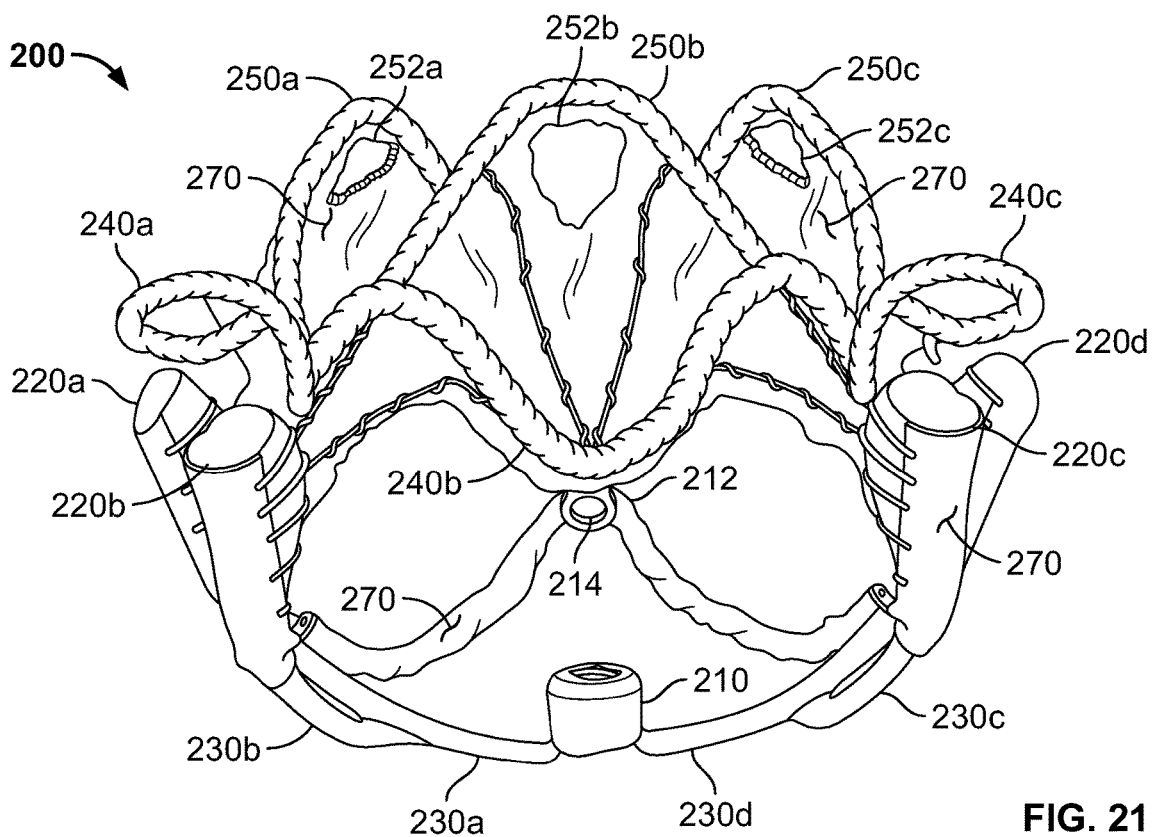
FIG. 21 shows a posterior side view of the anchor assembly of FIG. 7 including a covering material disposed on portions of the anchor frame.

The elongate members of the anchor assembly 200 can be comprised of various materials and combinations of materials. In some embodiments, nitinol (NiTi) is used as the material of the elongate members of the anchor assembly 200, but other materials such as stainless steel, L605 steel, polymers, MP35N steel, stainless steels, titanium, cobalt/chromium alloy, polymeric materials, Pyhnox, Elgiloy, or any other appropriate biocompatible material, and combinations thereof can be used. The super-elastic properties of NiTi make it a particularly good candidate material for the elongate members of the anchor assembly 200 because, for example, NiTi can be heat-set into a desired shape. That is, NiTi can be heat-set so that the anchor assembly 200 tends to self-expand into a desired shape when the anchor assembly 200 is unconstrained, such as when the anchor assembly 200 is deployed out from the anchor delivery sheath 130. A anchor assembly 200 made of NiTi, for example, may have a spring nature that allows the anchor assembly 200 to be elastically collapsed or "crushed" to a low-profile delivery configuration and then to reconfigure to the expanded configuration as shown in FIGS. 18-20. The anchor assembly 200 may be generally conformable, fatigue resistant, and elastic such that the anchor assembly 200 can conform to the topography of the surrounding tissue when the anchor assembly 200 is deployed in a native mitral valve of a patient.

In some embodiments, the diameter or width/thickness of one or more of the elongate members forming the anchor assembly 200 may be within a range of about 0.008" to about 0.015" (about 0.20 mm to about 0.40 mm), or about 0.009" to about 0.030" (about 0.23 mm to about 0.76 mm), or about 0.01" to about 0.06" (about 0.25 mm to about 1.52 mm), or about 0.02" to about 0.10" (about 0.51 mm to about 2.54 mm), or about 0.06" to about 0.20" (about 1.52 mm to about 5.08 mm). In some embodiments, the elongate members forming the anchor assembly 200 may have smaller or larger diameters or widths/thicknesses. In some embodiments, each of the elongate members forming the anchor assembly 200 has essentially the same diameter or width/thickness. In some embodiments, one or more of the elongate members forming the anchor assembly 200 has a different diameter or width/thickness than one or more of the other elongate members of the anchor assembly 200. In some embodiments, one or more portions of one or more of the elongate members forming the anchor assembly 200 may be tapered, widened, narrowed, curved, radiused, wavy, spiraled, angled, and/or otherwise non-linear and/or not consistent along the entire length of the elongate members of the anchor assembly 200. Such features and techniques can also be incorporated with the valve assemblies of the prosthetic mitral valves provided herein.

In some embodiments, the elongate members forming the anchor assembly 200 may vary in diameter, thickness and/or width so as to facilitate variations in the forces that are exerted by the anchor assembly 200 in specific regions thereof, to increase or decrease the flexibility of the anchor assembly 200 in certain regions, to enhance migration resistance, and/or to control the process of compression (crushability) in preparation for deployment and the process of expansion during deployment of the anchor assembly 200.

In some embodiments, one or more of the elongate members of the elongate members forming the anchor assembly 200 may have a circular cross-section. In some embodiments, one or more of the elongate members forming the anchor assembly 200 may have a rectangular cross-sectional shape, or another cross-sectional shape that is not rectangular. Examples of cross-sectional shapes that the elongate members forming the anchor assembly 200 may have include circular, C-shaped, square, ovular, rectangular, elliptical, triangular, D-shaped, trapezoidal, including irregular cross-sectional shapes formed by a braided or stranded construct, and the like. In some embodiments, one or more of the elongate members forming the anchor assembly 200 may be essentially flat (i.e., such that the width to thickness ratio is about 2:1, about 3:1, about 4:1, about 5:1, or greater than about 5:1). In some examples, one or more of the elongate members forming the anchor assembly 200 may be formed using a center-less grind technique, such that the diameter of the elongate members varies along the length of the elongate members.

The anchor assembly 200 may include features that are directed to enhancing one or more desirable functional performance characteristics of the prosthetic mitral valve devices. For example, some features of the anchor assembly 200 may be directed to enhancing the conformability of the prosthetic mitral valve devices. Such features may facilitate improved performance of the prosthetic mitral valve devices by allowing the devices to conform to irregular tissue topographies and/or dynamically variable tissue topographies, for example. Such conformability characteristics can be advantageous for providing effective and durable performance of the prosthetic mitral valve devices. In some embodiments of the anchor assembly 200, some portions of the anchor assembly 200 are designed to be more conformable than other portions of the same anchor assembly 200.

That is, the conformability of a single anchor assembly 200 can be designed to be different at various areas of the anchor assembly 200.

In some embodiments, the anchor assembly 200 includes features for enhanced in vivo radiographic visibility. In some embodiments, portions of the anchor assembly 200, such as one or more of the anchor feet 220a, 220b, 220c, and 220d, and/or SAM containment member 212, may have one or more radiopaque markers attached thereto. In some embodiments, some or all portions of the anchor assembly 200 are coated (e.g., sputter coated) with a radiopaque coating.

The anchor assembly 200 can also include one or more eyelets 226 in frame portions adjacent the arches. The eyelets 226 can be used for various purposes such as, but not limited to, holding radiopaque marker material, attachment points for suture loops or other elements which are additional control points for delivery and retrieval of the assembly, locations to secure a positional delivery frame, and the like.

In some embodiments, such as the depicted embodiment, the supra-annular structures and sub-annular structures of the anchor assembly 200 are interconnected by a lateral anterior inter-annular connection 270a, a lateral posterior inter-annular connection 270b, a medial posterior inter-annular connection 270c, and a medial anterior inter-annular connection 270d. For example, the lateral anterior inter-annular connection 270a connects the lateral anterior anchor foot 220a with the lateral anterior anchor arch 250a. Similarly, the medial anterior inter-annular connection 270d connects the medial anterior anchor foot 220d with the medial anterior anchor arch 250c. In addition, the lateral posterior inter-annular connection 270b connects the lateral posterior anchor foot 220b with the lateral anterior anchor arch 250a and the posterior anchor arch 250b, and the medial posterior inter-annular connection 270c connects the medial posterior anchor foot 220c with the posterior anchor arch 250b and the medial anterior anchor arch 250c.

In the depicted embodiment, the SAM containment member 212 extends anteriorly from the sub-annular support arms of the anchor assembly 200. For example, the SAM containment member 212, as depicted, comprises an elongate member with a first end that extends from the lateral anterior sub-annular support arm 230a and a second end that extends from the medial anterior sub-annular support arm 230d. In some embodiments, portions of the SAM containment member 212 may extend from other areas on the anchor assembly 200. While one particular embodiment of the SAM containment member 212 is depicted, it should be understood that multiple SAM containment member embodiments are envisioned and within the scope of this disclosure.

In the depicted embodiment, the SAM containment member 212 is integrally formed as part of the anchor assembly 200. In specific embodiments, the SAM containment member 212, or portions thereof, may be formed separately from the anchor assembly 200 and thereafter attached to the anchor assembly 200.

The SAM containment member 212, as shown, is in a deployed configuration. In some embodiments, the SAM containment member 212 is biased to self-reconfigure to the deployed configuration when the SAM containment member 212 is unconstrained. When the anchor assembly 200 is implanted in a native mitral valve and the SAM containment member 212 is in the deployed configuration, the SAM containment member 212 is disposed behind the anterior leaflet of a native mitral valve to physically block the anterior leaflet from obstructing the LVOT. As used herein, "behind" an anterior leaflet refers to the aortic side of the native mitral valve leaflet when the leaflet is open. In some implementations, while the SAM containment member 212 is deployed, the elongate members of the SAM containment member 212 may engage with the anterior leaflet and/or chordae to reduce the likelihood of SAM. The engagement can be anywhere along the lengths of the elongate members of the SAM containment member 212. For example, in some implementations portions of the elongate members of the SAM containment member 212 can actually engage the lateral edge of the anterior leaflet and/or chordae to spread or widen the anterior leaflet at the lateral edges thereby restricting its movement and also reducing likelihood of SAM.

In some embodiments, a shape-setting process is used to instill a bias so that the SAM containment member 212 tends seek its deployed configuration. Alternatively or additionally, as described further below, in some embodiments the SAM containment member 212 may be deflected into the deployed configuration by the application of one or more forces during the deployment of the SAM containment member 212.

In some embodiments, the SAM containment member 212 includes an attachment element 214 (a threaded eyelet 214 in this embodiment). The eyelet 214 provides an attachment feature that can be used to control the configuration and deployment of the SAM containment member 212. In some embodiments, other types of attachment elements 214 (as alternatives to the eyelet 214) can be included on the SAM containment member 212. For example, in some embodiments one or more protrusions, ball ends, recesses, clips, breakable elements, deflectable elements, bends, and the like, and combinations thereof, can be included on the SAM containment member 212 as an attachment element 214.

Still referring to FIGS. 18-21, as described above the anchor feet 220a, 220b, 220c, and 220d are sized and shaped to engage the sub-annular gutter 19 of the mitral valve 17 (FIG. 12). In some embodiments, the anterior feet 220a and 220d are spaced apart from each other by a distance in a range of about 30 mm to about 45 mm, or about 20 mm to about 35 mm, or about 40 mm to about 55 mm. In some embodiments, the posterior feet 220b and 220c are spaced apart from each other by a distance in a range of about 20 mm to about 30 mm, or about 10 mm to about 25 mm, or about 25 mm to about 40 mm.

In some embodiments, the anchor feet 220a, 220b, 220c, and 220d have a height ranging from about 8 mm to about 12 mm, or more than about 12 mm. In some embodiments, the anchor feet 220a, 220b, 220c, and 220d have a gutter engaging surface area (when fabric covered) ranging from about 6 mm$^2$ to about 24 mm$^2$. In some embodiments, the anchor feet 220a, 220b, 220c, and 220d each have essentially the same gutter engaging surface area. In particular embodiments, one or more of the anchor feet 220a, 220b, 220c, and 220d has a different gutter engaging surface area than one or more of the other anchor feet 220a, 220b, 220c, and 220d. The anchor feet 220a, 220b, 220c, and 220d can have widths ranging within about 1.5 mm to about 4.0 mm or more, and lengths ranging within about 3 mm to about 6 mm or more. The anchor feet 220a, 220b, 220c, and 220d are sized and shaped so that the anchor assembly 200 does not significantly impair the natural function of mitral valve chordae tendineae, the native mitral valve leaflets, and papillary muscles even after the anchor assembly is anchored at the mitral valve site.

As described previously, the anchor assembly 200 is designed to avoid interference with the functioning of the native mitral valve 17 (FIG. 12). Therefore, the anchor assembly 200 can be implanted within the native mitral valve 17 some time prior to the deployment therein of a replacement valve assembly, without degradation of valve 17 function during the period of time between the anchor implantation and the valve implantation (whether that time is on the order of minutes, or even several days or months). To avoid such interference between the anchor assembly 200 and the native mitral valve 17, the inter-annular connections 270a, 270b, 270c, and 270d pass through the coaptation line 32 approximately. More particularly, the lateral anterior inter-annular connection 270a passes through the coaptation line 32 adjacent to the anterolateral commissure 30a. In like manner, the medial anterior inter-annular connection 270d passes through the coaptation line 32 adjacent to the posteromedial commissure 30b. In some implementations, the lateral posterior inter-annular connection 270b and medial posterior inter-annular connection 270c pass through the native mitral valve 17 in locations that are posteriorly biased from the natural coaptation line 32. In such a case, the posterior leaflet 22 will tend to compliantly wrap around the lateral posterior inter-annular connection 270b and medial posterior inter-annular connection 270c to facilitate sealing of the mitral valve 17 with the anchor assembly 200 coupled thereto.

Figure 22:
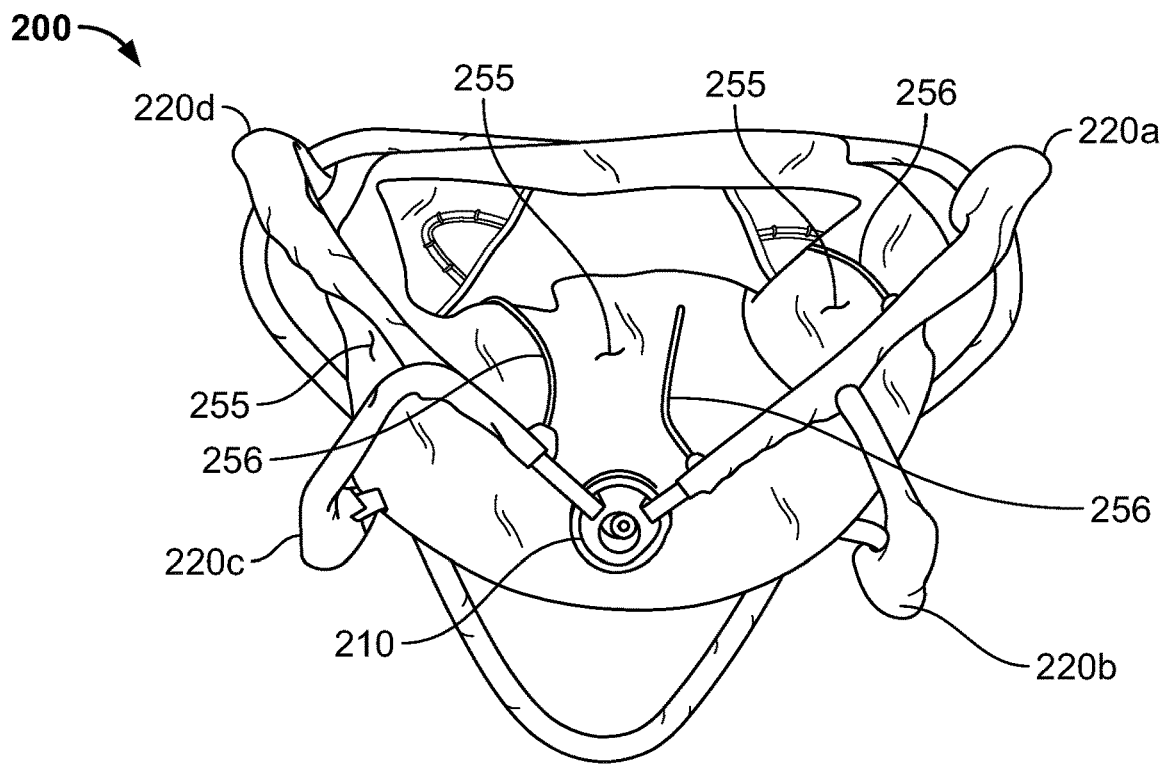
FIG. 22 shows a bottom view of an example anchor assembly that includes prosthetic elements for leaflet augmentation.
Figure 23:
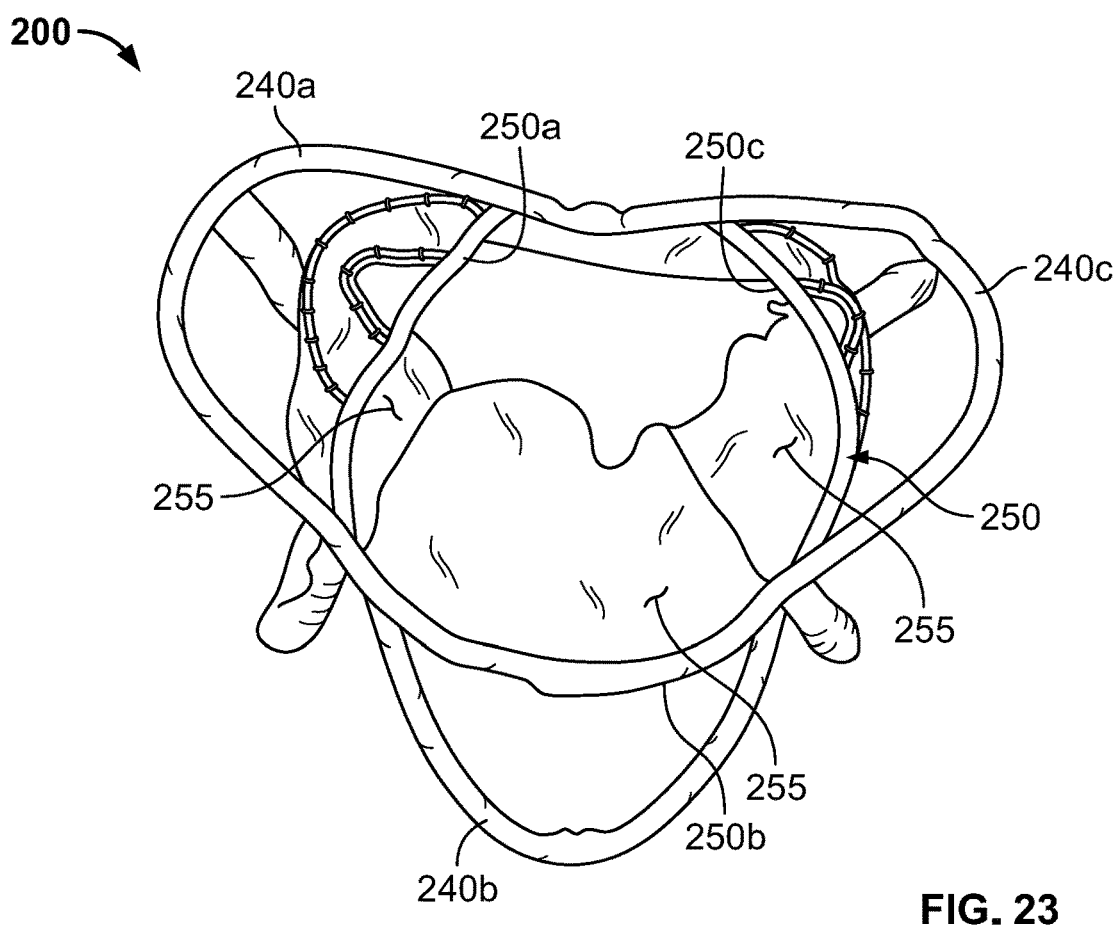
FIG. 23 shows a top view of the anchor assembly of FIG. 22.
Figure 24:
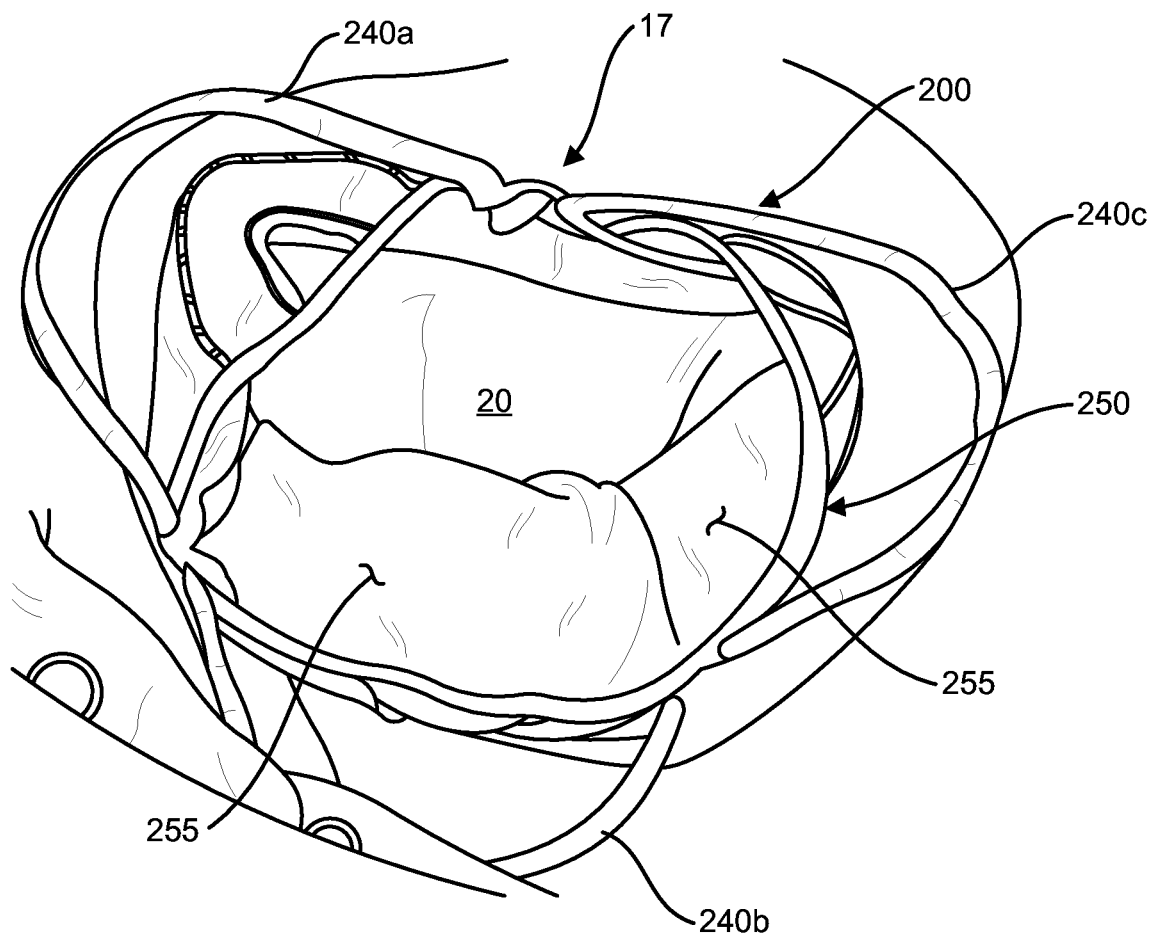
FIG. 24 shows the anchor assembly of FIG. 22 implanted in a native mitral valve.

Referring also to FIGS. 22-24, while the anchor assembly 200 is designed to be implanted without affecting the function of the native mitral valve 17, in some cases a patient's particular native valve anatomy, valve condition, or other factors may cause some mitral regurgitation (MR) to temporarily occur or increase when the anchor assembly 200 is implanted (prior to the installation of a prosthetic valve assembly, as described further below). Accordingly, in order to mitigate such temporary MR, some embodiments of the anchor assembly 200 include one or more prosthetic elements that work in conjunction with the native valve leaflets to enhance the sealing function of the native mitral valve 17.

In the depicted embodiment, the anchor assembly 200 includes an example prosthetic element 255 that temporarily augments the native posterior leaflet 22 (FIG. 12) to enhance the seal of the native mitral valve 17 while the anchor assembly 200 resides within the native mitral valve 17. The prosthetic element 255 is a flexible, sheet-like material that is attached to a portion of the supra-annular ring 250 (which is comprised of the lateral anterior anchor arch 250a, the posterior anchor arch 250b, and the medial anterior anchor arch 250c). In the depicted embodiment, the prosthetic element 255 is attached via sutures and spans across the base of the posterior anchor arch 250b, and partially spans across the base of the lateral anterior anchor arch 250a and the medial anterior anchor arch 250c. As such, the prosthetic element 255 is configured to essentially mimic the position, movements, and valvular functioning of the native posterior leaflet 22.

In some embodiments, the prosthetic element 255 is made of materials such as, but not limited to, DACRON®, polyethylene terephthalate (PET), expanded polytetrafluoroethylene (ePTFE), polyester, silicone, urethane, ELAST-EON™ (a silicone and urethane polymer), another biocompatible polymer, copolymers, or combinations and subcombinations thereof. In some embodiments, the prosthetic element 255 is manufactured using techniques such as, but not limited to, knitting, braiding, weaving, molding, extrusion, expansion, heat-treating, sintering, chemically treating, and the like. In some embodiments, the prosthetic element 255, or portions thereof, comprises a biological tissue. For example, in some embodiments the prosthetic element 255 can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents. In some embodiments, the tissues are treated with alcohols to dry the tissues. Later, the tissues are hydrated just prior to deploying the anchor assembly 200.

In the depicted embodiment, the prosthetic element 255 includes seams that allow the otherwise planar material of the prosthetic element 255 to be contoured to the curved shape of the posterior circumference of the anchor assembly 200 without excess material. In some embodiments, the prosthetic element 255 is a seamless construct.

In some embodiments, the extent or distance that the prosthetic element 255 can deflect is mechanically limited. For example, in the depicted embodiment four tethers 256 (e.g., suture cords) are included to mechanically limit the extent to which the prosthetic element 255 can deflect. In some embodiments, the number of tethers 256 can be zero, one, two, three, four, five six, seven, eight, or more than eight. The tethers 256 are attached to the free edge of the prosthetic element 255 and to the sub-annular frame of the anchor assembly 200. Accordingly, the tethers 256 limit the extent to which the free edge of the prosthetic element 255 can extend in a superior direction (i.e., toward the left atrium). The tethers 256 thereby prevent flailing of the prosthetic element 255 toward the left atrium (like the chordae tendineae do for the native leaflets), so as to maintain the prosthetic element 255 in a position and orientation effective for augmenting the sealing of native posterior leaflet.

While the anchor assembly 200 is coupled with the native mitral valve 17 (e.g., refer to FIG. 24), the leaflets of the native mitral valve 17 (i.e., the native anterior leaflet 20 and the native posterior leaflet 22 (not visible in FIG. 24)) continue to cycle between open valve and closed valve configurations. While the leaflets are in the closed valve configuration as shown in FIG. 24, at least a portion of the prosthetic element 255 is positioned along the coaptation line defined between the free edges of the native leaflets 20 and 22. The prosthetic element 255 thereby enhances the seal between the leaflets 20 and 22.

Referring to FIGS. 25-28, in some embodiments the anchor assembly 200 includes another exemplary type of prosthetic element 257 that augments the native valve leaflets to enhance the sealing function of the native mitral valve 17 during the deployment of the prosthetic mitral valve assemblies described herein. In particular, the prosthetic element 257 includes three separate portions 257a, 257b, and 257c that augment the functioning of the native posterior leaflet 22.

Figure 25:
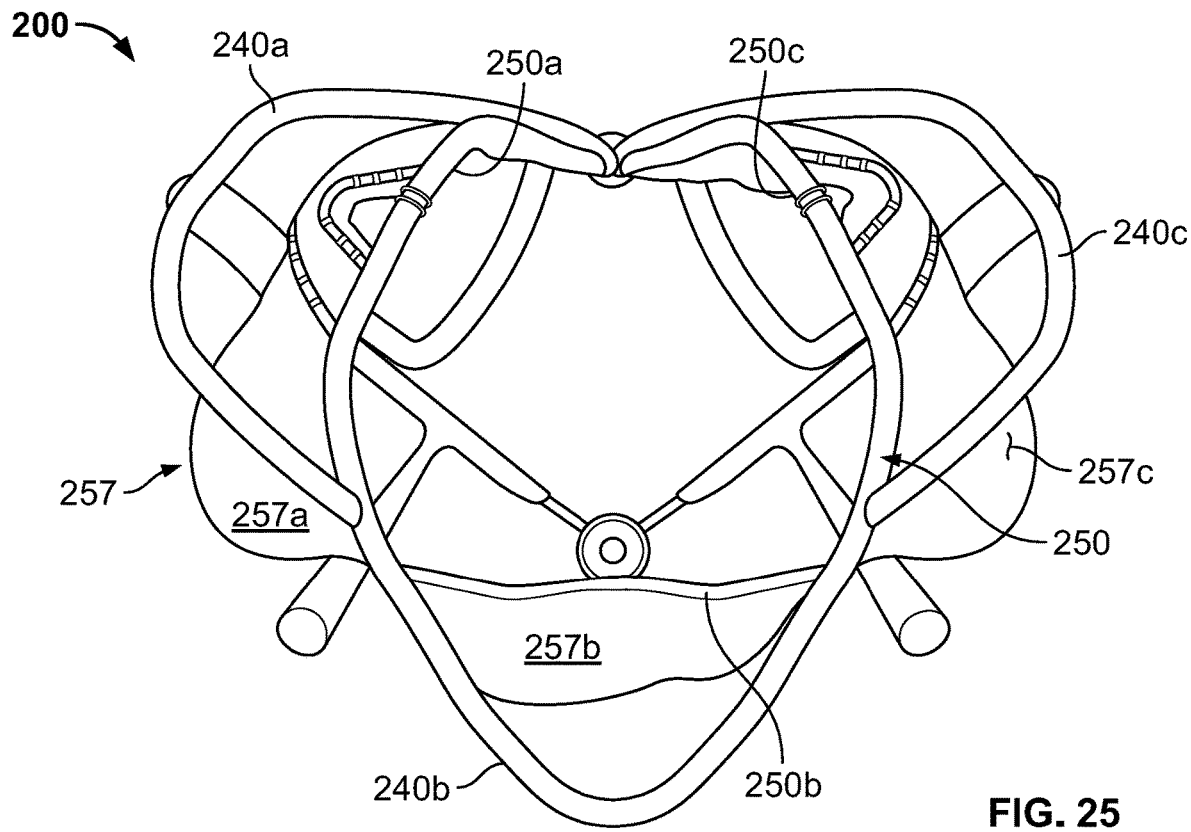
FIG. 25 shows a top view of another example anchor assembly that includes prosthetic elements for leaflet augmentation. The prosthetic elements are arranged in an open configuration.
Figure 26:
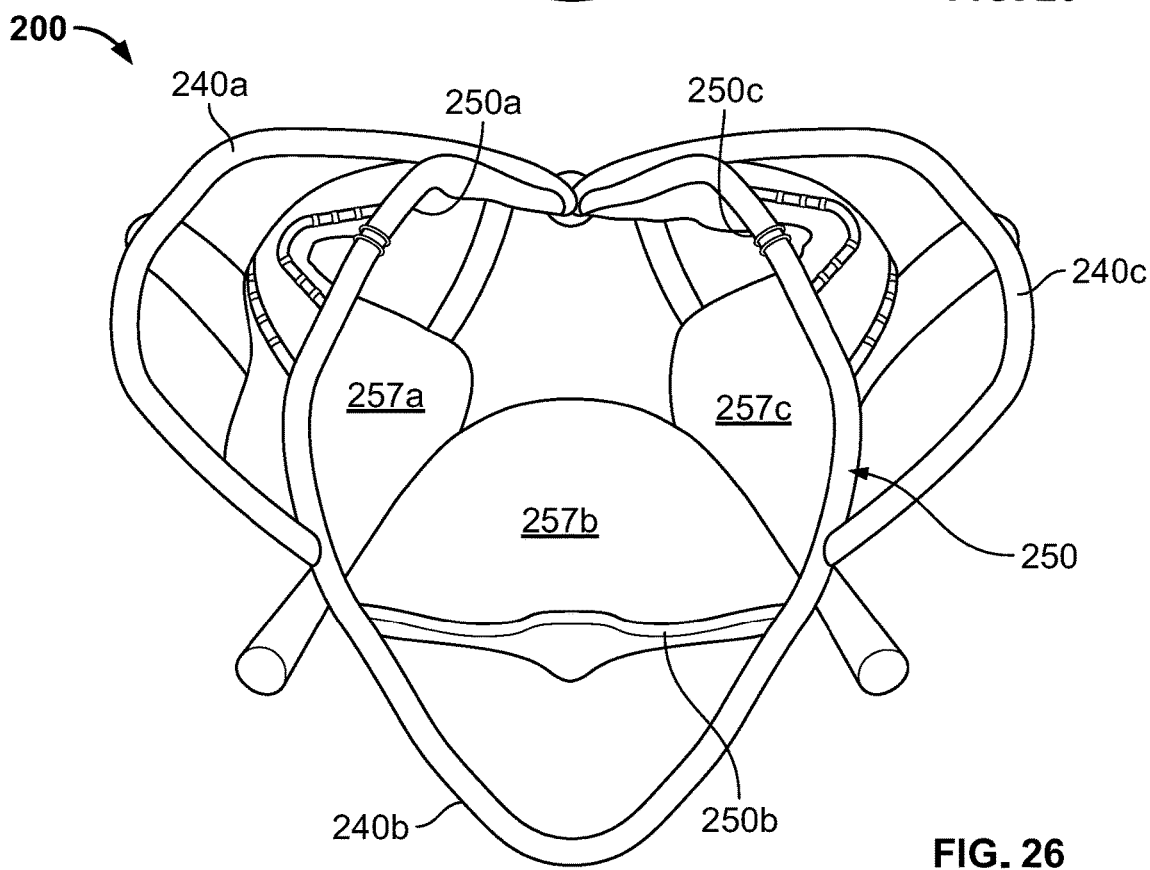
FIG. 26 shows a top view of the anchor assembly of FIG. 25 with the prosthetic elements arranged in a closed configuration.
Figure 27:
FIG. 27 shows the anchor assembly of FIG. 25 implanted in a native mitral valve and with the prosthetic elements arranged in an open configuration.
Figure 28:
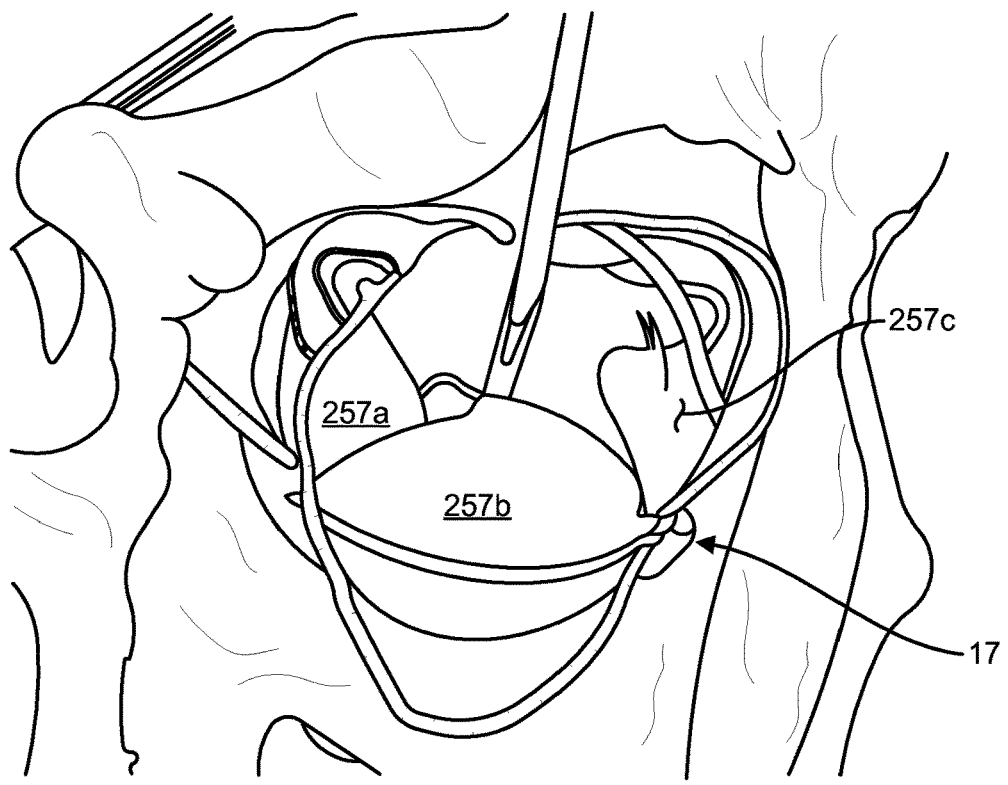
FIG. 28 shows the anchor assembly of FIG. 25 implanted in a native mitral valve and with the prosthetic elements arranged in a closed configuration.

FIGS. 25 and 27 show the prosthetic element 257 in an open configuration that facilitates flow through the native mitral valve 17. FIGS. 26 and 28 show the prosthetic element 257 in a coaptation configuration that facilitates a sealed closure of the native mitral valve 17 by augmenting the native posterior leaflet 22.

Similar to the prosthetic element 255 described in reference to FIGS. 22-24, the prosthetic element 257 is attached to a portion of the supra-annular ring 250. In the depicted embodiment, the portion 257b is attached via sutures and spans across the base of the posterior anchor arch 250b, the portion 257a is attached via sutures and spans across the base of the lateral anterior anchor arch 250a, and the portion 257c is attached via sutures and spans across the base of the medial anterior anchor arch 250c. In addition, in some embodiments the portion 257b is sewn to the lateral posterior inter-annular connection 270b and the medial posterior inter-annular connection 270c; the portion 257a is sewn to the lateral posterior inter-annular connection 270b and the lateral anterior inter-annular connection 270a; and the portion 257c is sewn to the medial posterior inter-annular connection 270c and the medial anterior inter-annular connection 270d. As such, the prosthetic element 257 is configured to essentially mimic the position and functioning of the native posterior leaflet 22.

In the depicted embodiment, the prosthetic element 257 is made of ePTFE. In some embodiments, the prosthetic element 257 is made of other materials such as any of the materials described above in reference to the prosthetic element 255.

In the depicted embodiment, the portions 257a, 257b, and 257c are separate from each other. That is, the portions 257a, 257b, and 257c are not connected directly to each other. In some embodiments, the portions 257a, 257b, and 257c may be connected to each other such as by suturing, the use of clips, and the like. In some embodiments, the prosthetic element 257 is a single, continuous member.

In the depicted embodiment, the extent or distance that the prosthetic element 257 can deflect in a superior direction (towards the left atrium) is not mechanically limited through the use of a constraint such as a tether, for example. Rather, the shape and material characteristics of the portions 257a, 257b, and 257c inherently maintain the portions 257a, 257b, and 257c in positions and orientations effective for coaptation with the native anterior leaflet 20. In use, the portions 257a, 257b, and 257c can billow inwardly and outwardly to facilitate sealing of the mitral valve and flow through the mitral valve respectively.

Figure 29:
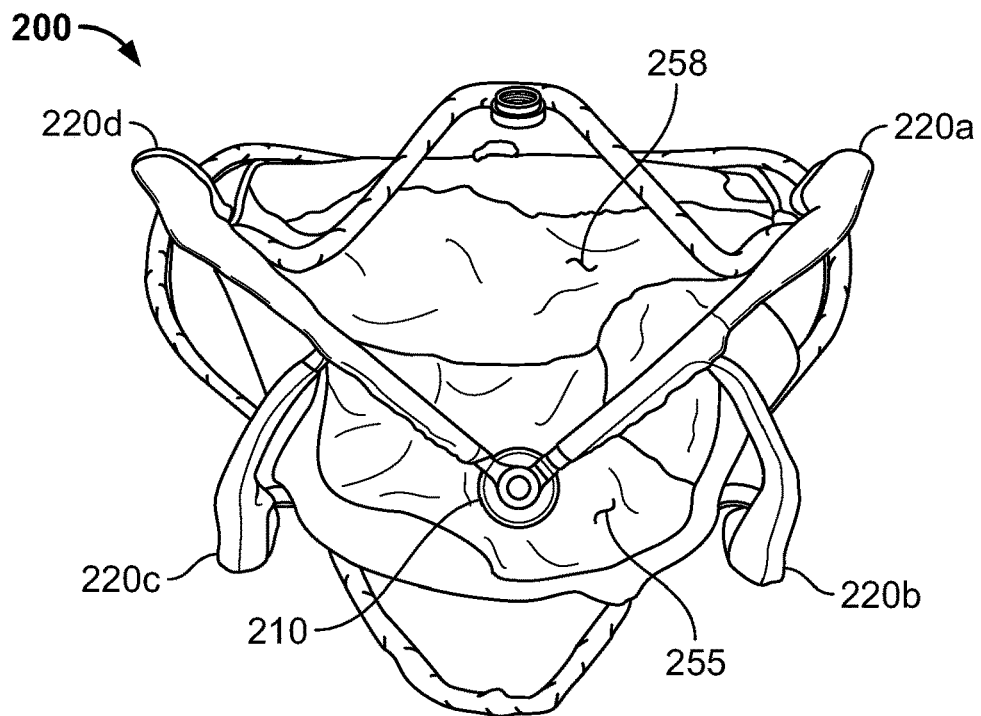
FIG. 29 shows a bottom view of an example anchor assembly that includes four prosthetic leaflets that configure the anchor assembly to function as a prosthetic valve.
Figure 30:
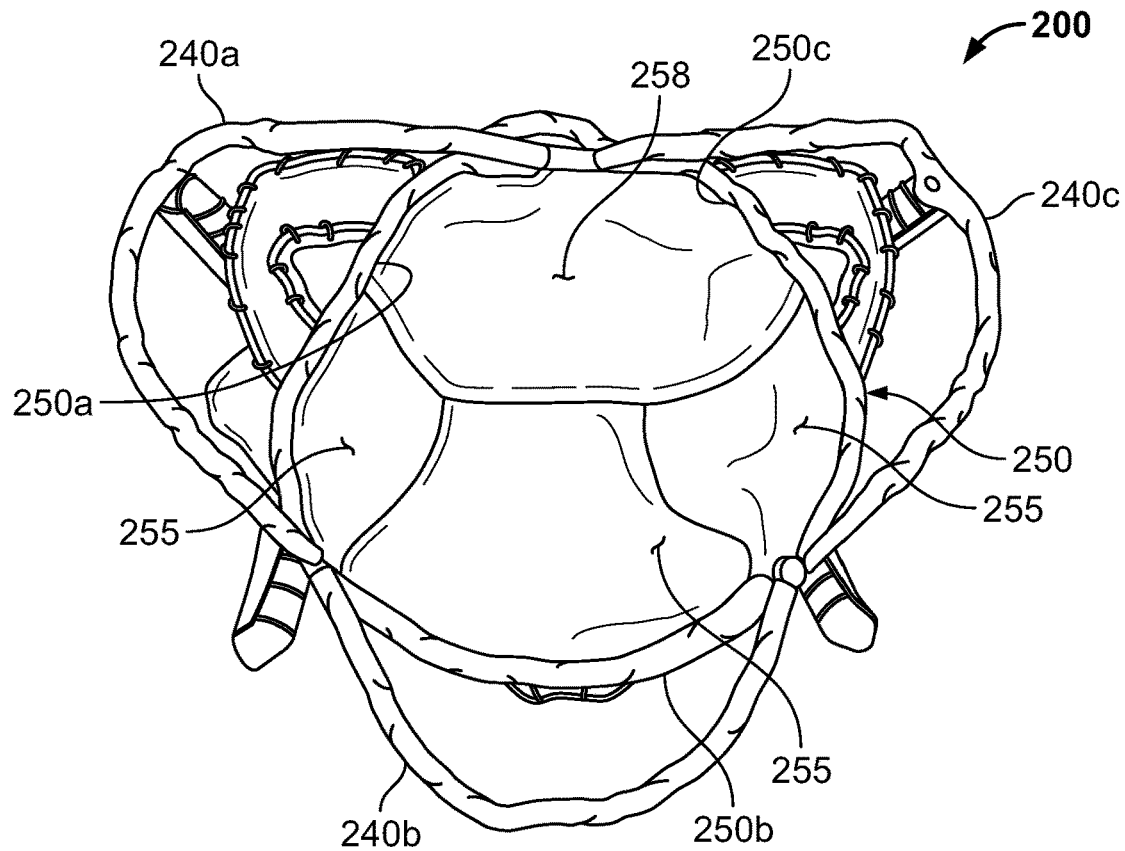
FIG. 30 shows a top view of the anchor assembly of FIG. 29.

Referring to FIGS. 29 and 30, whereas the embodiments of FIGS. 22-28 provide augmentation of the native posterior leaflet solely, in some embodiments the anchor assembly 200 includes a fully-circumferential arrangement of prosthetic elements that can mimic the function of a complete mitral valve. For example, in the embodiment depicted in FIGS. 29 and 30 the anchor assembly 200 includes a prosthetic element 255 and a prosthetic element 258 that together form a fully-circumferential arrangement of prosthetic elements. Accordingly, like a native mitral valve, the free edges of the prosthetic elements 255 and 258 can coapt with each other to occlude blood flow through the native mitral valve, and the free edges of the prosthetic elements 255 and 258 can separate from each other to allow blood flow through the native mitral valve.

In the depicted embodiment, the prosthetic element 255 is configured as described above in reference to FIGS. 22-24. That is, the prosthetic element 255 is attached via sutures and spans across the base of the posterior anchor arch 250b, and partially to the base of the lateral anterior anchor arch 250a and the medial anterior anchor arch 250c. The prosthetic element 258 is attached via sutures and partially spans across the base of the lateral anterior anchor arch 250a and the medial anterior anchor arch 250c to which the prosthetic element 255 is not attached. Accordingly, the prosthetic element 255 mimics the native posterior leaflet 22 (FIG. 12) and the prosthetic element 258 mimics the native anterior leaflet 20.

In the depicted embodiment, the deflections of the free edges of the prosthetic elements 255 and 258 are not mechanically constrained. In some embodiments, mechanical constraints (e.g., tethers) are included to limit the deflection or travel of the free edges of the prosthetic elements 255 and/or 258.

The prosthetic elements 255 and/or 258 can be made of any of the materials and can include any of the features described above in reference to prosthetic elements 255 and 257.

While the anchor assembly 200 that includes the prosthetic elements 255 and 258 is in use (i.e., implanted in engagement with a native mitral valve), the native leaflets of the native mitral valve will continue to open and close in the typical fashion of a mitral valve. Additionally, the prosthetic elements 255 and 258 will move between opened and closed configurations synchronously with the native leaflets. In such a manner, the prosthetic elements 255 and 258 can serve to enhance the sealing provided by the native leaflets to thereby mitigate valvular regurgitation.

Figure 31:
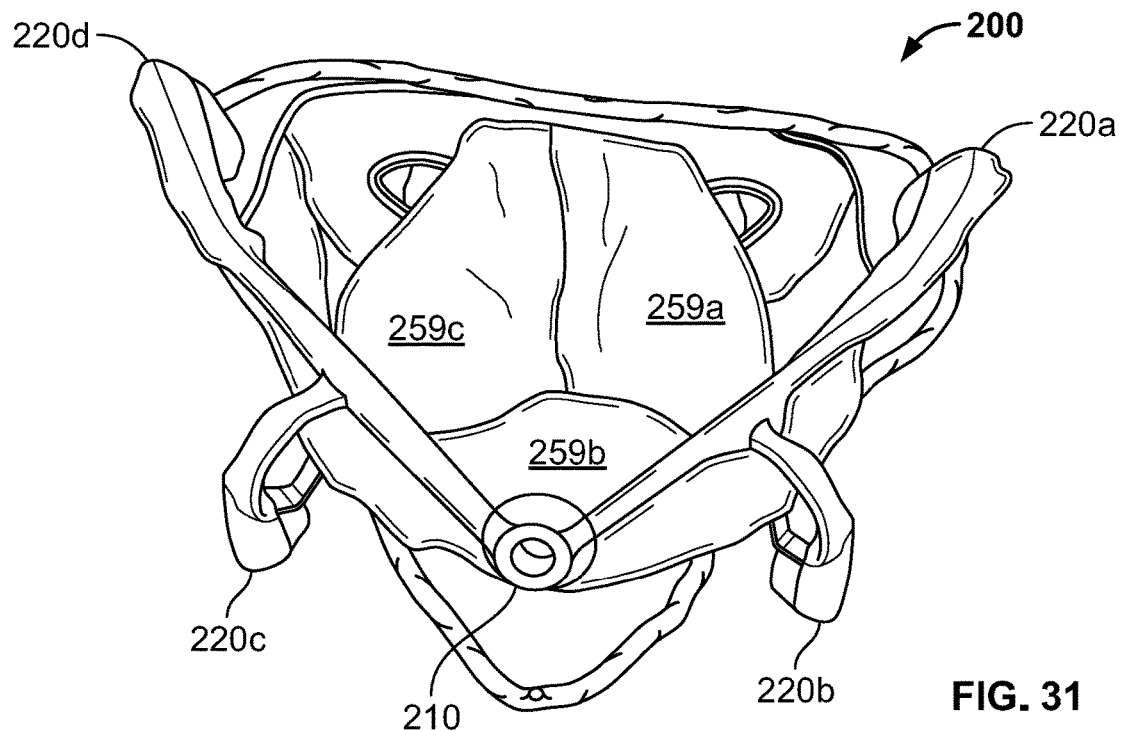
FIG. 31 shows a bottom view of an example anchor assembly that includes three prosthetic leaflets that configure the anchor assembly to function as a prosthetic valve.
Figure 32:
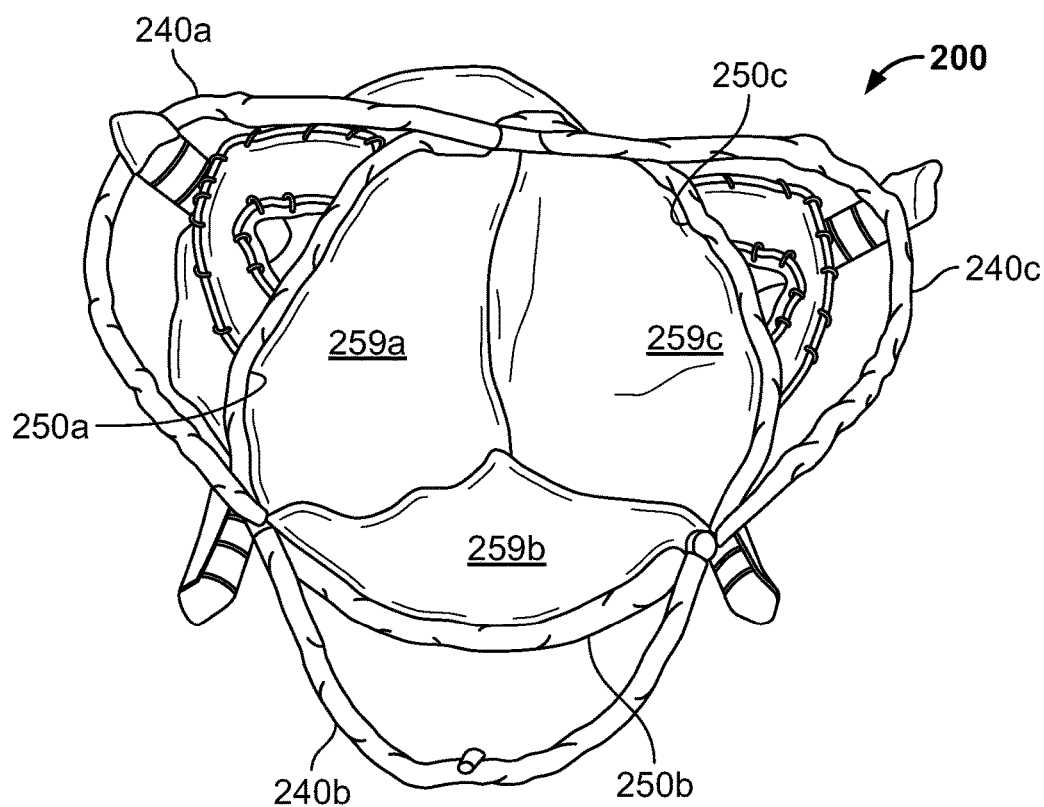
FIG. 32 shows a top view of the anchor assembly of FIG. 31.

Referring to FIGS. 31 and 32, in some embodiments the anchor assembly 200 can be configured with a tri-leaflet, fully-circumferential arrangement of prosthetic elements that can mitigate MR by mimicking the function of a complete mitral valve. For example, the depicted embodiment of anchor assembly 200 includes a fully-circumferential arrangement of prosthetic elements that includes leaflet 259a, leaflet 259b, and leaflet 259c.

In the depicted embodiment, the leaflets 259a, 259b, and 259c are not directly attached to each other. The free edges of the leaflets 259a, 259b, and 259c can coapt with each other to occlude blood flow through the native mitral valve, and can separate from each other to allow blood flow through the native mitral valve. As such, the leaflets 259a, 259b, and 259c are configured to function like a complete native heart valve.

The leaflets 259a, 259b, and 259c can be made of any of the materials and can include any of the features described above in reference to prosthetic elements 255 and 257.

In the depicted embodiment, the leaflet 259a is sutured to an entirety of the lateral anterior anchor arch 250a, the leaflet 259b is sutured to an entirety of the posterior anchor arch 250b, and the leaflet 259c is sutured to an entirety of the medial anterior anchor arch 250c. Accordingly, in the depicted embodiment each of the leaflets 259a, 259b, and 259c is attached along about 120° of the circumference of the supra-annular ring 250 (which is comprised of the lateral anterior anchor arch 250a, the posterior anchor arch 250b, and the medial anterior anchor arch 250c). In some embodiments, the leaflets 259a, 259b, and 259c are attached to the supra-annular ring 250 by differing degrees (e.g., 100°, 100°, and 160°; and other such differing arrangements without limitation).

In the depicted embodiment, the deflections of the free edges of the leaflets 259a, 259b, and 259c are not mechanically constrained. In some embodiments, mechanical constraints (e.g., tethers) are included to limit the deflection or travel of the free edges of the leaflets 259a, 259b, and/or 259c.

Figure 34:
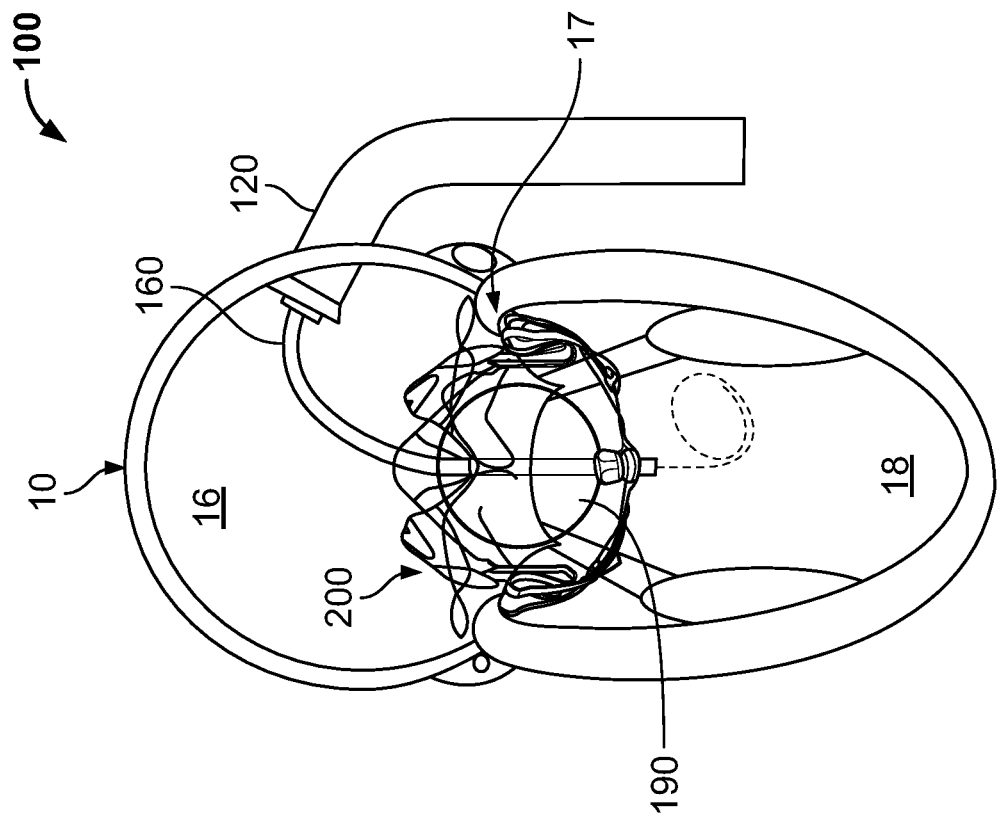
FIG. 34 shows the arrangement of FIG. 33 with an inflatable device expanded within the anchor assembly to provide a temporary spacer that enhances the sealing function provided by the native valve leaflets.
Figure 33:
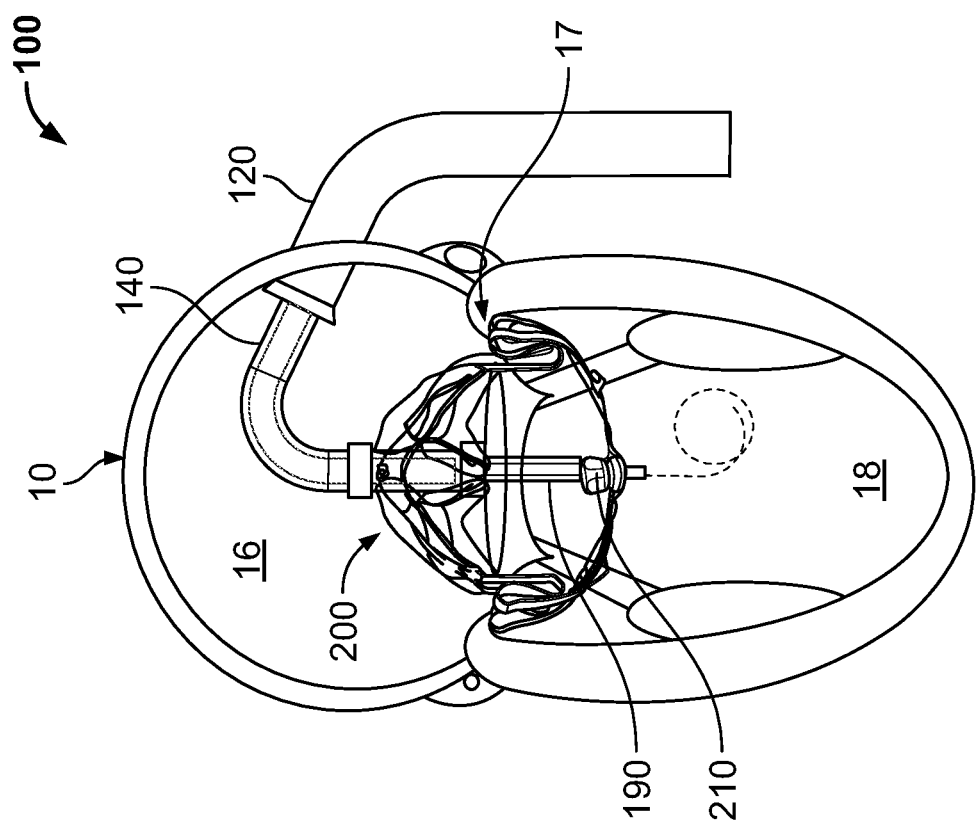
FIG. 33 shows a commissural cross-sectional view of a heart with the anchor assembly of FIG. 7 being deployed within the native mitral valve.

Referring to FIGS. 33 and 34, in some embodiments a space-filling element can be used to mitigate the potential for temporary MR after the implantation of the anchor assembly 200 (but prior to the implantation of a valve assembly as described further below). For example, in the depicted embodiment the transcatheter mitral valve delivery system 100 includes an inflatable element 190 that is selectively expandable (e.g., inflatable and deflatable) to occupy open space between the free edges of the native leaflets that may exist as a result of incomplete coaptation of the native valve leaflets after the anchor assembly 200 is implanted.

The inflatable element 190 is depicted in a deflated (contracted) configuration in FIG. 33, and depicted in an inflated (expanded) configuration in FIG. 34.

FIGS. 33 and 34 correspond to FIGS. 9-11 described above, but with the addition of the inflatable element 190 coupled to the inner catheter 160. In addition, in some embodiments no guidewire 110 is used in the arrangement depicted in FIGS. 33 and 34. In such a case, the lumen of the inner catheter 160 that would otherwise be occupied by the guidewire can be used instead as an inflation lumen for the inflatable element 190. Alternatively, in some embodiments a guidewire is used and a separate lumen of the inner catheter 160 is used as an inflation lumen for the inflatable element 190.

In some embodiments, the inflatable element 190 (when inflated) is spherically-shaped with a diameter of about 25 mm to about 35 mm, or about 20 mm to about 30 mm, or about 30 mm to about 40 mm, without limitation. In some embodiments, the inflatable element 190 (when inflated) is non-spherically-shaped. For example, in some embodiments the inflatable element 190 (when inflated) is conical, spool-shaped, elliptically-shaped, shaped to approximate the natural line of coaptation between native mitral valve leaflets, and the like.

In some embodiments, the inflatable element 190 is comprised of a urethane material with a thin wall such that the inflatable element 190 is highly compliant. Other materials may also be used to make the inflatable element 190 such as, but not limited to, latex, silicone, PET, and the like.

After the implantation of the anchor assembly 200 within the native mitral valve 17 (as performed, for example, in accordance with FIGS. 1-5, 7-11, 33, and 34), a valve delivery catheter 180 of the delivery system 100 can be used to deploy a valve assembly within the anchor assembly 200 (as described further below). Prior to deployment of the valve assembly, the inflatable element 190 is deflated to the configuration of FIG. 33. In some embodiments, after the deflation of the inflatable element 190, the valve delivery catheter 180 is advanced over the inner catheter 160 and over the deflated inflatable element 190.

Figure 35:
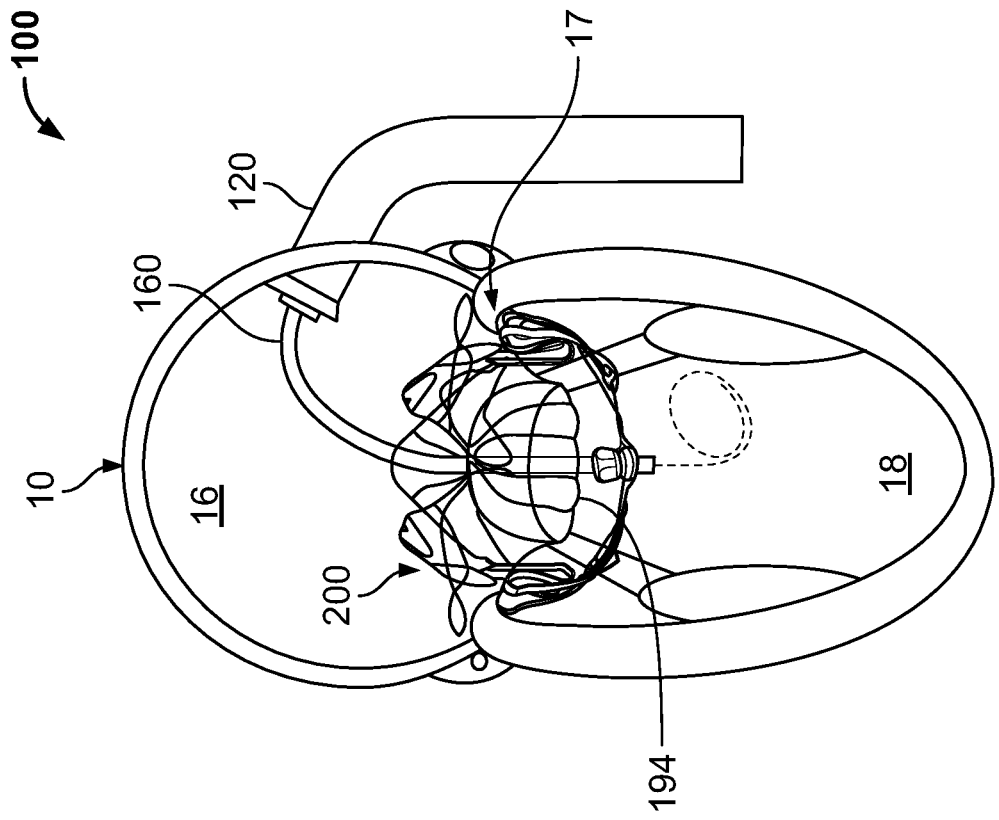
FIG. 35 shows a commissural cross-sectional view of a heart with the anchor assembly of FIG. 7 being deployed within the native mitral valve.
Figure 36:
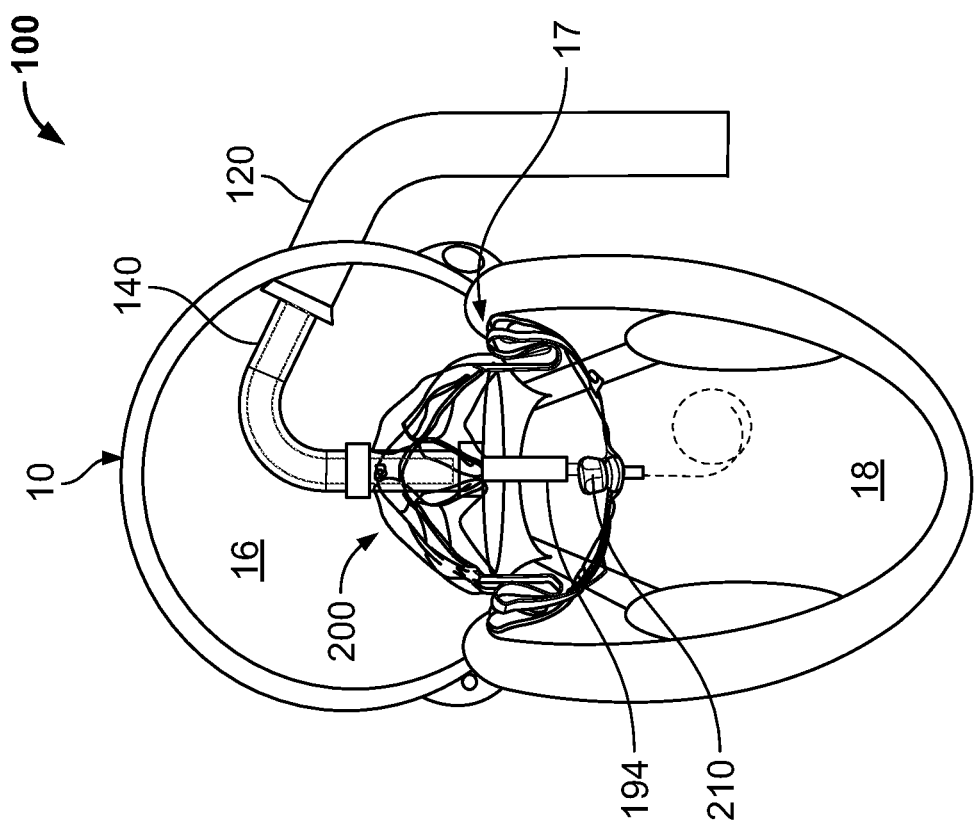
FIG. 36 shows the arrangement of FIG. 35 with a wire-framed, self-expanding device expanded within the anchor assembly to provide a temporary spacer that enhances the sealing function provided by the native valve leaflets.

Referring to FIGS. 35 and 36, in some embodiments a self-expanding space-filling element 194 can be used to mitigate the potential for temporary MR after the implantation of the anchor assembly 200 (but prior to the implantation of a valve assembly as described further below). The self-expanding space-filling element 194 can occupy open space between the free edges of the native leaflets that may exist as a result of incomplete coaptation of the native valve leaflets after the anchor assembly 200 is implanted. The self-expanding space-filling element 194 can also act as a deflector, deflecting the central MR jet back into the left ventricle. The self-expanding space-filling element 194 is depicted in a diametrically-constrained (contracted) configuration in FIG. 35, and depicted in an unconstrained (expanded) configuration in FIG. 36.

FIGS. 35 and 36 correspond to FIGS. 9-11 described above, but with the addition of the self-expanding space-filling element 194 coupled to the inner catheter 160. In the depicted embodiment, the self-expanding space-filling element 194 is coupled to the outer diameter of the inner catheter 160 along a distal end portion of the inner catheter 160. One or more catheters (e.g., steerable catheter 150) that are over the inner catheter 160 can be used to diametrically constrain the self-expanding space-filling element 194. When the constraining catheter is pulled proximally in relation to the inner catheter 160, the self-expanding space-filling element 194 will emerge and self-expand to the configuration shown in FIG. 36.

In some embodiments, the self-expanding space-filling element 194 comprises a wire-framed construct with a flexible material covering the frame. For example, in some embodiments a nitinol wire framework is used to provide the structure and shape of the self-expanding space-filling element 194. The nitinol frame may be made, for example, by laser-cutting and expanding a nitinol tube (and then heat-setting the expanded tube in the desired, expanded shape). In some embodiments, one or more nitinol wires may be wound or woven to provide the desired, expanded shape.

In some embodiments, the expanded shape of the self-expanding space-filling element 194 is generally cylindrical. In some embodiments, the self-expanding space-filling element 194 (when expanded) is cylindrically-shaped with a diameter of about 25 mm to about 35 mm, or about 20 mm to about 30 mm, or about 30 mm to about 40 mm, without limitation. In some embodiments, the self-expanding space-filling element 194 can be configured to expand to a non-cylindrical shape such as, but not limited to, conical, spool-shaped, elliptically-shaped, spherical, shaped to approximate the natural line of coaptation between native mitral valve leaflets, and the like.

In some embodiments, the flexible covering material of the self-expanding space-filling element 194 is comprised of a urethane material with a thin wall such that the self-expanding space-filling element 194 is highly compliant. Other materials may also be used to make the self-expanding space-filling element 194 such as, but not limited to, latex, silicone, PET, ePTFE, PTFE, a polyester, ELAST-EON™ (a silicone and urethane polymer), another biocompatible polymer, DACRON®, copolymers, or combinations and subcombinations thereof.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the valve delivery catheter 180 is advanced over the inner catheter 160 and over the self-expanding space-filling element 194. The valve delivery catheter 180 will contract the self-expanding space-filling element 194 as the valve delivery catheter 180 is advanced over the self-expanding space-filling element 194.

Figure 38:
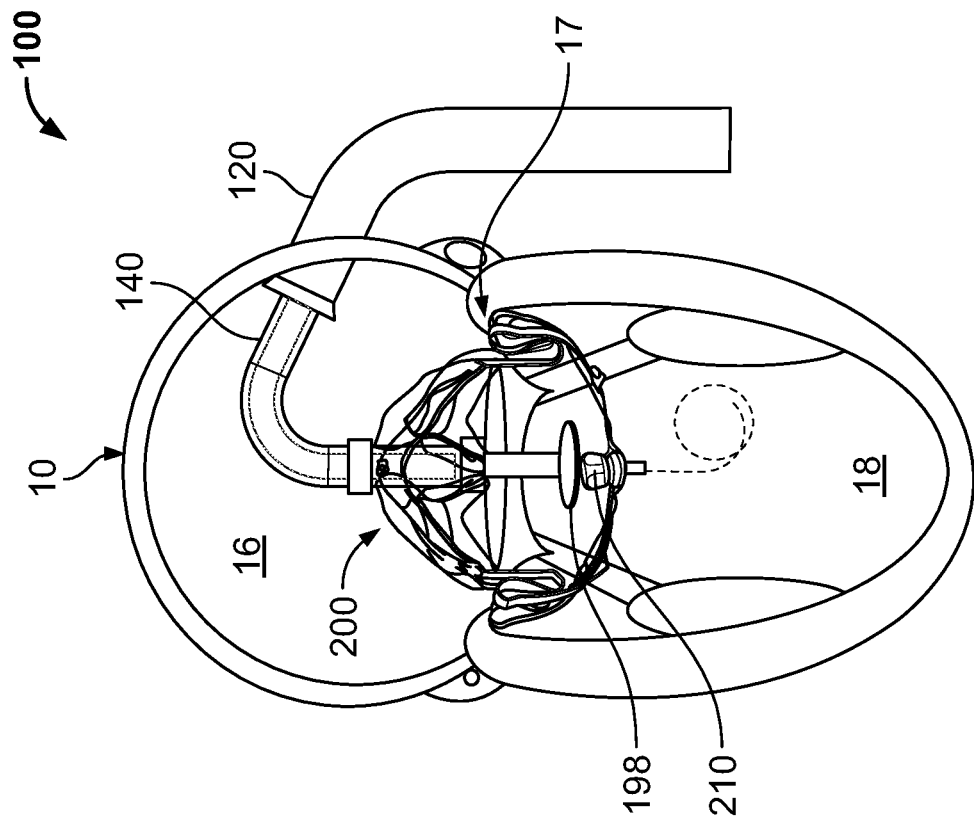
FIG. 38 shows the arrangement of FIG. 37 with a passively-expandable, sock-like device expanded within the anchor assembly to provide a temporary spacer that enhances the sealing function provided by the native valve leaflets.

Referring to FIGS. 37 and 38, in some embodiments a passively-expanding space-filling element 198 can be used to mitigate the potential for temporary MR after the implantation of the anchor assembly 200 (but prior to the implantation of a valve assembly as described further below). The passively-expanding space-filling element 198 can occupy open space between the free edges of the native leaflets that may exist as a result of incomplete coaptation of the native valve leaflets after the anchor assembly 200 is implanted. The passively-expanding space-filling element 198 can also act as a deflector, deflecting the central MR jet back into the left ventricle. The passively-expanding space-filling element 198 is depicted in an axially and/or diametrically-constrained (contracted) configuration in FIG. 37, and depicted in an unconstrained (expanded) configuration in FIG. 38.

FIGS. 37 and 38 correspond to FIGS. 9-11 described above, but with the addition of the passively-expanding space-filling element 198 coupled to the inner catheter 160. In the depicted embodiment, the passively-expanding space-filling element 198 is coupled to the outer diameter of the inner catheter 160 along a distal end portion of the inner catheter 160. One or more catheters (e.g., steerable catheter 150) that are over the inner catheter 160 can be used to axially and/or diametrically constrain the passively-expanding space-filling element 198. When the constraining catheter is pulled proximally in relation to the inner catheter 160, the passively-expanding space-filling element 198 will emerge. Thereafter, blood from the MR can fill the interior space defined by the passively-expanding space-filling element 198 to expand the passively-expanding space-filling element 198 to the configuration shown in FIG. 36. Such a filling and expanding can be compared, for example, to the wind filling or inflating a wind sock.

In some embodiments, the passively-expanding space-filling element 198 comprises a wire-framed construct and a flexible material. For example, in some embodiments a nitinol wire framework is used to provide the structure and shape of the mouth of the passively-expanding space-filling element 198 (at the distal end of the passively-expanding space-filling element 198). The nitinol frame may be made, for example, by laser-cutting and expanding a nitinol tube (and then heat-setting the expanded tube in the desired, expanded shape). In some embodiments, one or more nitinol wires may be wound or woven to provide the desired, expanded shape.

In some embodiments, the expanded shape of the passively-expanding space-filling element 198 is generally conical. In some embodiments, the passively-expanding space-filling element 198 (when expanded) is conically-shaped with an average diameter of about 25 mm to about 35 mm, or about 20 mm to about 30 mm, or about 30 mm to about 40 mm, without limitation. In some embodiments, the passively-expanding space-filling element 198 can be configured to expand to a non-conical shape such as, but not limited to, cylindrical, spool-shaped, elliptically-shaped, spherical, shaped to approximate the natural line of coaptation between native mitral valve leaflets, and the like.

In some embodiments, the flexible material of the passively-expanding space-filling element 198 is comprised of a urethane material with a thin wall such that the passively-expanding space-filling element 198 is highly compliant. Other materials may also be used to make the passively-expanding space-filling element 198 such as, but not limited to, latex, silicone, PET, ePTFE, PTFE, a polyester, ELAST-EON™ (a silicone and urethane polymer), another biocompatible polymer, DACRON®, copolymers, or combinations and subcombinations thereof.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the valve delivery catheter 180 is advanced over the inner catheter 160 and over the passively-expanding space-filling element 198. The valve delivery catheter 180 will contract the passively-expanding space-filling element 198 as the valve delivery catheter 180 is advanced over the passively-expanding space-filling element 198.

Figure 40:
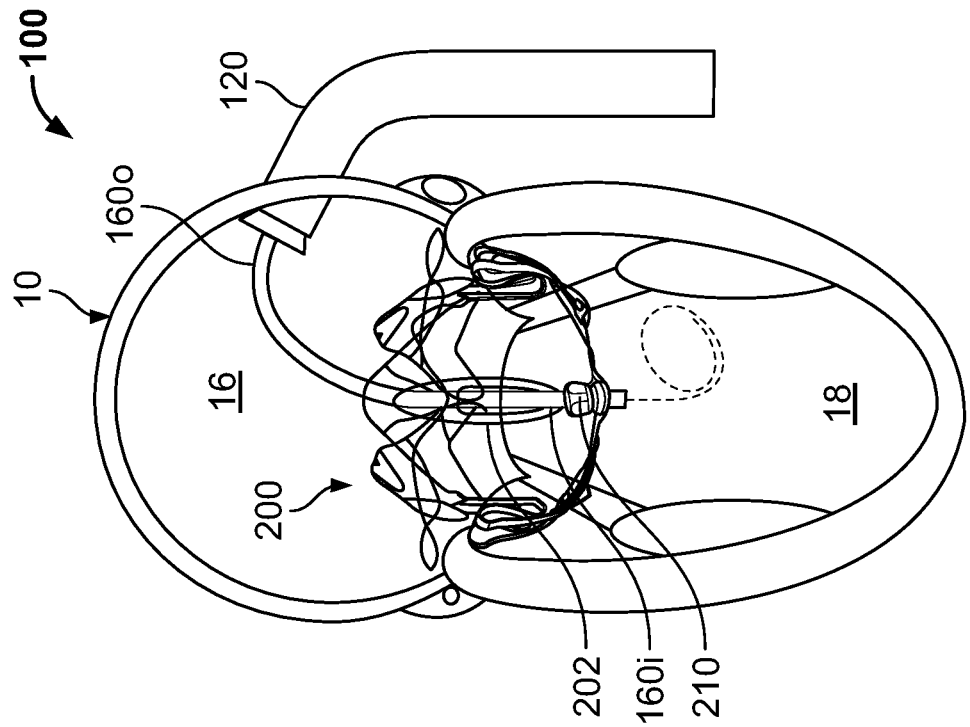
FIG. 40 shows the arrangement of FIG. 39 with the wire-framed, expandable device collapsed within the anchor assembly.
Figure 39:
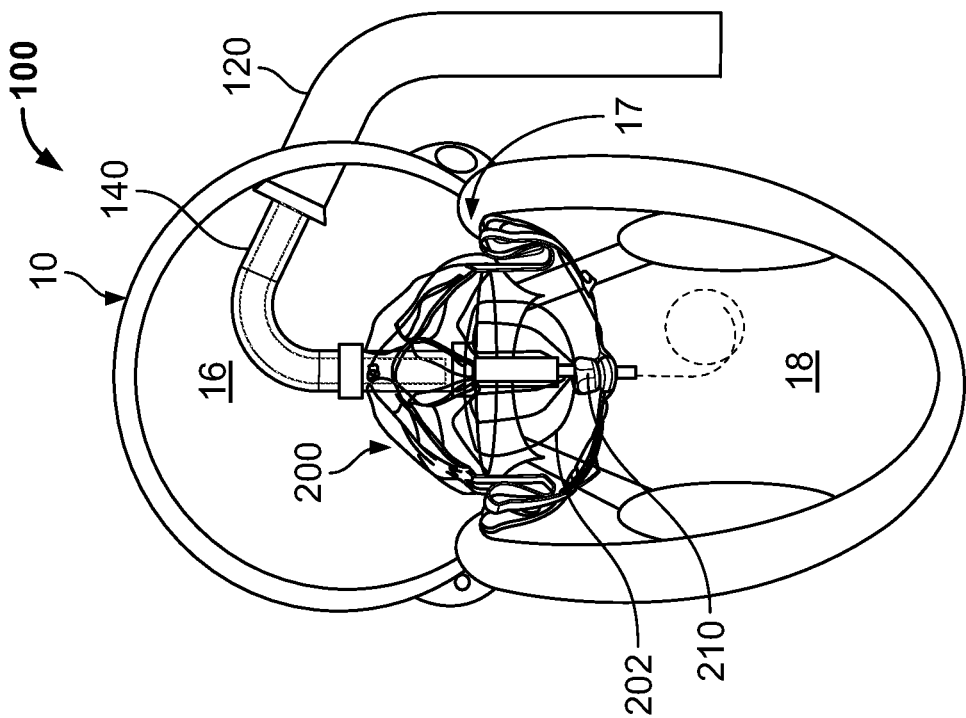
FIG. 39 shows a commissural cross-sectional view of a heart with the anchor assembly of FIG. 7 being deployed within the native mitral valve, with a wire-framed, expandable device expanded within the anchor assembly to provide a temporary spacer that enhances the sealing function provided by the native valve leaflets.

Referring to FIGS. 39 and 40, in some embodiments a wire-framed, expandable device 202 can be used to mitigate the potential for temporary MR after the implantation of the anchor assembly 200 (but prior to the implantation of a valve assembly as described further below). The wire-framed, expandable device 202 can occupy open space between the free edges of the native leaflets that may exist as a result of incomplete coaptation of the native valve leaflets after the anchor assembly 200 is implanted. The wire-framed, expandable device 202 can also act as a deflector, deflecting the central MR jet back into the left ventricle. The wire-framed, expandable device 202 is depicted in an unconstrained (expanded) configuration in FIG. 39, and depicted in a diametrically-constrained (contracted) configuration in FIG. 40.

FIGS. 39 and 40 correspond to FIGS. 9-11 described above, but with the addition of the wire-framed, expandable device 202 coupled to a two-part inner catheter. The two-part inner catheter can be considered substantially analogous to the inner catheter 160 described above, but with a two-part construction (an inner catheter member and an outer catheter member). That is, the two-part inner catheter includes an interior inner catheter 160i and an exterior inner catheter 160o. The interior inner catheter 160i is slidably disposed within a lumen defined by the exterior inner catheter 160o.

In the depicted embodiment, a distal end portion of the wire-framed, expandable device 202 is coupled to a distal end portion of the interior inner catheter 160i. Further, a proximal end portion of the wire-framed, expandable device 202 is coupled to a distal end portion of the exterior inner catheter 160o. One or more control wires, for example, can be used to couple the wire-framed, expandable device 202 to the exterior inner catheter 160o and the interior inner catheter 160i. The interior inner catheter 160i and exterior inner catheter 160o can be coaxially arranged, and movable, in relation to one another to controllably cause expansion and collapse of the wire-framed, expandable device 202. For example, distal axial movement of the exterior inner catheter 160o in relation to the interior inner catheter 160i, or proximal axial movement of the interior inner catheter 160i in relation to the exterior inner catheter 160o, causes or allows the wire-framed, expandable device 202 to longitudinally shorten and radially expand. Alternatively, proximal axial movement of the exterior inner catheter 160o in relation to the interior inner catheter 160i, or distal axial movement of the interior inner catheter 160i in relation to the exterior inner catheter 160o, causes the wire-framed, expandable device 202 to longitudinally elongate and radially collapse.

One or more catheters (e.g., guide catheter 120) that are over the interior inner catheter 160i and the exterior inner catheter 160o can be used to diametrically constrain the wire-framed, expandable device 202 during delivery into the heart 10. When the constraining catheter is pulled proximally in relation to the exterior inner catheter 160o, the wire-framed, expandable device 202 will emerge, and then self-expand to the configuration shown in FIG. 39. Alternatively, the wire-framed, expandable device 202 can remain in the collapsed configuration as shown in FIG. 40, until the interior inner catheter 160i or the exterior inner catheter 160o are moved in relation to one another to actively expand the wire-framed, expandable device 202 or to allow self-expansion of the wire-framed, expandable device 202.

In some embodiments, the wire-framed, expandable device 202 comprises a wire-framed construct with a flexible material covering the frame. For example, in some embodiments a nitinol wire framework is used to provide the structure and shape of the wire-framed, expandable device 202. The nitinol frame may be made, for example, by laser-cutting and expanding a nitinol tube (and then heat-setting the expanded tube in the desired, expanded shape). In some embodiments, one or more nitinol wires may be wound or woven to provide the desired, expanded shape.

In some embodiments, the expanded shape of the wire-framed, expandable device 202 is generally cylindrical. In some embodiments, the wire-framed, expandable device 202 (when expanded) is cylindrically-shaped with a diameter of about 25 mm to about 35 mm, or about 20 mm to about 30 mm, or about 30 mm to about 40 mm, without limitation. In some embodiments, the wire-framed, expandable device 202 can be configured to expand to a non-cylindrical shape such as, but not limited to, conical, spool-shaped, elliptically-shaped, spherical, crescent-shaped, shaped to approximate the natural line of coaptation between native mitral valve leaflets, and the like.

In some embodiments, the flexible covering material of the wire-framed, expandable device 202 is comprised of a urethane material with a thin wall such that the wire-framed, expandable device 202 is highly compliant. Other materials may also be used to make the wire-framed, expandable device 202 such as, but not limited to, latex, silicone, PET, ePTFE, PTFE, a polyester, ELAST-EON™ (a silicone and urethane polymer), another biocompatible polymer, DACRON®, copolymers, or combinations and subcombinations thereof.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the valve delivery catheter 180 is advanced over the exterior inner catheter 160o and over the wire-framed, expandable device 202. In some embodiments, the valve delivery catheter 180 will contract the wire-framed, expandable device 202 as the valve delivery catheter 180 is advanced over the wire-framed, expandable device 202. Alternatively, the wire-framed, expandable device 202 can be actively collapsed by relative axial movements of the interior inner catheter 160i and/or the exterior inner catheter 160o.

Figure 42:
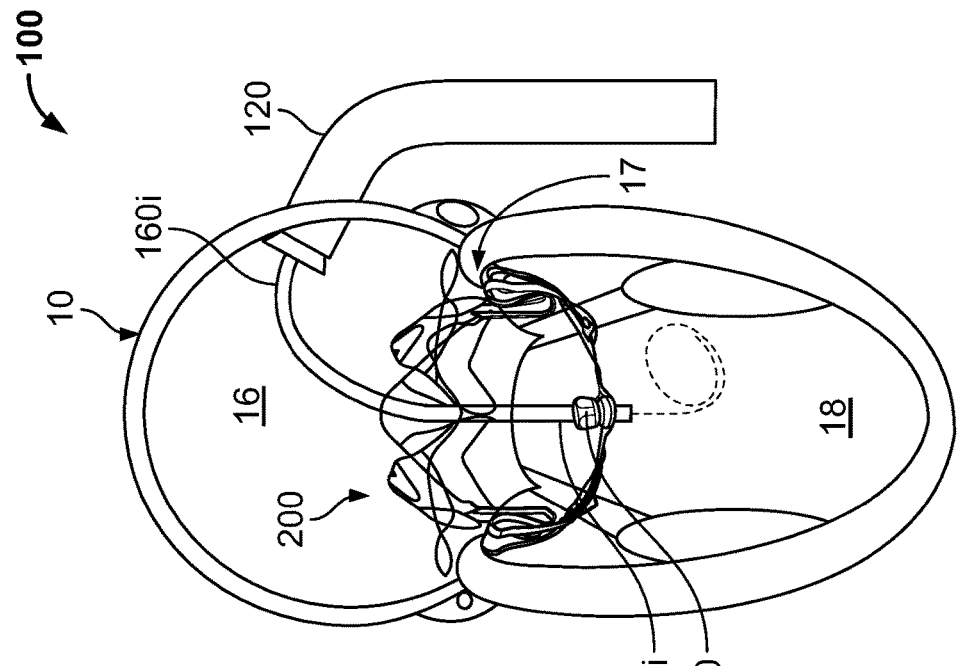
FIG. 42 shows the arrangement of FIG. 41 with the wire-framed, self-expanding device removed from the anchor assembly.
Figure 43:
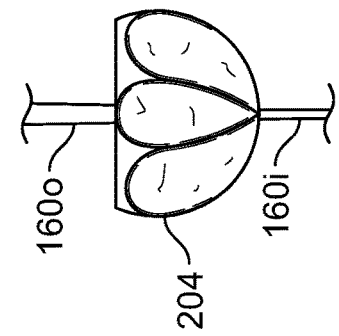
FIG. 43 shows the wire-framed, self-expanding device of FIG. 41 in an expanded position.
Figure 41:
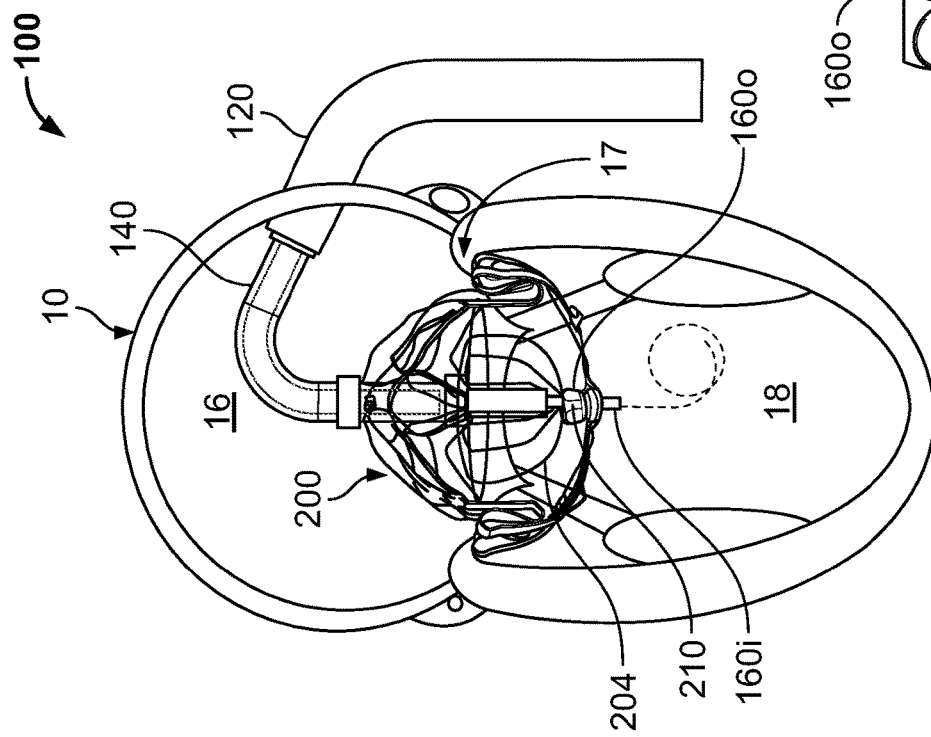
FIG. 41 shows a commissural cross-sectional view of a heart with the anchor assembly of FIG. 7 being deployed within the native mitral valve, with a wire-framed, self-expanding device expanded within the anchor assembly to provide a temporary spacer that enhances the sealing function provided by the native valve leaflets.

Referring to FIGS. 41, 42 and 43, in some embodiments a wire-framed, self-expanding device 204 can be used to mitigate the potential for temporary MR after the implantation of the anchor assembly 200 (but prior to the implantation of a valve assembly as described further below). The wire-framed, self-expanding device 204 can occupy open space between the free edges of the native leaflets that may exist as a result of incomplete coaptation of the native valve leaflets after the anchor assembly 200 is implanted. The wire-framed, self-expanding device 204 can also act as a deflector, deflecting the central MR jet back into the left ventricle. The wire-framed, expandable device 204 is depicted in an unconstrained (expanded) configuration in FIGS. 41 and 43, and is removed from view in FIG. 42.

FIGS. 41 and 42 correspond to FIGS. 9-11 described above, but with the addition of the wire-framed, self-expanding device 204 coupled to an exterior inner catheter 160o that surrounds an interior inner catheter 160i. In the depicted embodiment, a distal end portion of the wire-framed, self-expanding device 204 is coupled (e.g., for example, coupled using one or more control wires) to a distal end portion of the exterior inner catheter 160o. In addition, interior inner catheter 160i and exterior inner catheter 160o can be coaxially arranged, and movable in relation to one another, such that the wire-framed, self-expanding device 204 can be selectively moved via the exterior inner catheter 160o, with little to no movement of the interior inner catheter 160i.

One or more catheters (e.g., guide catheter 120) that are over the interior inner catheter 160i and the exterior inner catheter 160o can be used to diametrically constrain the wire-framed, self-expanding device 204. When the constraining catheter is pulled proximally in relation to the exterior inner catheter 160o, the wire-framed, self-expanding device 204 will emerge and can self-expand to the configuration shown in FIGS. 41 and 43. Other catheters (e.g., anchor delivery catheter 140) can nest inside the wire-framed, self-expanding device 204 when the wire-framed, self-expanding device 204 is in an expanded configuration.

In some embodiments, the wire-framed, self-expanding device 204 comprises a wire-framed construct with a flexible material covering the frame. For example, in some embodiments a nitinol wire framework is used to provide the structure and shape of the wire-framed, self-expanding device 204. The nitinol frame may be made, for example, by laser-cutting and expanding a nitinol tube (and then heat-setting the expanded tube in the desired, expanded shape). In some embodiments, one or more nitinol wires may be wound or woven to provide the desired, expanded shape.

In some embodiments, the expanded shape of the wire-framed, self-expanding device 204 is generally cylindrical. In some embodiments, the wire-framed, self-expanding device 204 (when expanded) is cylindrically-shaped with a diameter of about 25 mm to about 35 mm, or about 20 mm to about 30 mm, or about 30 mm to about 40 mm, without limitation. In some embodiments, the wire-framed, self-expanding device 204 can be configured to expand to a non-cylindrical shape such as, but not limited to, conical, spool-shaped, elliptically-shaped, spherical, shaped to approximate the natural line of coaptation between native mitral valve leaflets, and the like.

In some embodiments, the flexible covering material of the wire-framed, self-expanding device 204 is comprised of a urethane material with a thin wall such that the wire-framed, self-expanding device 204 is highly compliant. Other materials may also be used to make the wire-framed, self-expanding device 204 such as, but not limited to, latex, silicone, PET, ePTFE, PTFE, a polyester, ELAST-EON™ (a silicone and urethane polymer), another biocompatible polymer, DACRON®, copolymers, or combinations and subcombinations thereof.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the wire-framed, self-expanding device 204 is removed prior to advancement of the valve delivery catheter 180. For example, exterior inner catheter 160o that is coupled to the wire-framed, self-expanding device 204 can be withdrawn from the heart 10, while maintaining coupling between the interior inner catheter 160i and hub 210 of the anchor assembly 200. In some embodiments, the wire-framed, self-expanding device 204 can be withdrawn into anchor delivery catheter 140, guide catheter 120, or other catheters/sheaths of the delivery system 100. When the wire-framed, self-expanding device 204 is being withdrawn into a catheter, the exterior inner catheter 160o can be moved proximally until a distal end of the wire-framed, self-expanding device 204 abuts the catheter, causing inversion of the wire-framed, self-expanding device 204, and subsequent collapse of the wire-framed, self-expanding device 204 as the wire-framed, self-expanding device 204 is pulled into the confines of the catheter/sheath for removal.

Figure 45:
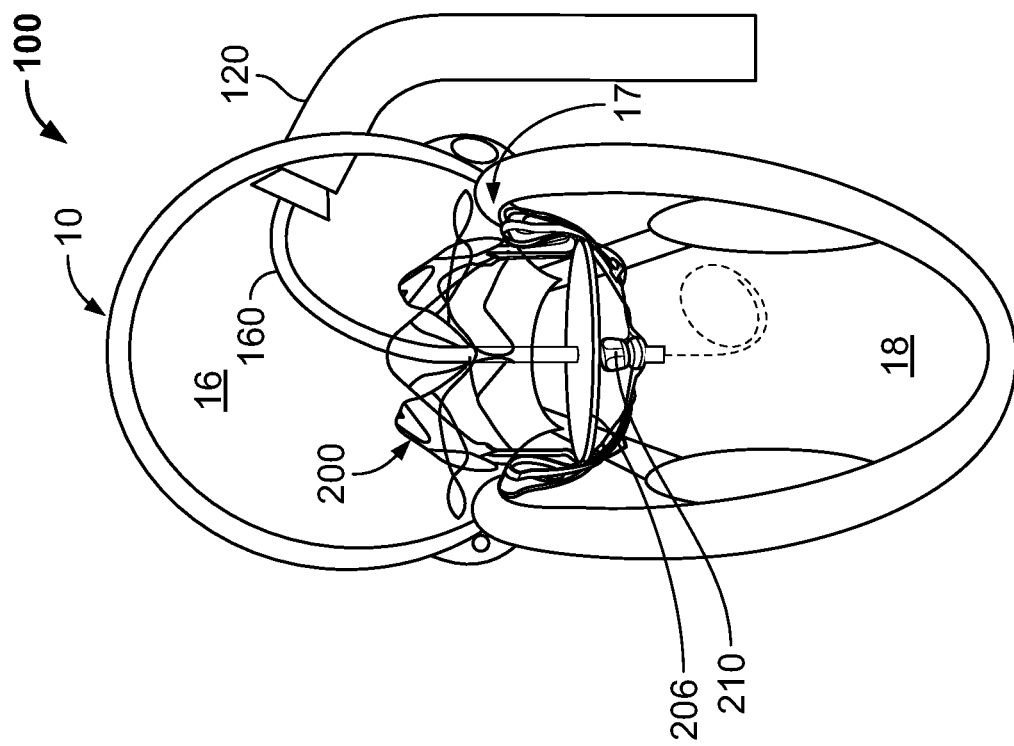
FIG. 45 shows the arrangement of FIG. 44 with the wire-framed, self-expanding device collapsed within the anchor assembly.
Figure 44:
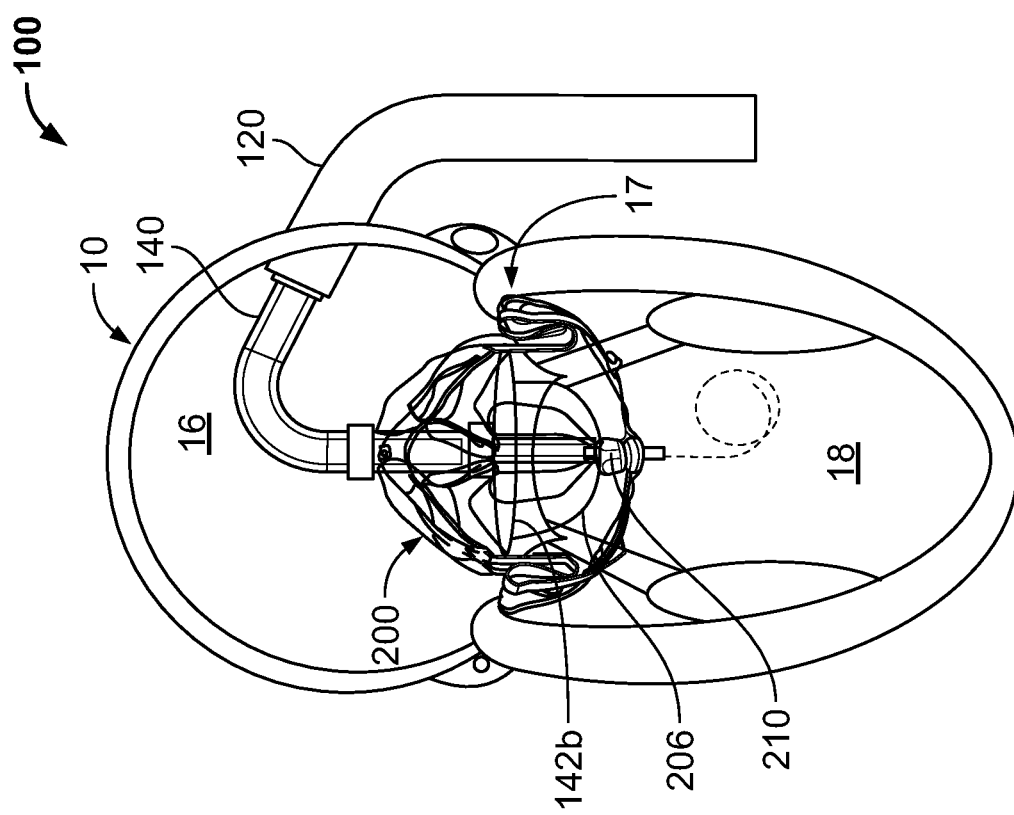
FIG. 44 shows a commissural cross-sectional view of a heart with the anchor assembly of FIG. 7 being deployed within the native mitral valve, with a wire-framed, self-expanding device expanded within the anchor assembly to provide a temporary spacer that enhances the sealing function provided by the native valve leaflets.

Referring to FIGS. 44 and 45, in some embodiments a wire-framed, self-expanding device 206 can be used to mitigate the potential for temporary MR after the implantation of the anchor assembly 200 (but prior to the implantation of a valve assembly as described further below). The wire-framed, self-expanding device 206 can occupy open space between the free edges of the native leaflets that may exist as a result of incomplete coaptation of the native valve leaflets after the anchor assembly 200 is implanted. The wire-framed, self-expanding device 206 can also act as a deflector, deflecting the central MR jet back into the left ventricle. The wire-framed, expandable device 206 is depicted in an unconstrained (expanded) configuration in FIG. 44, and depicted in a flattened (longitudinally contracted) configuration in FIG. 45.

FIGS. 44 and 45 correspond to FIGS. 9-11 described above, but with the addition of the wire-framed, self-expanding device 206. In the depicted embodiment, a distal end of the wire-framed, self-expanding device 206 is coupled to the outer diameter of the inner catheter 160 along a distal end portion of the inner catheter 160. Further, a proximal end portion of the wire-framed, self-expanding device 206 is releasably coupled to the anchor delivery catheter 140 via the mid-body control wire 142b.

One or more catheters (e.g., guide catheter 120) that are over the inner catheter 160, and/or the anchor delivery catheter 140, can be used to diametrically constrain the wire-framed, self-expanding device 206. When the constraining catheter is pulled proximally in relation to the inner catheter 160, the wire-framed, self-expanding device 206 will emerge and can self-expand to the configuration shown in FIG. 44. Other catheters of the delivery system 100 can nest inside the wire-framed, self-expanding device 206 when the wire-framed, self-expanding device 206 is in an expanded configuration.

In some embodiments, the wire-framed, self-expanding device 206 comprises a wire-framed construct with a flexible material covering the frame. For example, in some embodiments a nitinol wire framework is used to provide the structure and shape of the wire-framed, self-expanding device 206. The nitinol frame may be made, for example, by laser-cutting and expanding a nitinol tube (and then heat-setting the expanded tube in the desired, expanded shape). In some embodiments, one or more nitinol wires may be wound or woven to provide the desired, expanded shape.

In some embodiments, the expanded shape of the wire-framed, self-expanding device 206 is generally cylindrical. In some embodiments, the wire-framed, self-expanding device 206 (when expanded) is cylindrically-shaped with a diameter of about 25 mm to about 35 mm, or about 20 mm to about 30 mm, or about 30 mm to about 40 mm, without limitation. In some embodiments, the wire-framed, self-expanding device 206 can be configured to expand to a non-cylindrical shape such as, but not limited to, conical, spool-shaped, elliptically-shaped, spherical, shaped to approximate the natural line of coaptation between native mitral valve leaflets, and the like.

In some embodiments, the flexible covering material of the wire-framed, self-expanding device 206 is comprised of a urethane material with a thin wall such that the wire-framed, self-expanding device 206 is highly compliant. Other materials may also be used to make the wire-framed, self-expanding device 206 such as, but not limited to, latex, silicone, PET, ePTFE, PTFE, a polyester, ELAST-EON™ (a silicone and urethane polymer), another biocompatible polymer, DACRON®, copolymers, or combinations and subcombinations thereof.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the wire-framed, self-expanding device 206 is collapsed prior to deploying the valve assembly. To collapse the wire-framed, self-expanding device 206, the mid-body control wire 142b can be decoupled from the wire-framed, self-expanding device 206, causing the wire-framed, self-expanding device 206 to flatten towards the distal portion of the inner catheter 160, where the wire-framed, self-expanding device 206 is attached to the inner catheter 160 (as depicted in FIG. 45). By such flattening of the wire-framed, self-expanding device 206, valve assembly can be deployed with removing the wire-framed, self-expanding device 206 and without the wire-framed, self-expanding device 206 interfering with valve assembly deployment.

In some embodiments, the wire-framed, self-expanding device 206 can be withdrawn into anchor delivery catheter 140, guide catheter 120, or other catheters/sheaths of the delivery system 100. When the wire-framed, self-expanding device 206 is being withdrawn into a catheter, the inner catheter 160 can be moved proximally until a distal end of the wire-framed, self-expanding device 206 abuts the catheter, causing inversion of the wire-framed, self-expanding device 206, and subsequent diametrical collapse of the wire-framed, self-expanding device 206 as the wire-framed, self-expanding device 206 is drawn into the catheter/sheath for removal.

Figure 47:
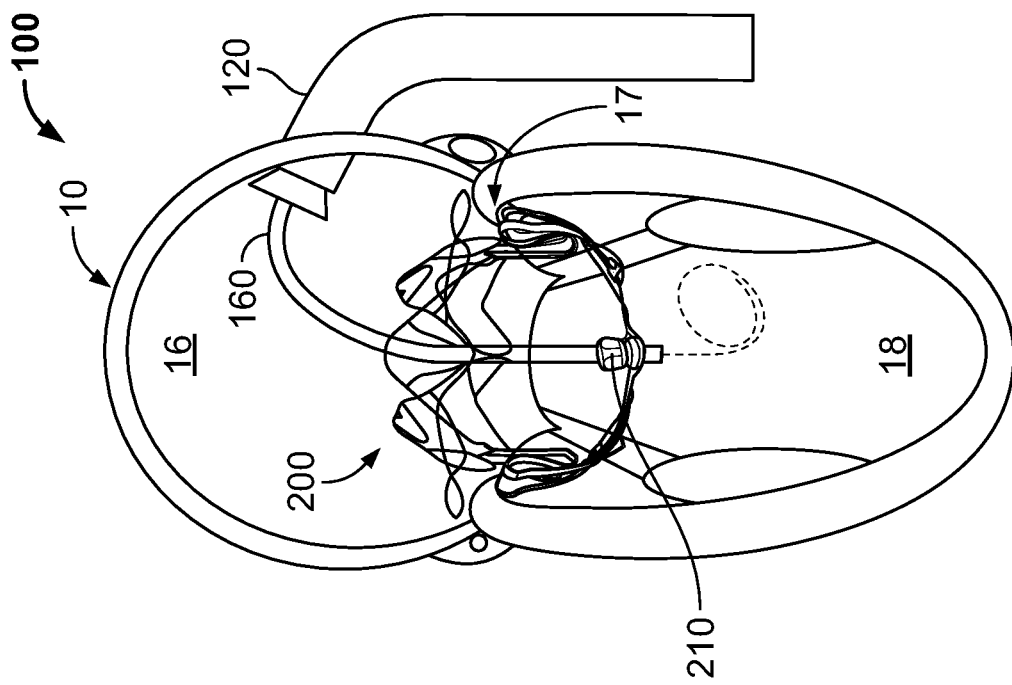
FIG. 47 shows the arrangement of FIG. 46 with the wire-framed, self-expanding device removed from the anchor assembly.
Figure 46:
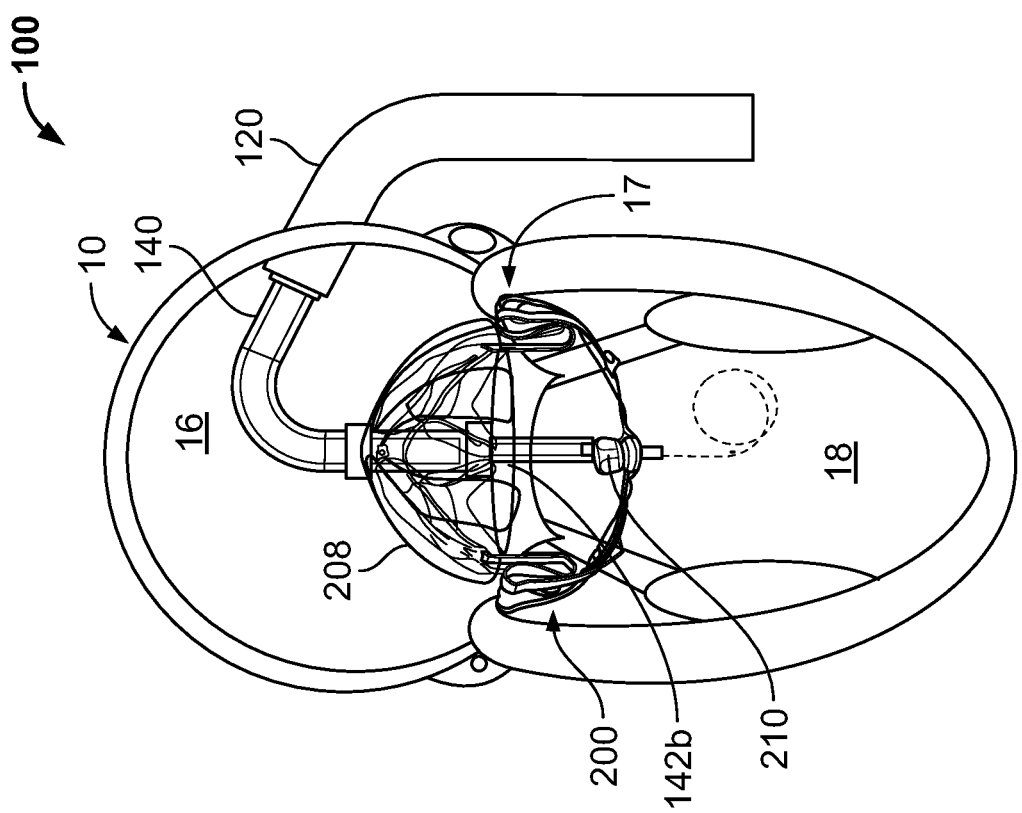
FIG. 46 shows a commissural cross-sectional view of a heart with the anchor assembly of FIG. 7 being deployed within the native mitral valve, with a wire-framed, self-expanding device expanded within the anchor assembly to provide a temporary spacer that enhances the sealing function provided by the native valve leaflets.

Referring to FIGS. 46 and 47, in some embodiments a wire-framed, self-expanding device 208 can be used to mitigate the potential for temporary MR after the implantation of the anchor assembly 200 (but prior to the implantation of a valve assembly as described further below). The wire-framed, self-expanding device 208 can occupy open space between the free edges of the native leaflets that may exist as a result of incomplete coaptation of the native valve leaflets after the anchor assembly 200 is implanted. The wire-framed, self-expanding device 208 can also act as a deflector, deflecting the central MR jet back into the left ventricle. The wire-framed, expandable device 208 is depicted in an unconstrained (expanded) configuration in FIG. 46, and removed from the anchor assembly 200 in FIG. 47.

FIGS. 46 and 47 correspond to FIGS. 9-11 described above, but with the addition of the wire-framed, self-expanding device 208. In the depicted embodiment, a proximal end portion of the wire-framed, self-expanding device 208 is coupled to a distal portion of the anchor delivery catheter 140. Further, a distal end portion of the wire-framed, self-expanding device 208 is releasably coupled to the anchor delivery catheter 140 via the mid-body control wire 142b.

One or more catheters (e.g., guide catheter 120) that are over the inner catheter 160, and/or the anchor delivery catheter 140, can be used to diametrically constrain the wire-framed, self-expanding device 208. When the constraining catheter is pulled proximally in relation to the inner catheter 160, the wire-framed, self-expanding device 208 will emerge and can self-expand to the configuration shown in FIG. 46.

In some embodiments, the wire-framed, self-expanding device 208 comprises a wire-framed construct with a flexible material covering the frame. For example, in some embodiments a nitinol wire framework is used to provide the structure and shape of the wire-framed, self-expanding device 208. The nitinol frame may be made, for example, by laser-cutting and expanding a nitinol tube (and then heat-setting the expanded tube in the desired, expanded shape). In some embodiments, one or more nitinol wires may be wound or woven to provide the desired, expanded shape.

In some embodiments, the expanded shape of the wire-framed, self-expanding device 208 is generally cylindrical. In some embodiments, the wire-framed, self-expanding device 208 (when expanded) is cylindrically-shaped with a diameter of about 25 mm to about 35 mm, or about 20 mm to about 30 mm, or about 30 mm to about 40 mm, without limitation. In some embodiments, the wire-framed, self-expanding device 208 can be configured to expand to a non-cylindrical shape such as, but not limited to, conical, spool-shaped, elliptically-shaped, spherical, shaped to approximate the natural line of coaptation between native mitral valve leaflets, and the like.

In some embodiments, the flexible covering material of the wire-framed, self-expanding device 208 is comprised of a urethane material with a thin wall such that the wire-framed, self-expanding device 208 is highly compliant. Other materials may also be used to make the wire-framed, self-expanding device 208 such as, but not limited to, latex, silicone, PET, ePTFE, PTFE, a polyester, ELAST-EON™ (a silicone and urethane polymer), another biocompatible polymer, DACRON®, copolymers, or combinations and sub-combinations thereof.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the wire-framed, self-expanding device 208 is collapsed and/or removed prior to deploying the valve assembly. To collapse the wire-framed, self-expanding device 208, the mid-body control wire 142b can be decoupled from the wire-framed, self-expanding device 208, allowing the wire-framed, self-expanding device 208 to be diametrically compressed. In some embodiments, the wire-framed, self-expanding device 208 can be withdrawn into the guide catheter 120, or other catheters/sheaths of the delivery system 100, via the anchor delivery catheter 140. When the wire-framed, self-expanding device 208 is being withdrawn into a catheter, the anchor delivery catheter 140 can be moved proximally until a proximal end of the wire-framed, self-expanding device 208 abuts the catheter, causing the wire-framed, self-expanding device 208 to diametrically collapse as the wire-framed, self-expanding device 208 is drawn into the catheter/sheath for removal.

Figure 49:
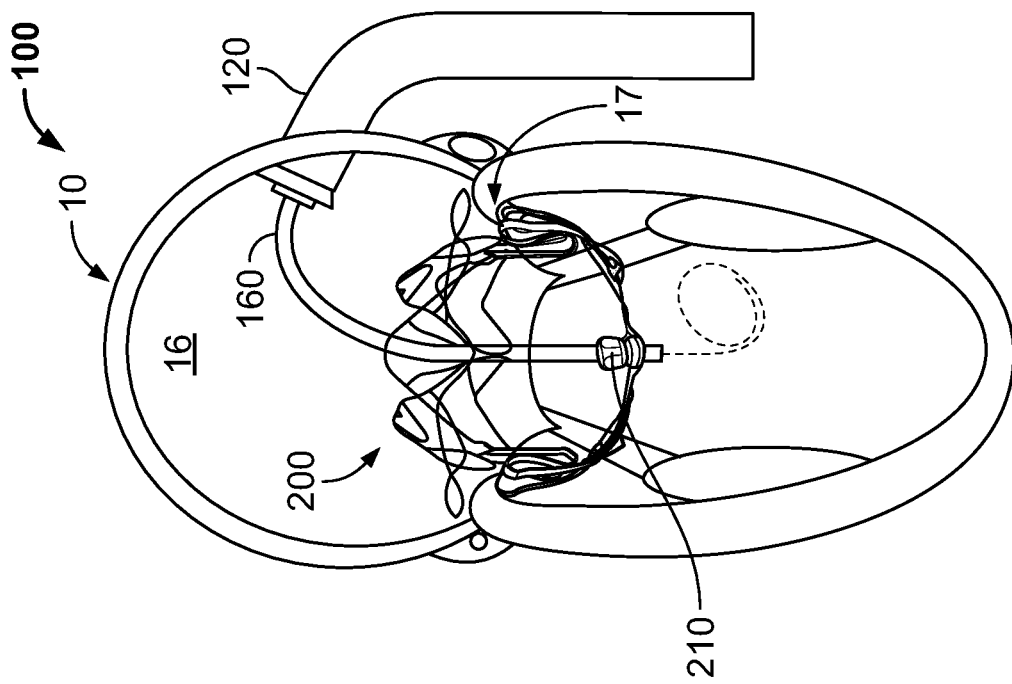
FIG. 49 shows the arrangement of FIG. 48 with the wire-framed, self-expanding device removed from the anchor assembly.
Figure 48:
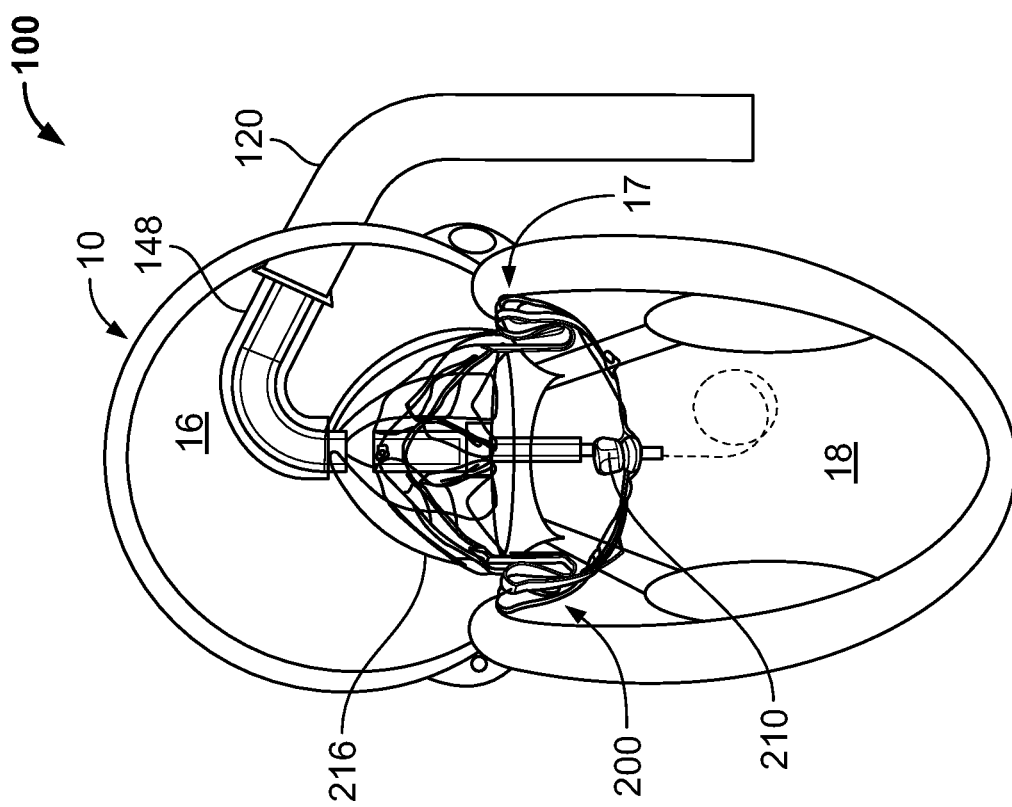
FIG. 48 shows a commissural cross-sectional view of a heart with the anchor assembly of FIG. 7 being deployed within the native mitral valve, with a wire-framed, self-expanding device expanded within the anchor assembly to provide a temporary spacer that enhances the sealing function provided by the native valve leaflets.
Figure 50:
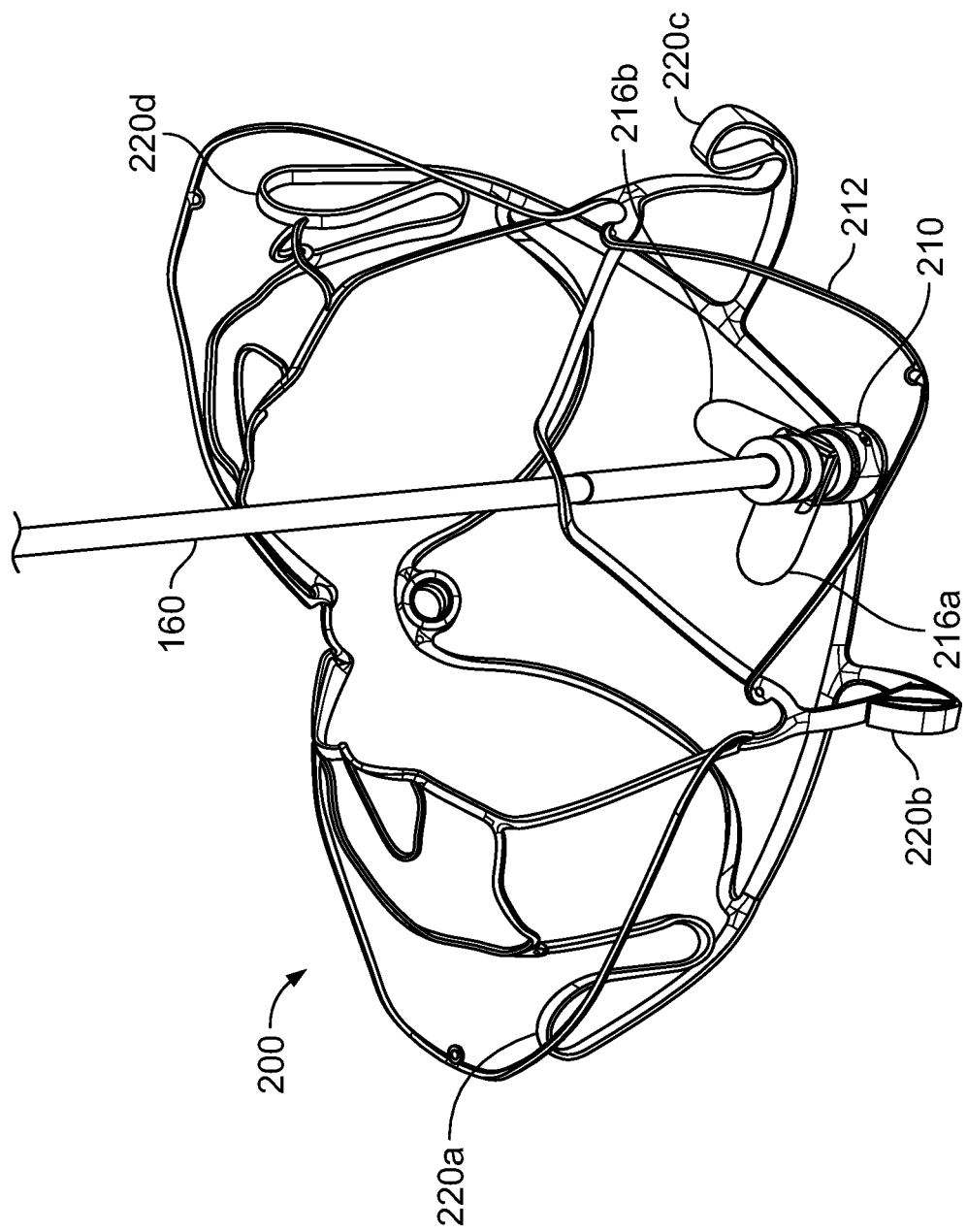
FIG. 50 shows an inflatable device positioned within the anchor assembly of FIG. 7, such that the inflatable device, when inflated, can provide a temporary spacer that enhances the sealing function provided by the native valve leaflets.

Referring to FIGS. 48 and 49, in some embodiments a wire-framed, self-expanding device 216 can be used to mitigate the potential for temporary MR after the implantation of the anchor assembly 200 (but prior to the implantation of a valve assembly as described further below). The wire-framed, self-expanding device 216 can occupy open space between the free edges of the native leaflets that may exist as a result of incomplete coaptation of the native valve leaflets after the anchor assembly 200 is implanted. The wire-framed, self-expanding device 216 can also act as a deflector, deflecting the central MR jet back into the left ventricle. The wire-framed, expandable device 216 is depicted in an unconstrained (expanded) configuration in FIG. 48, and removed from the anchor assembly 200 in FIG. 49.

FIGS. 48 and 49 correspond to FIGS. 9-11 described above, but with the addition of the wire-framed, self-expanding device 216. In the depicted embodiment, a proximal end portion of the wire-framed, self-expanding device 216 is coupled to a distal portion of a deflector catheter 148. In this embodiment, the wire-framed, self-expanding device 216 can be selectively deployed by advancing the deflector catheter 148 over the anchor delivery catheter 140. Alternatively, the wire-framed, self-expanding device 216 may be releasably coupled to the anchor delivery catheter 140 along a distal portion of the anchor delivery catheter 140 at a distal end of the wire-framed, self-expanding device 216 via the mid-body control wire 142b. In this embodiment, the anchor delivery catheter 140 and the deflector catheter 148 can be deployed together, with the deflector catheter 148 being able to be removed without removal of the anchor delivery catheter 140, once the wire-framed, self-expanding device 216 is released from the mid-body control wire 142b.

One or more catheters (e.g., guide catheter 120) that are over the deflector catheter 148 can be used to diametrically constrain the wire-framed, self-expanding device 216. When the constraining catheter is pulled proximally in relation to the deflector catheter 148, or alternatively, when the deflector catheter 148 is moved distally past the constraining catheter, the wire-framed, self-expanding device 216 will emerge and can self-expand to the configuration shown in FIG. 48.

In some embodiments, the wire-framed, self-expanding device 216 comprises a wire-framed construct with a flexible material covering the frame. For example, in some embodiments a nitinol wire framework is used to provide the structure and shape of the wire-framed, self-expanding device 216. The nitinol frame may be made, for example, by laser-cutting and expanding a nitinol tube (and then heat-setting the expanded tube in the desired, expanded shape). In some embodiments, one or more nitinol wires may be wound or woven to provide the desired, expanded shape.

In some embodiments, the expanded shape of the wire-framed, self-expanding device 216 is generally cylindrical. In some embodiments, the wire-framed, self-expanding device 216 (when expanded) is cylindrically-shaped with a diameter of about 25 mm to about 35 mm, or about 20 mm to about 30 mm, or about 30 mm to about 40 mm, without limitation. In some embodiments, the wire-framed, self-expanding device 216 can be configured to expand to a non-cylindrical shape such as, but not limited to, conical, spool-shaped, elliptically-shaped, spherical, shaped to approximate the natural line of coaptation between native mitral valve leaflets, and the like.

In some embodiments, the flexible covering material of the wire-framed, self-expanding device 216 is comprised of a urethane material with a thin wall such that the wire-framed, self-expanding device 216 is highly compliant. Other materials may also be used to make the wire-framed, self-expanding device 216 such as, but not limited to, latex, silicone, PET, ePTFE, PTFE, a polyester, ELAST-EON™ (a silicone and urethane polymer), another biocompatible polymer, DACRON®, copolymers, or combinations and sub-combinations thereof.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the wire-framed, self-expanding device 216 is removed prior to deploying the valve assembly. In some embodiments, the wire-framed, self-expanding device 216 is collapsed prior to removal, to collapse the wire-framed, self-expanding device 216, the mid-body control wire 142b can be decoupled from the wire-framed, self-expanding device 216, allowing the wire-framed, self-expanding device 216 to be diametrically compressed. In some embodiments, the wire-framed, self-expanding device 216 can be withdrawn into the guide catheter 120, or other catheters of the delivery system 100, via the deflector catheter 148. When the wire-framed, self-expanding device 216 is being withdrawn into a catheter, the deflector catheter 148 can be moved proximally until a proximal end of the wire-framed, self-expanding device 216 abuts the catheter, causing the wire-framed, self-expanding device 216 to diametrically collapse as the wire-framed, self-expanding device 216 is drawn into the catheter/sheath for removal.

Referring to FIGS. 50 through 58, in some embodiments one or more balloons, for example a first balloon 216a and a second balloon 216b, can be used to mitigate the potential for temporary MR after the implantation of the anchor assembly 200 (but prior to the implantation of a valve assembly as described further below). The first and second balloons 216a and 216b can occupy open space between the free edges of the native leaflets that may exist as a result of incomplete coaptation of the native valve leaflets after the anchor assembly 200 is implanted. The first and second balloons 216a and 216b can also act as deflectors, deflecting the central MR jet back into the left ventricle. The first and second balloons 216a and 216b are depicted in an inflated (expanded) configuration in FIGS. 53 and 54, and are depicted in a deflated (contracted) configuration in FIGS. 50-52 and 56-58.

Figure 51:
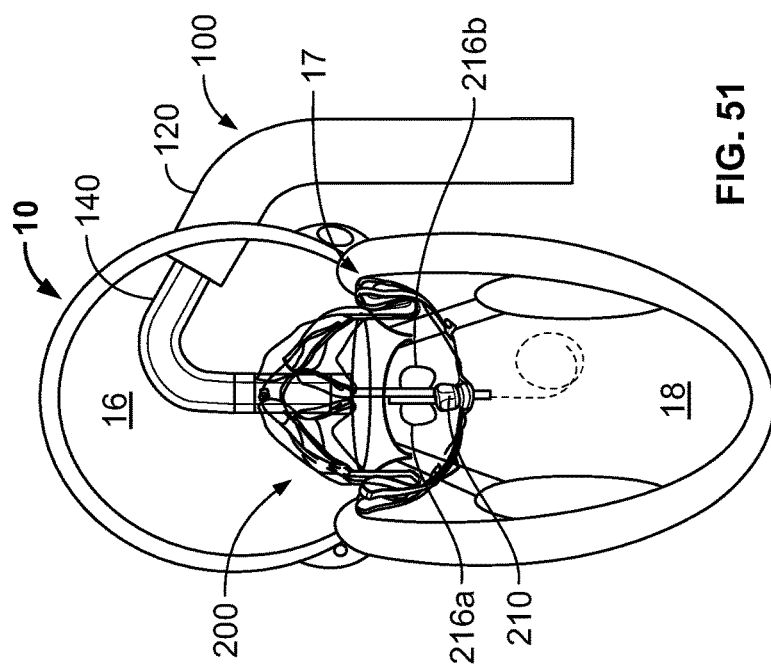
FIG. 51 shows a commissural cross-sectional view of a heart with the anchor assembly of FIG. 7 being deployed within the native mitral valve, with the inflatable device of FIG. 50 within the anchor assembly, such that the inflatable device, when inflated, can provide a temporary spacer that enhances the sealing function provided by the native valve leaflets.
Figure 52:
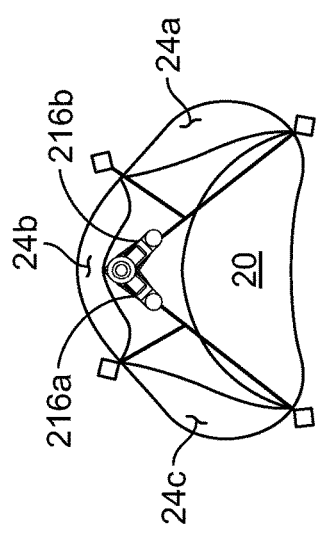
FIG. 52 shows a bottom view of the inflatable device of FIG. 50 within the anchor assembly of FIG. 7, when the anchor assembly is deployed within the native mitral valve.
Figure 53:
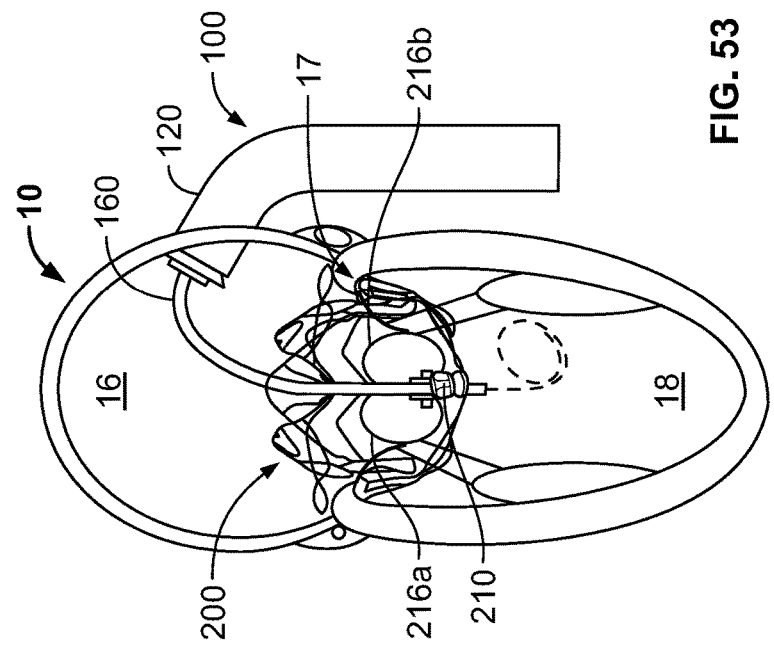
FIG. 53 shows a commissural cross-sectional view of a heart with the anchor assembly of FIG. 7 being deployed within the native mitral valve, with the inflatable device of FIG. 50 within the anchor assembly, with the inflatable device inflated to provide a temporary spacer that enhances the sealing function provided by the native valve leaflets.
Figure 54:
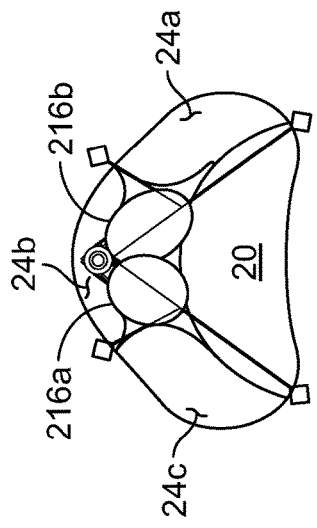
FIG. 54 shows a bottom view of the inflatable device of FIG. 50 within the anchor assembly of FIG. 7, when the anchor assembly is deployed within the native mitral valve and the inflatable device is inflated to provide a temporary spacer that enhances the sealing function provided by the native valve leaflets.

FIGS. 51 and 53 correspond to FIGS. 9-11 described above, but with the addition of the first and second balloons 216a and 216b. In the depicted embodiment, as shown in FIGS. 50 and 56-58 the first and second balloons 216a and 216b are coupled to the inner catheter 160 and are in fluid communication with a manifold 219 having two nozzles. The manifold 219 can be coupled to a distal portion of the inner catheter 160, proximal to threaded distal tip portion 162, covering an inflation port 163. In that arrangement, the manifold 219 (and the balloons 216a-b via the nozzles) can be in fluid communication, via the inflation port 163, with a lumen defined by the inner catheter 160. The threaded distal tip portion 162 can secure to the hub 210 of the anchor assembly 200.

In some embodiments, the manifold 219 can be secured in place onto inner catheter 160 by a proximal threaded collar 218a and a distal threaded collar 218b, secured to the threaded distal tip portion of the inner catheter 160. In some embodiments, the first and second balloons 216a and 216b can extend laterally or radially from the manifold 219 (along the axes of the nozzles) and wrap back toward the inner catheter 160 to be secured between the manifold 219 and the distal threaded collar 218b. In some embodiments, the proximal threaded collar 218a and the distal threaded collar 218b can include O-rings, or other sealing components to aid in securing and sealing the first balloon 216a and the second balloon 216b to the manifold 219 and the inner catheter 160. The manifold 219 can include the nozzles defining respective lumens extending from the inner catheter 160 to allow inflation of the first and second balloons 216a and 216b.

In the depicted embodiment, the nozzles of the manifold 219 can be respectively oriented such that the axes of the first balloon 216a and the second balloon 216b are orientated non-linear one another. For example, the axis of the first balloon 216a relative to the axis of the second balloon 216b may be respectively oriented about 80 degrees to about 100 degrees, or about 70 degrees to about 90 degrees, or about 90 degrees to about 110 degrees, without limitation. In some embodiments, the first balloon 216a and the second balloon 216b (when expanded) can have a combined total, overall width of about 25 mm to about 35 mm, or about 20 mm to about 30 mm, or about 30 mm to about 40 mm, without limitation. Due to the configuration of the first balloon 216a and the second balloon 216b in relation to the manifold 219, the first balloon 216a and the second balloon 216b can expand radially/laterally from the inner catheter 160 and axially along the inner catheter 160. In some embodiments, the first balloon 216a and the second balloon 216b can be made of a material (e.g., an elastic, a thermal plastic, silicone, etc.) that can be expand up to ten times its original size, such that the profile of the first balloon 216a and the second balloon 216b can be small during insertion and deployment of the inner catheter 160, but can greatly expand to reduce temporary MR.

When the potential for temporary MR is present after the implantation of the anchor assembly 200, the first balloon 216a and the second balloon 216b can be inflated. To inflate the first balloon 216a and the second balloon 216b, a fluid (e.g., saline, $CO_2$, and the like) can be injected into one or more inflation ports 164 located at a proximal end of the inner catheter 160 (e.g., via a syringe). Once the first balloon 216a and the second balloon 216b are inflated, a sliding member 161 can be slid distally to close the inflation port(s) 164. In the depicted embodiment, the sliding member 161 can include pliable ends (e.g., a soft polymer), such that the inflation port(s) 164 can be sealed while the first balloon 216a and the second balloon 216b remain inflated, such that the inflation device (e.g., the syringe) can be removed, and other catheters can be slid over the inner catheter 160, without interfering with the inflated state of the first balloon 216a and the second balloon 216b if so desired.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the first balloon 216a and the second balloon 216b can remain inflated when deploying the valve assembly. Since the first balloon 216a and the second balloon 216b are located on a distal portion of the inner catheter 160, the first balloon 216a and the second balloon 216b, when inflated or deflated, do not interfere with deployment of the valve assembly.

Figure 59:
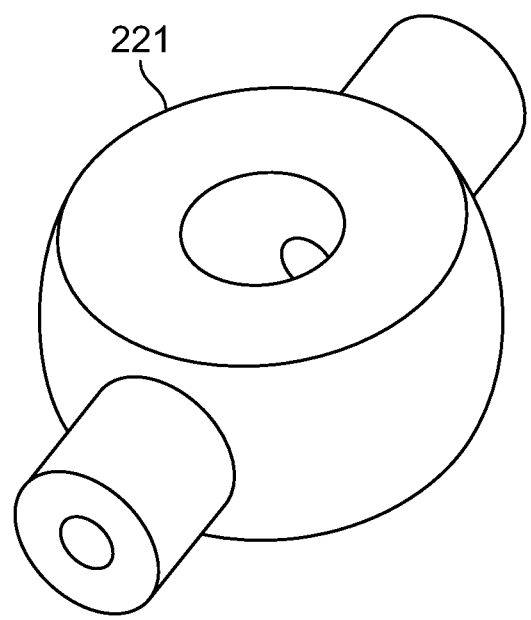
FIG. 59 shows a perspective view of a manifold for an inflatable device, for providing a temporary spacer that can enhance the sealing function provided by the native valve leaflets.
Figure 60:
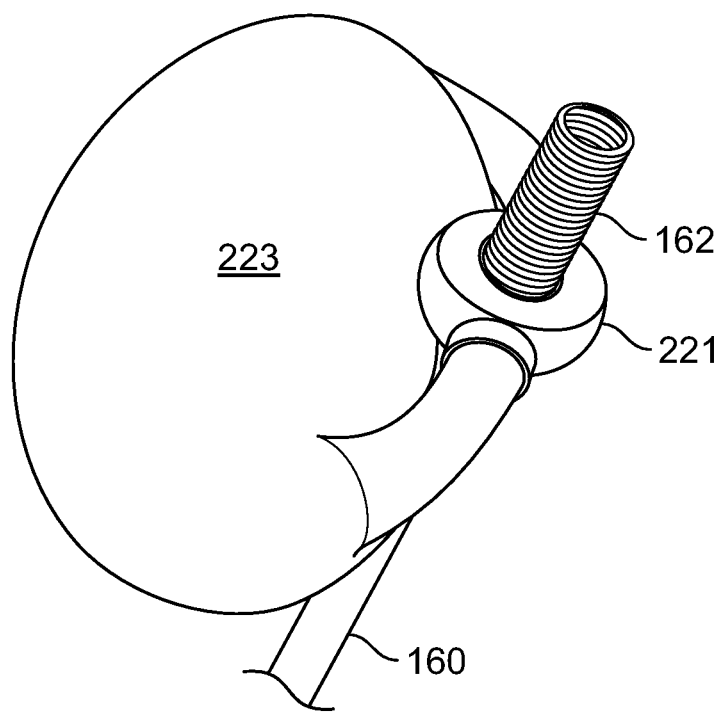
FIG. 60 shows a perspective view of an inflatable device with the manifold of FIG. 59 coupled to an inner catheter for providing a temporary spacer that can enhance the sealing function provided by the native valve leaflets.

Referring to FIGS. 59 and 60, in some embodiments a balloon 223 can be used to mitigate the potential for temporary MR after the implantation of the anchor assembly 200 (but prior to the implantation of a valve assembly as described further below). The balloon 223 can occupy open space between the free edges of the native leaflets that may exist as a result of incomplete coaptation of the native valve leaflets after the anchor assembly 200 is implanted. The balloon 223 can also act as a deflector, deflecting the central MR jet back into the left ventricle. The balloon 223 is depicted in an inflated (expanded) configuration in FIG. 60. In some embodiments, the balloon 223 is non-spherical when expanded.

In the depicted embodiment, as shown in FIG. 60, the balloon 223 can be coupled to the inner catheter 160 via a manifold 221. The manifold 221 can be coupled to a distal portion of the inner catheter 160, proximal to threaded distal tip portion 162, covering an inflation port (e.g., inflation port 163 of FIG. 55). The threaded distal tip portion 162 can secure the inner catheter 160 to the hub 210 of the anchor assembly 200. In some embodiments, the manifold 221 can be secured in place onto the threaded distal tip portion of the inner catheter 160 by a proximal threaded collar and a distal threaded collar, similar to the arrangement shown in FIGS. 56-58. In the depicted embodiment, the balloon 223 can extend from a first nozzle of the manifold 221 and wrap to a second nozzle of the manifold 221. The manifold 221 can include lumens extending through the nozzle from the inflation port(s) 164 on inner catheter 160 to allow inflation of the balloon 223, via a lumen defined by the inner catheter 160.

In the depicted embodiment, the manifold 221 can be shaped such that the first and second nozzles, and therefore two ends of the balloon 223 can be located opposite one another. In some embodiments, the balloon 223 (when expanded) can have a total width of about 25 mm to about 35 mm, or about 20 mm to about 30 mm, or about 30 mm to about 40 mm, without limitation. Due to the configuration of the balloon 223 in relation to the manifold 221, the balloon 223 can expand radially/laterally from the inner catheter 160 and axially along the inner catheter 160. In some embodiments, the balloon 223 can be made of a material (e.g., an elastic, a thermal plastic, silicone, etc.) that can be expand up to ten times the original size, such that the profile of the balloon 223 can be small during insertion and deployment of the inner catheter 160, but can greatly expand when inflated to reduce temporary MR.

When the potential for temporary MR is present after the implantation of the anchor assembly 200, the balloon 223 can be inflated. To inflate the balloon 223, a fluid (e.g., saline, CO2, and the like) can be injected into one or more inflation ports 164 (FIG. 55) located at a proximal end of the inner catheter 160 (e.g., via a syringe). Once the balloon 223 is inflated, a sliding member 161 can be slide distally to close the inflation port(s) 164. In some embodiments, similar to FIG. 55, the sliding member 161 can include pliable ends (e.g., a soft polymer), such that the inflation port(s) 164 can be sealed while the balloon 223 remain inflated, such that the inflation device (e.g., the syringe) can be removed, and other catheters can be slid over the inner catheter 160, without interfering with the inflation of the balloon 223.

After the implantation of the anchor assembly 200 within the native mitral valve 17 (as performed, for example, in accordance with FIGS. 1-5, 7-11, 35 and 36), a valve delivery catheter 180 of the delivery system 100 can be used to deploy a valve assembly within the anchor assembly 200 (as described further below). In some embodiments, the balloon 223 can remain inflated when deploying the valve assembly. Since the balloon 223 is located on a distal portion of the inner catheter 160, the balloon 223, when inflated or deflated, does not interfere with deployment of the valve assembly.

Figure 61:
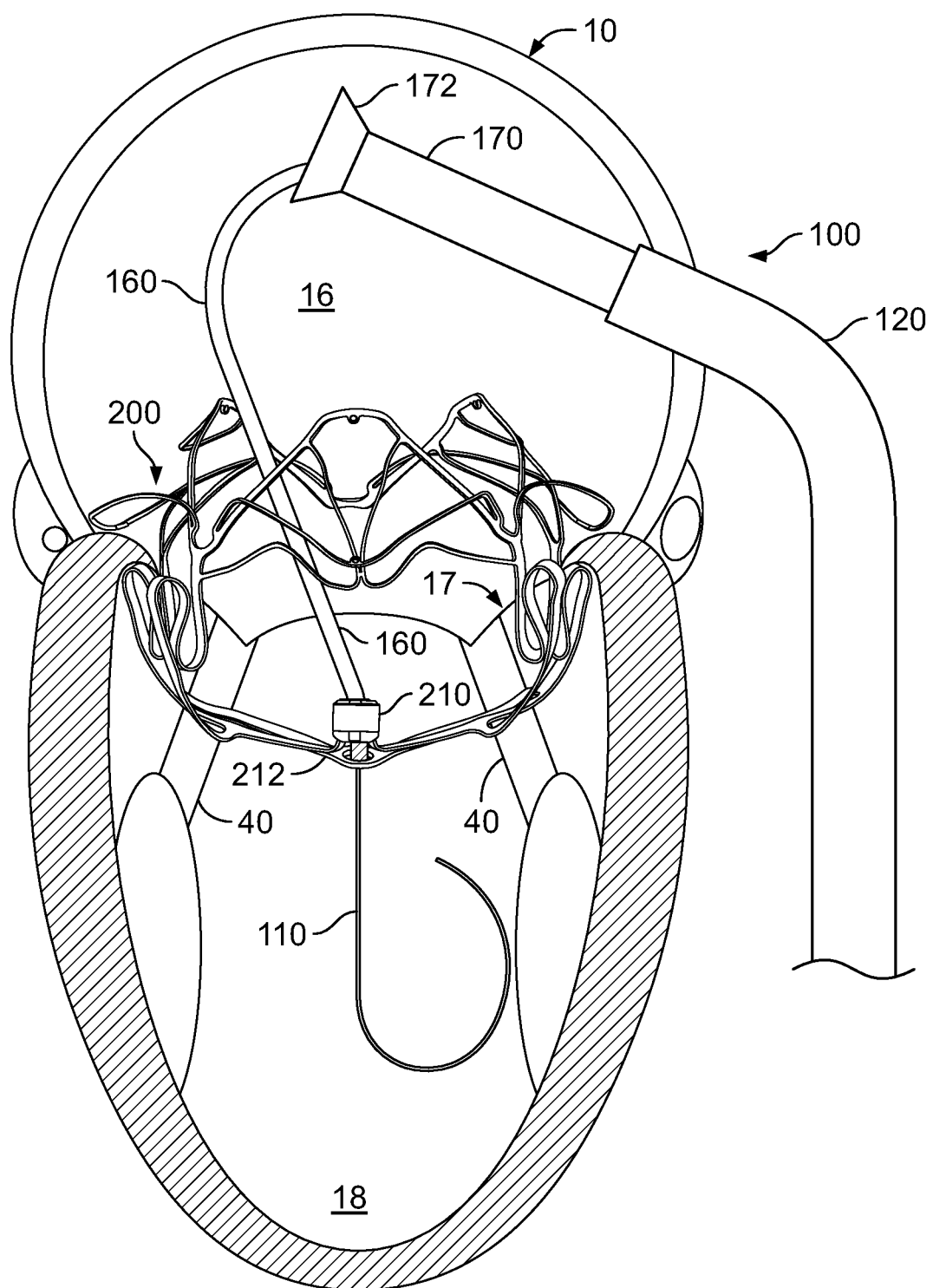
FIG. 61 shows a perspective view of the anchor assembly of FIG. 7 implanted within the native mitral valve and a valve assembly delivery sheath extending into the left atrium (in a commissural cross-sectional view of the heart).

Referring to FIG. 61, after implantation of the anchor assembly 200 within the native mitral valve 17 (as performed, for example, in accordance with FIGS. 1-5, 7-11, 24, 27, 28, and 33-38 described above), a valve delivery sheath 170 of the delivery system 100 can be used to deploy a valve assembly within the anchor assembly 200. As described above in reference to FIG. 11, with the inner catheter 160 coupled with the hub 210 of the anchor assembly 200, the inner catheter 160 can be used to guide the valve assembly into the interior of the anchor assembly 200.

In the depicted embodiment, the SAM containment member 212 is constrained in its pre-deployed configuration. However, in some other SAM containment member embodiments, the SAM containment member may be deployed prior to installation of a valve assembly within the anchor assembly 200. Generally speaking, depending on the SAM containment member embodiment's design, if the SAM containment member may potentially interfere with the function of the anterior leaflet, it may be preferable to wait until the valve is implanted to deploy the SAM containment member. But, if the SAM containment member does not or is unlikely to interfere with the leaflet function, the SAM containment member may be deployed prior to valve implant (which may be beneficial for situations where the anchor is implanted in a separate procedure from the valve implantation).

In some implementations, with the guide catheter 120 positioned with its distal end in the left atrium 16, the valve delivery sheath 170 is installed into a lumen of the guide catheter 120 (over the inner catheter 160) and advanced through the guide catheter 120. As described further below, in some embodiments the valve delivery sheath 170 is loaded at that time with a prosthetic valve assembly and other components of the delivery system 100. The guide catheter 120 may be the same catheter that was used to deliver the anchor assembly 200, or it may be a different catheter (but still referred to here as the guide catheter 120 for simplicity sake). Depending on the time interval between implantation of the anchor assembly 200 and the valve assembly 300, it may also be desirable to leave the same guide catheter 120 in situ during the time between the deliveries of each assembly.

In some embodiments, the valve delivery sheath 170 can be made from the materials described above in reference to the guide catheter 120. In some embodiments, the valve delivery sheath 170 has an outer diameter in the range of about 20 Fr to about 28 Fr (about 6.7 mm to about 9.3 mm). In some embodiments, the valve delivery sheath 170 has an outer diameter in the range of about 14 Fr to about 24 Fr (about 4.7 mm to about 8.0 mm).

In the depicted embodiment, the valve delivery sheath 170 includes a flared distal end portion 172. In some embodiments, no such flared distal end portion 172 is included. The flared distal end portion 172 can collapse to a lower profile when constrained within the guide catheter 120. When the flared distal end portion 172 is expressed from the guide catheter 120, the flared distal end portion 172 can self-expand to the flared shape. In some embodiments, the material of the flared distal end portion 172 includes pleats or folds, may be a continuous flared end or may be separated into sections such as flower pedals, and may include one or more resilient elements that bias the flared distal end portion 172 to assume the flared configuration in the absence of restraining forces (such as from containment within the guide catheter 120). The flared distal end portion 172 can be advantageous, for example, for recapturing the valve assembly (if desired) within the lumen of the valve delivery sheath 170 after the valve assembly has been expressed from the flared distal end portion 172.

In some embodiments, the maximum outer diameter of the flared distal end portion 172 is in a range of about 30 Fr to about 34 Fr (about 10.0 mm to about 11.3 mm). In some embodiments, the maximum outer diameter of the flared distal end portion 172 is in a range of about 32 Fr to about 44 Fr (about 10.7 mm to about 14.7 mm). In some embodiments, the maximum outer diameter of the flared distal end portion 172 is in a range of about 24 Fr to about 30 Fr (about 8.0 mm to about 10.0 mm). In some embodiments, the maximum outer diameter of the flared distal end portion 172 is less than about 24 Fr (about 8.0 mm) or greater than about 44 Fr (about 14.7 mm).

Figure 62:
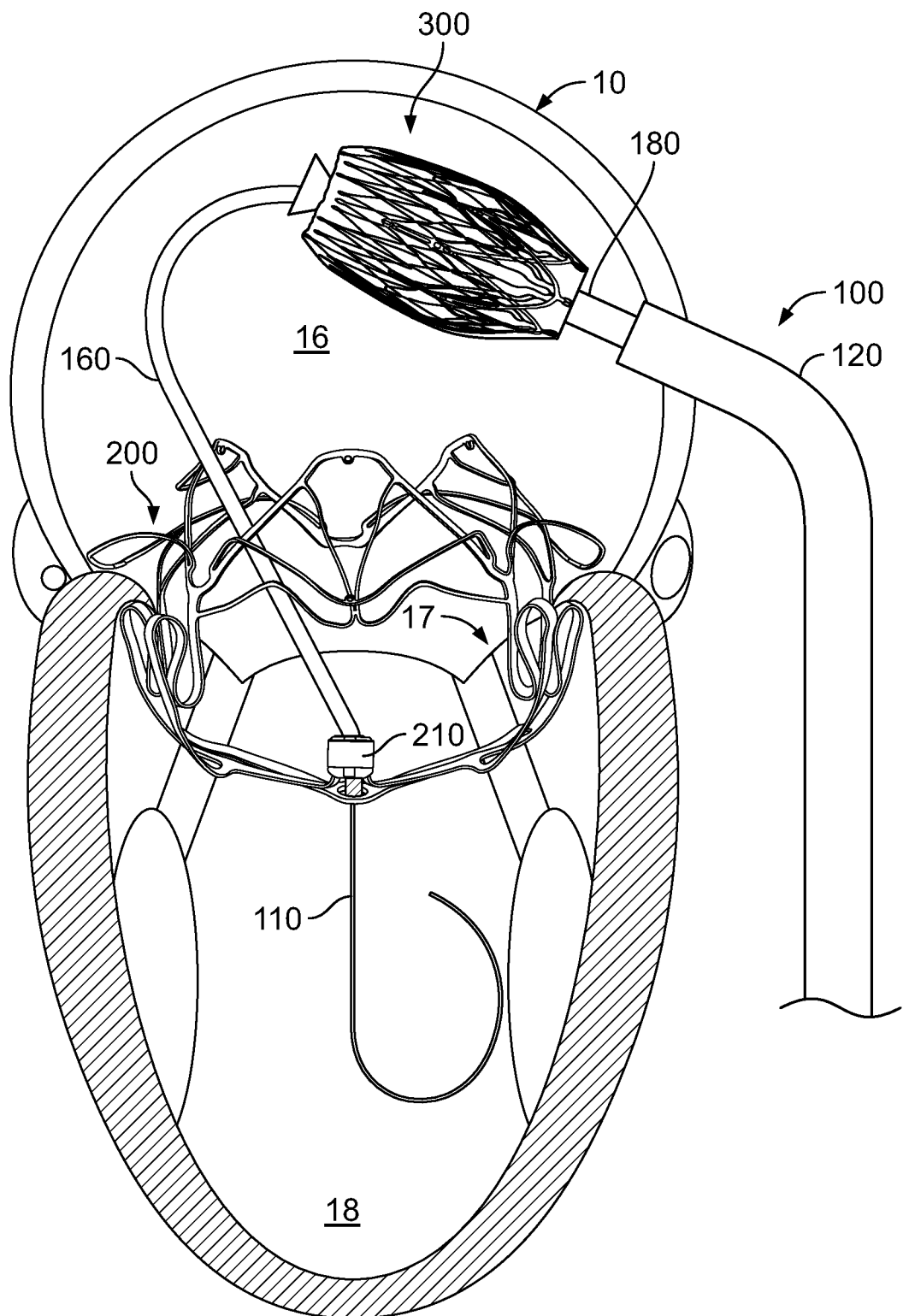
FIG. 62 shows a perspective view of a valve assembly in the left atrium after partial emergence from the valve assembly delivery sheath of FIG. 61. The valve assembly is configured in a first (partially expanded) arrangement.

Referring also to FIG. 62, in some implementations the valve delivery sheath 170 can be withdrawn into the guide catheter 120 while a valve delivery catheter 180 is held substantially stationary to thereby express a valve assembly 300 from a lumen of the valve delivery sheath 170. The valve delivery sheath 170 and the valve delivery catheter 180 are additional components in some embodiments of the example delivery system 100. It should be understood that movements of the components (e.g., the valve delivery sheath 170 and the valve delivery catheter 180) of the delivery system 100, whether the movements be those of individual components or two or more components in combination with each other, can in some embodiments be initiated and controlled using a deployment frame system (such as the example deployment frame system of FIG. 43 described below).

Figure 6:
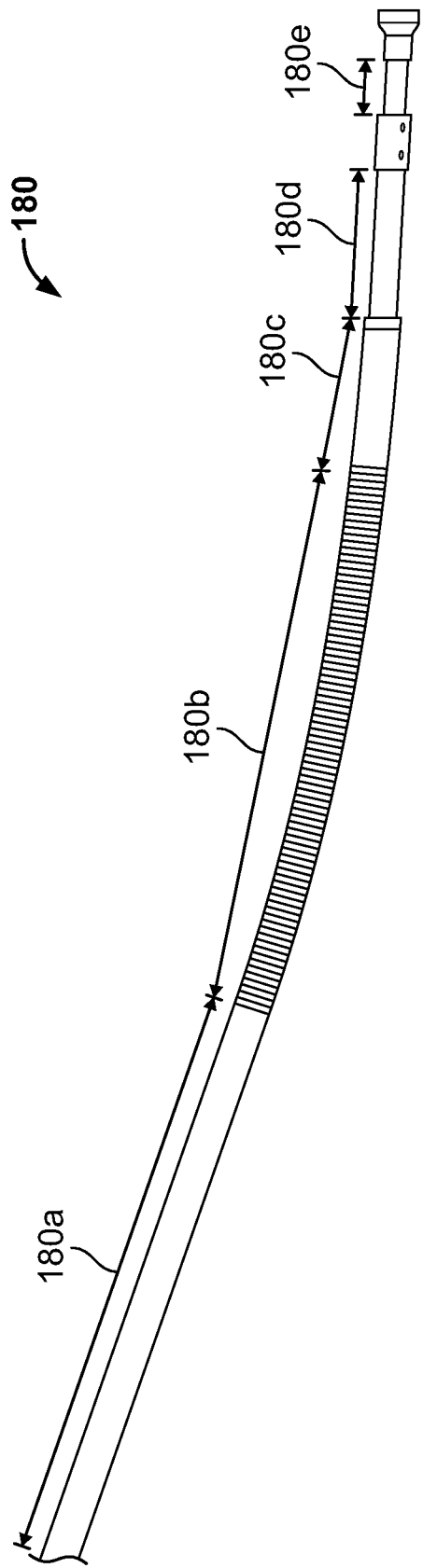
FIG. 6 shows a side view of a delivery catheter of prosthetic mitral valve deployment system.

Referring also to FIG. 6, in some embodiments the valve delivery catheter 180 can be advantageously configured with multiple zones that have differing mechanical properties such as flexibility, durometer, column strength, crush strength, elasticity, torqueability, trackability, and the like. For example, in the depicted embodiment the valve delivery catheter 180 includes a first zone 180a, a second zone 180b, a third zone 180c, a fourth zone 180d, and a fifth zone 180e. In one example, the first zone 180a has a durometer of about 72D, the second zone 180b has a durometer of about 35D, the third zone 180c has a durometer of about 25D, the fourth zone 180d has a durometer of about 55D, and the fifth zone 180e has a durometer of about 35D. The different zones may be constructed differently in relation to each other (e.g., using different polymers, coatings, coil reinforcements, braided reinforcements, hypotubes, etc.). Such variations in the mechanical properties (e.g., flexibility, etc.) of the valve delivery catheter 180 can be advantageous for the navigation of the valve delivery catheter 180 through the curvatures of a patient's vasculature. For example, in the depicted embodiment, the first zone 180a being 72D (for example) provides column strength for the section of the valve delivery catheter 180 that is expected to be in the inferior vena cava and/or right atrium. The zones 180b, 180c, 180d and 180e having example durometers of 35D, 25D, 55D and 35D respectively provide the flexibility for the valve delivery catheter 180 to navigate the curvature from right atrium to mitral annulus plane through fossa ovalis and left atrium. The zone 180d of 55D (for example) also provides the stiffness profile to align the axis of the valve delivery catheter 180 along the normal to the native mitral annulus plane. It should be understood that this is merely one example and other arrangements are also envisioned within the scope of this disclosure. Moreover, one or more other catheter devices of delivery system 100 can be configured with such multiple zones that have differing mechanical properties (as exemplified here in regard to valve delivery catheter 180).

Still referring to FIG. 62, the valve assembly 300 can be releasably coupled to the valve delivery catheter 180 and retained in a low-profile configuration. In some embodiments, both the distal and proximal ends of the valve assembly 300 are releasably coupled to the valve delivery catheter 180. In some embodiments, just one of the distal end or the proximal end of the valve assembly 300 is releasably coupled to the valve delivery catheter 180. In particular embodiments, one or more control wires may be included to releasably couple one or more portions of the valve assembly 300 to the valve delivery catheter 180. In some such embodiments, the one or more control wires may act as lassos to radially constrain the bias of the valve assembly 300 from radially self-expanding. Hence, a release of tension on the one or more control wires may allow at least a portion of the valve assembly 300 to radially self-expand.

Figure 63:
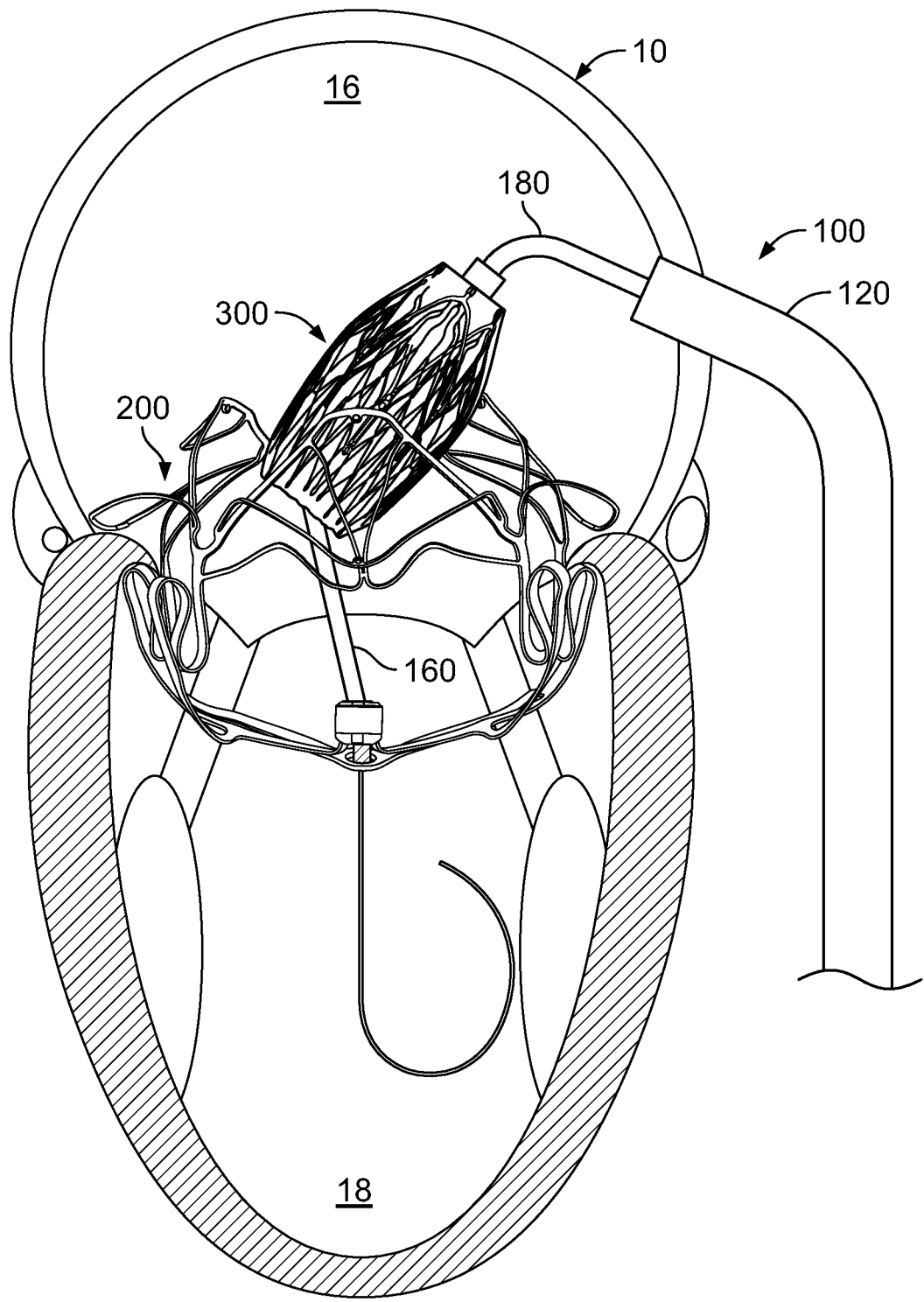
FIG. 63 shows a perspective view of the valve assembly of FIG. 62 with the valve deployment system being manipulated in preparation for the installation of the valve assembly into the anchor assembly.
Figure 64:
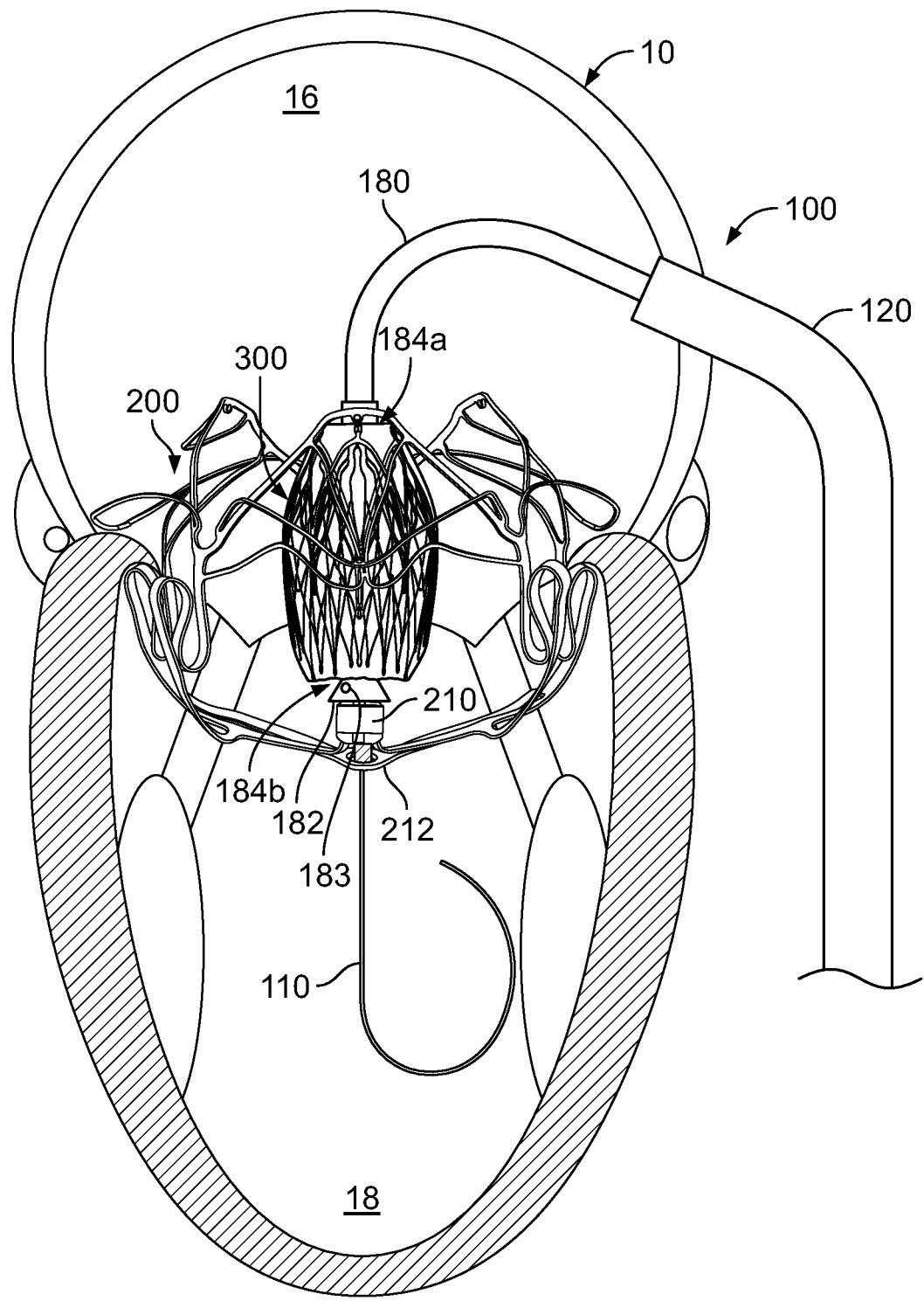
FIG. 64 shows a perspective view of the valve assembly of FIG. 62 (while still in the first, partially expanded arrangement) being positioned within the anchor assembly.

Referring to FIGS. 63 and 64, the delivery system 100 can be manipulated by a clinician operator to perform a lateral pivot (panning, rotation, etc.) of the valve assembly 300 within the left atrium 16. The rotation of the valve assembly 300 changes the alignment of the valve assembly 300 from being generally axial with the distal end portion of the guide catheter 120 to being generally axial with the anchor assembly 200 (in preparation for installation of the valve assembly 300 into the interior of the anchor assembly 200).

In some implementations, the aforementioned rotation of the valve assembly 300 can be performed as follows. As shown in FIG. 26, because of the influence from the guide catheter 120 on the valve delivery catheter 180, the axis of the valve assembly 300 is initially in general alignment with the axis of the distal end portion of the guide catheter 120. From this arrangement, a generally simultaneous counter-movement of/between the inner catheter 160 and the valve delivery catheter 180 can be performed by the clinician to rotate the valve assembly 300. That is, as the inner catheter 160 is pulled proximally, the valve delivery catheter 180 is pushed distally. As a result of that counter movement, the valve assembly 300 rotates/pans in a relatively tight radius within the left atrium 16, as required by the confines of the left atrium 16. Thereafter, the valve delivery catheter 180 can be advanced further so that the valve assembly 300 is coaxially positioned within the interior of the anchor assembly 200 as shown in FIG. 28. As with other movements of the components of the delivery system 100 described herein (and other movements of the components of the delivery system 100 that are like those described herein), the generally simultaneous counter-movements of/between the inner catheter 160 and the valve delivery catheter 180 can be initiated and controlled using a deployment frame system (such as the example deployment frame system of FIG. 67 described below) in some implementations.

Figure 65:
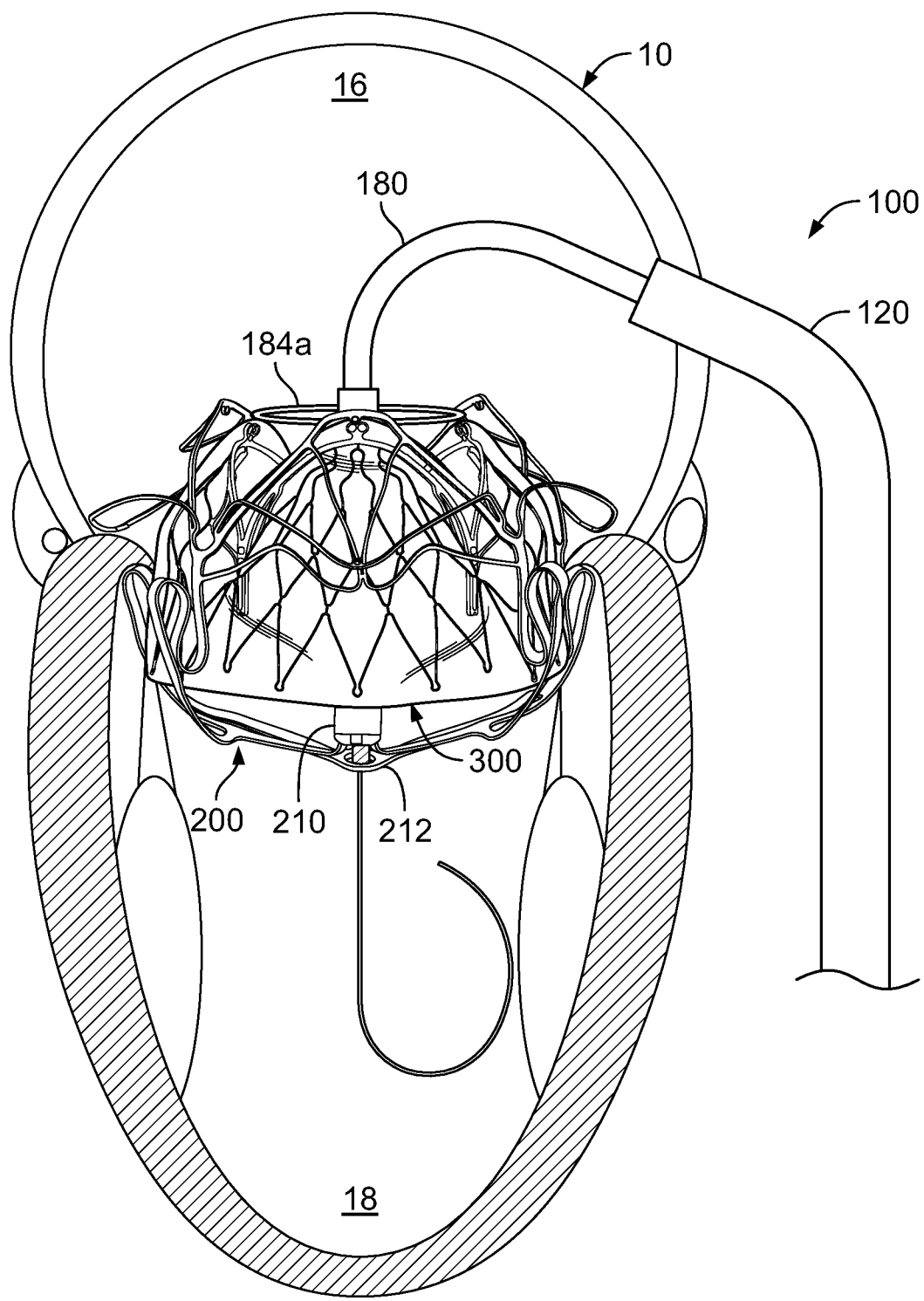
FIG. 65 shows a perspective view of the valve assembly of FIG. 62, with the valve assembly expanded within the anchor assembly, prior to deployment of the SAM containment member.
Figure 66:
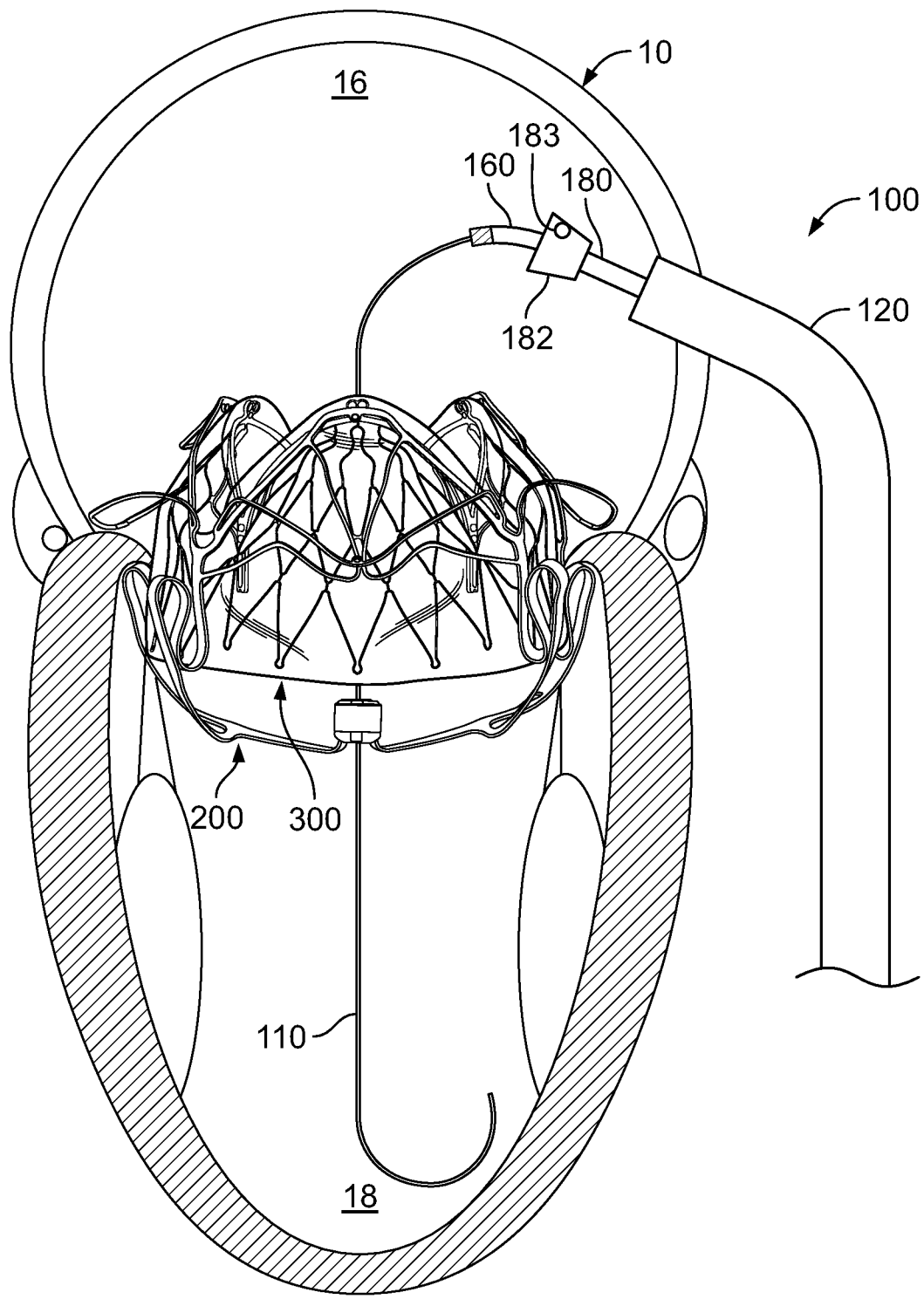
FIG. 66 shows a perspective view of the valve assembly of FIG. 62, with the valve assembly expanded within the anchor assembly after the release and retraction of the control wires of the deployment system, after deployment of the SAM containment member, and after the retraction of some of the catheters of the deployment system.

Referring now also to FIGS. 65 and 66, in some embodiments the valve assembly 300 and the anchor assembly 200 become aligned with each other coaxially, linearly (along their axes), and rotationally prior to or during the expansion of the valve assembly 300, resulting in engagement between the valve assembly 300 and the anchor assembly 200.

Coaxial alignment between the valve assembly 300 and the anchor assembly 200, as described above, is achieved by virtue of the valve delivery catheter 180 being slidably disposed over the inner catheter 160. Linear alignment between the valve assembly 300 and the anchor assembly 200 can be achieved by the interaction of a distal end feature 182 (FIG. 28) of the valve delivery catheter 180 and the hub 210 of the anchor assembly 200. For example, in some embodiments an abutting of the distal end feature 182 and the hub 210 can result in proper linear alignment between the valve assembly 300 and the anchor assembly 200. Such abutting of the distal end feature 182 and the hub 210 can be attained by translating the valve delivery catheter 180 distally until the distal end feature 182 abuts the hub 210.

Relative rotational alignment between the valve assembly 300 and the anchor assembly 200 (about their longitudinal axes) can be achieved in various manners. For example, in some embodiments the valve delivery catheter 180 is mechanically keyed to the inner catheter 160 to slidably fix a desired rotational alignment between the valve assembly 300 and the anchor assembly 200. In some embodiments, other types of mechanical features (e.g., pins/holes, protrusions/receptacles, etc.) can be included to facilitate a desired rotational/spin alignment between the valve assembly 300 and the anchor assembly 200. Alternatively, or additionally, one or more radiopaque markers can be included on the valve assembly 300 and/or on the anchor assembly 200 in locations and/or patterns that are indicative of the relative rotational orientation (about their axes) of the valve assembly 300 and the anchor assembly 200. Accordingly, fluoroscopy can be used to attain a desired relative orientation of the radiopaque markers and, consequently, of the valve assembly 300 and the anchor assembly 200. For example, in some embodiments one or more radiopaque markers 183 are disposed on the distal end feature 182. The one or more radiopaque markers 183 can be in locations and/or arranged in patterns to indicate the rotational orientation of the distal end feature 182 and, in turn, the rotational orientation of the valve assembly 300 that is releasably coupled in relation to the distal end feature 182. In some embodiments, the one or more radiopaque markers 183 can be arranged as one or more beads, one or more half-rings, and the like, and combinations thereof. One or more radiopaque markers can be included on the SAM containment member 212 in some embodiments.

In some embodiments (e.g., when the valve delivery catheter 180 is configured to be "torqueable"), the valve delivery catheter 180 can be rotated about its longitudinal axis until the radiopaque markers are in proper position relative to the anchor assembly 200, prior to final expansion of valve assembly 300. Such rotation of the valve delivery catheter 180 can, in some implementations, be initiated and controlled using a deployment frame. Fluoroscopy can be used to attain a desired relative orientation of the radiopaque markers, and of the valve assembly 300 and the anchor assembly 200 (including on the SAM containment member) correspondingly.

In the depicted implementation, the SAM containment member 212 is still in its pre-deployed configuration. Therefore, the depicted embodiment of the SAM containment member 212 is deployed after the valve assembly 300 is engaged within the anchor assembly 200. However, for some alternative embodiments of the SAM containment member (as described further below) the SAM containment member is deployed prior to the engagement of the valve assembly 300 within the anchor assembly 200.

After proper alignment between the valve assembly 300 and the anchor assembly 200 is achieved, the valve assembly 300 can be expanded within the interior of the anchor assembly 200 such that the valve assembly 300 and anchor assembly 200 become releasably coupled to each other. In some embodiments, force(s) are applied to the valve assembly 300 to cause it to expand. In some embodiments, the valve assembly 300 is biased to self-expand.

The expansion of a self-expanding valve assembly 300 can be initiated by releasing tension on the one or more control wires of the valve delivery catheter 180. For example, in some embodiments the valve delivery catheter 180 includes a proximal control wire 184a that restrains the proximal end portion of the valve assembly 300, and a distal control wire 184b that restrains the distal end portion of the valve assembly 300. As tension on the proximal control wire 184a is released, the proximal end portion of the valve assembly 300 is allowed to radially expand. Similarly, as tension on the distal control wire 184b is released, the distal end portion of the valve assembly 300 is allowed to radially expand. The expansions of the portions of the valve assembly 300 may be allowed to take place sequentially, concurrently, or partially concurrently. As described further below, such individual and/or simultaneous movements of components of the delivery system 100 (such as the one or more control wires of the valve delivery catheter 180) can be initiated and controlled using a deployment frame system in some implementations.

After the valve assembly 300 has been expanded into a coupled relationship with the anchor assembly 200, the clinician can verify that the anchor assembly 200 and the valve assembly 300 are in the desired positions. Additionally, the clinician may verify other aspects such as, but not limited to, the hemodynamic performance and sealing of the anchor assembly 200 and the valve assembly 300.

In some embodiments, the SAM containment member 212 is deployed after the valve assembly 300 has been expanded into a coupled relationship with the anchor assembly 200. To deploy the SAM containment member 212, in some embodiments the inner catheter 160 is rotated about its longitudinal axis so that the distal end of the inner catheter 160 is uncoupled from the hub 210 of the anchor assembly 200. For example, in some embodiments the distal end of the inner catheter 160 is uncoupled from the hub 210 by unthreading the distal end of the inner catheter 160 from the hub 210 by rotating the inner catheter 160 about its longitudinal axis. Then, in some embodiments the guidewire 110 is retracted to allow full deployment of the SAM containment member 212. The SAM containment member 212 may self-expand to its fully deployed configuration in some embodiments. The configuration of the fully deployed SAM containment member 212 is depicted in FIGS. 16-21, for example.

In its fully deployed configuration, the SAM containment member 212 is at least partially disposed behind the natural mitral valve anterior leaflet 20 (FIG. 12). The deployed SAM containment member 212 can reduce or prevent the potential for the natural mitral valve anterior leaflet 20 to "flop" outward and/or from being drawn by a Venturi effect into the left ventricular outflow tract (LVOT). Accordingly, the SAM containment member 212 can reduce the risk of full or partial blockages of the LVOT. In some patient scenarios, the potential for suffering future adverse health events, such as heart failure, is thereby reduced.

With the valve assembly 300 and the anchor assembly 200 fully deployed and functioning as desired, the remaining components of the delivery system 100 can be withdrawn. To do so, the valve delivery catheter 180 and the inner catheter 160 can be retracted into the guide catheter 120. Then the valve delivery catheter 180, the inner catheter 160, and the guide catheter 120 can be jointly or individually withdrawn from the patient.

Figure 67:
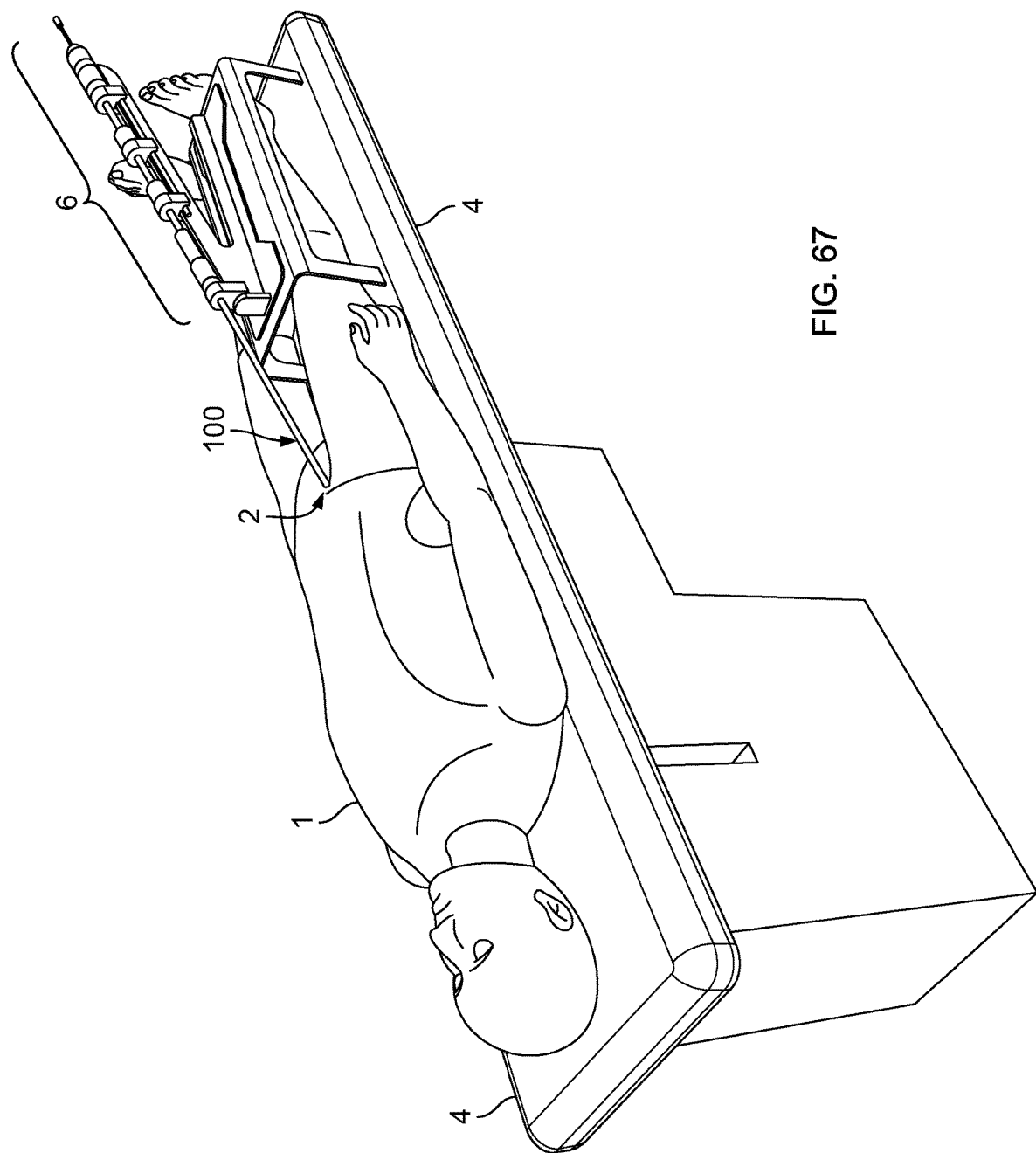
FIG. 67 shows a perspective view of an example prosthetic mitral valve system deployment frame system configuration in accordance with some embodiments.

Referring to FIG. 67, in some implementations the two-part prosthetic mitral valve system described above (comprising anchor assembly 200 and valve assembly 300) is deployed in a patient 1 using the transcatheter delivery system 100 as described above. In some implementations, the prosthetic mitral valve system is percutaneously deployed via a femoral or iliac vein through a groin opening/incision 2 in the patient 1. In particular implementations, a deployment frame system 6 is used to initiate and/or control the movements of various components of the transcatheter delivery system 100.

While the deployment frame system 6 is described in the context of the deployment of the prosthetic mitral valve system using the transcatheter delivery system 100, it should be understood that the practical applications of the inventive concepts associated with the deployment frame system 6 is not limited to such a context. That is, the inventive concepts associated with the deployment frame system 6 can be applied to contexts such as, but not limited to, other types of delivery systems for prosthetic heart valves of any type, deployment systems for other types of medical devices/implants, and so on.

In the depicted embodiment, the deployment frame system 6 is attached or releasably attached to an operating table 4 on which the patient 1 is laying. In some embodiments, the deployment frame system 6 is separated or substantially separated from the operating table 4.

As described above, the deployment of the prosthetic mitral valve system is, in summary, a two-step process. The first step is the deployment of the anchor assembly 200, and the second step is the deployment of the valve assembly 300. Some components of the deployment frame system 6 may be used for both steps, while other components of the deployment frame system 6 may be used for one or the other of the two steps.

In general, the configuration of the deployment frame system 6 is different for the two deployment steps (i.e., the first step being the deployment of the anchor assembly 200, and the second step being the deployment of the valve assembly 300). That is, the configuration of the deployment frame system 6 for delivering the anchor assembly 200 is different than the configuration of the deployment frame system 6 for delivering the valve assembly 300.

The transcatheter delivery system 100 can be releasably coupled with deployment frame system 6, as described further below. The deployment frame system 6 can be used by one or more clinicians to initiate and control movements of the components of the delivery system 100.

As described above, the example transcatheter delivery system 100 includes the guidewire 110, the guide catheter 120, the anchor delivery sheath 130, the anchor delivery catheter 140, the secondary steerable catheter 150, and the inner catheter 160. In general, in the depicted embodiment those components of delivery system 100 are disposed in a telescopic fashion in relation to each other. That is, the guidewire 110 is slidably disposed within the inner catheter 160; the inner catheter 160 is slidably disposed within the secondary steerable catheter 150; the secondary steerable catheter 150 is slidably disposed within the anchor delivery catheter 140; the anchor delivery catheter 140 is slidably disposed within the anchor delivery sheath 130; and the anchor delivery sheath 130 is slidably disposed within the guide catheter 120.

A proximal end portion of those components (e.g., the guide catheter 120, the anchor delivery sheath 130, the anchor delivery catheter 140, the secondary steerable catheter 150, and the inner catheter 160) can be terminated at a respective location along the deployment frame system 6. As described further below, by manipulating the respective components' proximal end portions (individually or in unison) using the deployment frame system 6, clinicians can initiate and control movements of the delivery system 100. In some embodiments, the example deployment frame system 6 includes a main frame and a secondary frame.

As described above, various movements of the components of the delivery system 100 may be desired during the process of deploying (or retrieving) a medical device, such as the anchor assembly 200 and the valve assembly 300. For example, the types of desired movements of the components of the delivery system 100 may include, but are not limited to: (i) a distal longitudinal translation, (ii) a proximal longitudinal translation, (iii) rotations about the longitudinal axis in either direction, (iv) a deflection of one or more portions of a component (e.g., steering or bending), and (v) a tensioning or un-tensioning of a control wire.

In some implementations, it may be desirable to initiate some of such movements (e.g., example movements (i)-(v) above) in synchronization (e.g., generally simultaneously) with one or more other such movements. One example, of desirable simultaneous movement of two or more components of the delivery system 100 was described above in reference to FIG. 7. In that example, the inner catheter 160 and the anchor delivery catheter 140 were translated distally in conjunction with each other, while maintaining the positions of the other components of the delivery system 100 (e.g., the secondary steerable catheter 150) generally stationary. The secondary frame of the deployment frame system 6 can be advantageously utilized to facilitate such synchronization of movements of two or more components of the delivery system 100.

A number of embodiments of the invention have been described. Nevertheless, it will be understood that various modifications may be made without departing from the scope of the invention. Accordingly, other embodiments are within the scope of the following claims.

What is claimed is:

1. A prosthetic mitral valve and deployment system, comprising:
   the prosthetic mitral valve comprising:
   an anchor assembly comprising an expandable anchor frame coupleable with a native mitral valve having an anterior leaflet and a posterior leaflet that cycle between an open valve orientation and a closed valve orientation in which free edges of the anterior and posterior leaflets oppose each other to define a coaptation line, wherein while the anchor assembly is coupled with the native mitral valve the anterior and posterior leaflets continue to cycle: and
   a valve assembly selectively coupleable with the anchor assembly; and
   the deployment system comprising multiple catheters configured to deliver the prosthetic mitral valve, wherein at least some of the catheters are releasably coupleable to the prosthetic mitral valve,
   wherein a first catheter of the multiple catheters is releasably coupleable to the anchor assembly and includes an expandable element that is positioned along the coaptation line between the free edges of the anterior and posterior leaflets.

2. The system of claim 1, wherein the expandable element comprises a selectively expandable balloon.

3. The system of claim 1, wherein the expandable element comprises a self-expanding wireframe and a covering material attached thereto.

4. The system of claim 1, wherein the expandable element comprises a passively-expandable, flexible sock member.

5. The system of claim 1, wherein the anchor assembly comprises a hub that is positioned inferior to the annulus of the native mitral valve while the anchor assembly is coupled with the native mitral valve, and wherein the first catheter is releasably coupleable to the hub.

6. The system of claim 1, wherein the expandable element is coupled to an outer diameter of the first catheter.

7. The system of claim 6, further comprising a second catheter configured to slide over the first catheter, and the second catheter is configured to diametrically constrain the expandable element.

8. The system of claim 1, wherein the expandable element is configured to expand into a generally cylindrical shape.

9. A deployment system for a prosthetic mitral valve, the deployment system comprising:

a plurality of catheters configured to deliver the prosthetic mitral valve;

a first catheter of the plurality of catheters configured to deliver an anchor assembly of the prosthetic mitral valve and an expandable element;

wherein the anchor assembly comprises an expandable anchor frame coupleable with a native mitral valve having an anterior leaflet and a posterior leaflet that cycle between an open valve orientation and a closed valve orientation in which free edges of the anterior and posterior leaflets oppose each other to define a coaptation line, wherein while the anchor assembly is coupled with the native mitral valve the anterior and posterior leaflets continue to cycle; and wherein the expandable element is positioned along the coaptation line between the free edges of the anterior and posterior leaflets.

10. The system of claim 9, wherein the expandable element is coupled to an outer diameter of the first catheter.

11. The system of claim 10, further comprising a second catheter configured to slide over the first catheter, and the second catheter is configured to diametrically constrain the expandable element.

12. The system of claim 9, wherein the expandable element comprises a selectively expandable balloon.

13. The system of claim 9, wherein the expandable element comprises a self-expanding wireframe and a covering material attached thereto.

14. The system of claim 9, wherein the expandable element comprises a passively-expandable, flexible sock member.

15. The system of claim 9, wherein the expandable element is configured to extend across the coaptation line during a contracted state, and selectively expand to occupy open space between the free edges of the native leaflets.

* * * * *